(12) United States Patent
Wang et al.

US009125923B2

(10) Patent No.: US 9,125,923 B2
(45) Date of Patent: Sep. 8, 2015

(54) USE OF MIR-26 FAMILY AS A PREDICTIVE MARKER FOR HEPATOCELLULAR CARCINOMA AND RESPONSIVENESS TO THERAPY

(75) Inventors: Xin W. Wang, Rockville, MD (US); Junfang Ji, Bethesda, MD (US); Carlo M. Croce, Columbus, OH (US); Hui-chuan Sun, Shanghai (CN); Zhao-you Tang, Shanghai (CN)

(73) Assignees: The Ohio State University, Columbus, OH (US); Fudan University, Shanghai (CN); The United States of America as Represented by the Secretary of the Dept. of Health and Human Services, Washington, DC (US)

( * ) Notice: Subject to any disclaimer, the term of this patent is extended or adjusted under 35 U.S.C. 154(b) by 341 days.

(21) Appl. No.: 12/997,419

(22) PCT Filed: Jun. 11, 2009

(86) PCT No.: PCT/US2009/046999
§ 371 (c)(1),
(2), (4) Date: Jan. 18, 2011

(87) PCT Pub. No.: WO2009/152300
PCT Pub. Date: Dec. 17, 2009

(65) Prior Publication Data
US 2011/0124521 A1 May 26, 2011

Related U.S. Application Data

(60) Provisional application No. 61/131,800, filed on Jun. 11, 2008.

(51) Int. Cl.
*C40B 30/04* (2006.01)
*A61K 31/70* (2006.01)
*C12Q 1/68* (2006.01)

(52) U.S. Cl.
CPC .............. *A61K 31/70* (2013.01); *C12Q 1/6809* (2013.01); *C12Q 1/6886* (2013.01); *C12Q 2600/106* (2013.01)

(58) Field of Classification Search
None
See application file for complete search history.

(56) References Cited

U.S. PATENT DOCUMENTS

| | | | |
|---|---|---|---|
| 4,172,124 A | 10/1979 | Koprowski et al. |
| 4,196,265 A | 4/1980 | Koprowski et al. |
| 4,608,337 A | 8/1986 | Croce |
| 4,693,975 A | 9/1987 | Kozbor et al. |
| 4,701,409 A | 10/1987 | Croce |
| 5,015,568 A | 5/1991 | Tsujimoto et al. |
| 5,149,628 A | 9/1992 | Croce |
| 5,198,338 A | 3/1993 | Croce |
| 5,202,429 A | 4/1993 | Tsujimoto et al. |
| 5,459,251 A | 10/1995 | Tsujimoto et al. |
| 5,506,106 A | 4/1996 | Croce et al. |
| 5,506,344 A | 4/1996 | Tsujimoto et al. |
| 5,523,393 A | 6/1996 | Tsujimoto et al. |
| 5,567,586 A | 10/1996 | Croce |
| 5,595,869 A | 1/1997 | Tsujimoto et al. |
| 5,633,135 A | 5/1997 | Croce et al. |
| 5,633,136 A | 5/1997 | Croce et al. |
| 5,674,682 A | 10/1997 | Croce et al. |
| 5,688,649 A | 11/1997 | Croce et al. |
| 5,695,944 A | 12/1997 | Croce et al. |
| 5,928,884 A | 7/1999 | Croce et al. |
| 5,939,258 A | 8/1999 | Croce et al. |
| 5,985,598 A | 11/1999 | Russo et al. |
| 6,040,140 A | 3/2000 | Croce et al. |
| 6,130,201 A | 10/2000 | Croce et al. |
| 6,187,536 B1 | 2/2001 | Weinberg et al. |
| 6,242,212 B1 | 6/2001 | Croce et al. |
| 6,255,293 B1 | 7/2001 | Kimchi |

(Continued)

FOREIGN PATENT DOCUMENTS

| | | |
|---|---|---|
| CA | 2533701 A1 | 2/2005 |
| CA | 2587189 | 12/2006 |
| FR | 2877350 A1 | 5/2006 |
| WO | 90/15156 | 12/1990 |
| WO | 91/00364 | 1/1991 |
| WO | 91/07424 | 5/1991 |

(Continued)

OTHER PUBLICATIONS

Lago—Quintana et al in Science vol. 294, p. 853; 2001.*
Varnholt et al in "MicroRNA Gene Expression Profile of Hepatitis C Virus-Associated Hepatocellular Carcinoma" (Hepatology, Apr. 2008; vol. 47: pp. 1223-1232).*
European Seach Report, Application No. 09714868.8 dated Aug. 1, 2011.
Canadian Office Action, Application No. 2,617,581, dated Feb. 1, 2011.

(Continued)

*Primary Examiner* — Catherine S Hibbert
(74) *Attorney, Agent, or Firm* — MacMillan, Sobanski & Todd, LLC

(57) ABSTRACT

It is disclosed herein that expression of microRNA-26 is decreased in hepatocellular (HCC) tumor tissue relative to non-cancerous tissue, and that a low level of microRNA-26 is associated with a poor clinical outcome. It is also disclosed herein that a low expression level of microRNA-26 is correlated with a favorable response to interferon (IFN)-α therapy in HCC patients. Thus, provided herein is a method of predicting the clinical outcome of a patient diagnosed with HCC comprising detecting the level of microRNA-26 expression in a sample obtained from the patient. Also provided is a method of selecting a patient diagnosed with HCC as a candidate for IFN-α therapy, comprising detecting the level of microRNA-26 expression in a sample obtained from the patient. A method of identifying therapeutic agents for the treatment of HCC, comprising screening candidate agents in vitro to select an agent that increases expression of microRNA-26 in HCC cells are also provided. Further provided are methods of treating a patient diagnosed with HCC and expressing a low level of miR-26, wherein treatment comprises IFN-α therapy.

18 Claims, 22 Drawing Sheets

(56) References Cited

U.S. PATENT DOCUMENTS

| | | |
|---|---|---|
| 6,258,541 B1 | 7/2001 | Chapkin et al. |
| 6,774,217 B1 | 8/2004 | Croce et al. |
| 6,924,414 B2 | 8/2005 | Croce et al. |
| 7,060,811 B2 | 6/2006 | Aldaz et al. |
| 7,141,417 B1 | 11/2006 | Croce et al. |
| 7,175,995 B1 | 2/2007 | Russo et al. |
| 7,217,568 B2 | 5/2007 | Jamieson et al. |
| 7,220,834 B2 | 5/2007 | Croce et al. |
| 7,232,806 B2 | 6/2007 | Tuschl et al. |
| 7,390,792 B2 | 6/2008 | Srivastava et al. |
| 7,585,969 B2 | 9/2009 | Stoffel et al. |
| 7,592,441 B2 | 9/2009 | Bentwich et al. |
| 7,618,814 B2 | 11/2009 | Bentwich et al. |
| 7,642,348 B2 | 1/2010 | Bentwich et al. |
| 7,667,090 B2 | 2/2010 | Croce |
| 7,670,840 B2 | 3/2010 | Croce et al. |
| 7,709,616 B2 | 5/2010 | Bentwich et al. |
| 7,723,030 B2 | 5/2010 | Croce et al. |
| 7,723,035 B2 | 5/2010 | Croce et al. |
| 7,728,189 B2 | 6/2010 | Croce |
| 7,749,715 B2 | 7/2010 | Russo et al. |
| 7,777,005 B2 | 8/2010 | Croce et al. |
| 2001/0026796 A1 | 10/2001 | Croce et al. |
| 2002/0086331 A1 | 7/2002 | Croce et al. |
| 2002/0116726 A1 | 8/2002 | Croce et al. |
| 2002/0132290 A1 | 9/2002 | Frazer |
| 2004/0033502 A1 | 2/2004 | Williams et al. |
| 2004/0078834 A1 | 4/2004 | Croce |
| 2004/0152112 A1 | 8/2004 | Croce et al. |
| 2004/0265316 A1 | 12/2004 | Croce et al. |
| 2004/0265930 A1 | 12/2004 | Sun et al. |
| 2005/0019890 A1 | 1/2005 | Croce |
| 2005/0059005 A1 | 3/2005 | Tuschl et al. |
| 2005/0069918 A1 | 3/2005 | Claret |
| 2005/0074797 A1 | 4/2005 | Croce et al. |
| 2005/0075492 A1 | 4/2005 | Chen et al. |
| 2005/0112630 A1 | 5/2005 | Shaughnessy et al. |
| 2005/0164252 A1 | 7/2005 | Yeung |
| 2005/0176025 A1 | 8/2005 | McSwiggen et al. |
| 2005/0181385 A1 | 8/2005 | Linsley et al. |
| 2005/0186589 A1 | 8/2005 | Kowalik et al. |
| 2005/0256072 A1 | 11/2005 | Aronin et al. |
| 2005/0260639 A1 | 11/2005 | Nakamura et al. |
| 2005/0266443 A1 | 12/2005 | Croce et al. |
| 2005/0287530 A1 | 12/2005 | Croce et al. |
| 2006/0019286 A1 | 1/2006 | Horvitz et al. |
| 2006/0024780 A1 | 2/2006 | Aldaz et al. |
| 2006/0037088 A1 | 2/2006 | Li |
| 2006/0075511 A1 | 4/2006 | Croce et al. |
| 2006/0084059 A1 | 4/2006 | Yip et al. |
| 2006/0099619 A1 | 5/2006 | Remacle et al. |
| 2006/0105340 A1 | 5/2006 | Croce et al. |
| 2006/0105360 A1 | 5/2006 | Croce et al. |
| 2006/0127895 A1 | 6/2006 | Sabapathy |
| 2006/0165659 A1 | 7/2006 | Croce et al. |
| 2006/0166918 A1 | 7/2006 | Heidenreich et al. |
| 2006/0185027 A1 | 8/2006 | Bartel et al. |
| 2006/0188924 A1 | 8/2006 | Russo et al. |
| 2006/0188959 A1 | 8/2006 | Croce et al. |
| 2006/0189557 A1 | 8/2006 | Slack et al. |
| 2006/0247448 A1 | 11/2006 | Boivin et al. |
| 2006/0292616 A1 | 12/2006 | Neely et al. |
| 2007/0036765 A1 | 2/2007 | Civin et al. |
| 2007/0050146 A1 | 3/2007 | Bentwich et al. |
| 2007/0054849 A1 | 3/2007 | Nakamura et al. |
| 2007/0065840 A1 | 3/2007 | Naguibneva et al. |
| 2007/0065844 A1 | 3/2007 | Golub et al. |
| 2007/0072230 A1 | 3/2007 | Croce et al. |
| 2007/0099196 A1 | 5/2007 | Kauppinen et al. |
| 2007/0123482 A1 | 5/2007 | Stoffel et al. |
| 2007/0161004 A1* | 7/2007 | Brown et al. ............... 435/6 |
| 2007/0178105 A1 | 8/2007 | Croce et al. |
| 2007/0178502 A1 | 8/2007 | Reed |
| 2007/0212727 A1 | 9/2007 | Szalay et al. |
| 2007/0213292 A1 | 9/2007 | Stoffel et al. |
| 2007/0259352 A1 | 11/2007 | Bentwich et al. |
| 2007/0292878 A1 | 12/2007 | Raymond |
| 2008/0026951 A1 | 1/2008 | Brown et al. |
| 2008/0050744 A1 | 2/2008 | Brown et al. |
| 2008/0171667 A1 | 7/2008 | Brown et al. |
| 2008/0176766 A1 | 7/2008 | Brown et al. |
| 2008/0182245 A1 | 7/2008 | Brown et al. |
| 2008/0193943 A1 | 8/2008 | Murray |
| 2008/0254473 A1 | 10/2008 | Chen et al. |
| 2008/0256650 A1 | 10/2008 | Croce |
| 2008/0261908 A1 | 10/2008 | Croce et al. |
| 2008/0306006 A1 | 12/2008 | Croce et al. |
| 2008/0306017 A1 | 12/2008 | Croce et al. |
| 2008/0306018 A1 | 12/2008 | Croce et al. |
| 2009/0005336 A1 | 1/2009 | Wang |
| 2009/0023594 A1 | 1/2009 | Mouritzen et al. |
| 2009/0029932 A1 | 1/2009 | Voinnet et al. |
| 2009/0061424 A1 | 3/2009 | Chen |
| 2009/0092974 A1 | 4/2009 | Davison et al. |
| 2009/0099034 A1 | 4/2009 | Ahlquist et al. |
| 2009/0123533 A1 | 5/2009 | Croce et al. |
| 2009/0123912 A1 | 5/2009 | Raymond |
| 2009/0123933 A1 | 5/2009 | Mishra |
| 2009/0131348 A1 | 5/2009 | Labourier et al. |
| 2009/0131354 A1 | 5/2009 | Bader et al. |
| 2009/0131356 A1* | 5/2009 | Bader et al. ............... 514/44 |
| 2009/0163430 A1 | 6/2009 | Johnson et al. |
| 2009/0163434 A1 | 6/2009 | Bader et al. |
| 2009/0163435 A1 | 6/2009 | Bader et al. |
| 2009/0175827 A1 | 7/2009 | Byrom et al. |
| 2009/0176723 A1 | 7/2009 | Brown et al. |
| 2009/0192102 A1 | 7/2009 | Bader et al. |
| 2009/0192111 A1 | 7/2009 | Bader et al. |
| 2009/0192114 A1 | 7/2009 | Ovcharenko et al. |
| 2009/0209450 A1 | 8/2009 | Croce et al. |
| 2009/0222934 A1 | 9/2009 | Croce |
| 2009/0227533 A1 | 9/2009 | Bader et al. |
| 2009/0232893 A1 | 9/2009 | Bader et al. |
| 2009/0233297 A1 | 9/2009 | Mambo et al. |
| 2009/0253780 A1 | 10/2009 | Takeshita et al. |
| 2009/0263803 A1 | 10/2009 | Beaudenon et al. |
| 2009/0270484 A1 | 10/2009 | Croce et al. |
| 2009/0281167 A1 | 11/2009 | Shen et al. |
| 2009/0306194 A1 | 12/2009 | Ford et al. |
| 2010/0004322 A1 | 1/2010 | Croce |
| 2010/0048681 A1 | 2/2010 | Croce |
| 2010/0120898 A1 | 5/2010 | Croce et al. |
| 2010/0137410 A1 | 6/2010 | Croce |
| 2010/0144850 A1 | 6/2010 | Croce |
| 2010/0173319 A1 | 7/2010 | Croce et al. |
| 2010/0184032 A1 | 7/2010 | Georgantas et al. |
| 2010/0184830 A1 | 7/2010 | Croce et al. |
| 2010/0184842 A1 | 7/2010 | Croce |
| 2010/0192235 A1 | 7/2010 | Croce |
| 2010/0197770 A1 | 8/2010 | Wang et al. |
| 2010/0197774 A1 | 8/2010 | Croce et al. |
| 2010/0203544 A1 | 8/2010 | Croce et al. |
| 2010/0234241 A1 | 9/2010 | Croce et al. |
| 2010/0249213 A1 | 9/2010 | Croce |
| 2010/0257618 A1 | 10/2010 | Croce et al. |
| 2010/0317610 A1 | 12/2010 | Croce |

FOREIGN PATENT DOCUMENTS

| | | |
|---|---|---|
| WO | 93/12136 | 6/1993 |
| WO | 94/10343 | 5/1994 |
| WO | 94/24308 | 10/1994 |
| WO | 94/26930 | 11/1994 |
| WO | 96/13514 | 5/1996 |
| WO | 96/35124 | 11/1996 |
| WO | 97/29119 | 8/1997 |
| WO | 98/09510 | 3/1998 |
| WO | 00/03685 | 1/2000 |
| WO | 00/50565 | 8/2000 |
| WO | 00/55169 | 9/2000 |
| WO | 00/76524 | 12/2000 |
| WO | 01/44466 | 6/2001 |
| WO | 01/68666 | 9/2001 |
| WO | 01/77343 | 10/2001 |

(56) References Cited

FOREIGN PATENT DOCUMENTS

| | | |
|---|---|---|
| WO | 01/87958 | 11/2001 |
| WO | 02/064171 | 8/2002 |
| WO | 02/064172 | 8/2002 |
| WO | 03/029459 | 4/2003 |
| WO | 03/078662 | 9/2003 |
| WO | 03/092370 | 11/2003 |
| WO | 2004/033659 | 4/2004 |
| WO | 2004/043387 | 5/2004 |
| WO | 2004/079013 | 9/2004 |
| WO | 2004/098377 | 11/2004 |
| WO | 2005/017711 | 2/2005 |
| WO | 2005/020795 | 3/2005 |
| WO | 2005060661 | 7/2005 |
| WO | 2005/078139 | 8/2005 |
| WO | 2005/080601 | 9/2005 |
| WO | 2005079397 A2 | 9/2005 |
| WO | 2005103298 A2 | 11/2005 |
| WO | 2005/118806 | 12/2005 |
| WO | 2006/105486 | 10/2006 |
| WO | 2006/108718 | 10/2006 |
| WO | 2006108718 | 10/2006 |
| WO | 2006/119266 | 11/2006 |
| WO | 2006/133022 | 12/2006 |
| WO | 2006/137941 | 12/2006 |
| WO | 2007/016548 | 2/2007 |
| WO | 2007016548 A2 | 2/2007 |
| WO | 2007/033023 | 3/2007 |
| WO | 2007/044413 | 4/2007 |
| WO | 2007/081680 | 7/2007 |
| WO | 2007/081720 | 7/2007 |
| WO | 2007/081740 | 7/2007 |
| WO | 2007/084486 | 7/2007 |
| WO | 2007/109236 | 9/2007 |
| WO | 2007112097 | 10/2007 |
| WO | 2007112754 A2 | 10/2007 |
| WO | 2007/127190 | 11/2007 |
| WO | 2008/008430 | 1/2008 |
| WO | 2008/036776 | 3/2008 |
| WO | 2008/054828 | 5/2008 |
| WO | 2008/070082 | 6/2008 |
| WO | 2008/073920 | 6/2008 |
| WO | 2008073915 | 6/2008 |
| WO | 2008/094545 | 8/2008 |
| WO | 2008/097277 | 8/2008 |
| WO | 2008/136971 | 11/2008 |
| WO | 2008/153987 | 12/2008 |
| WO | 2008/157319 | 12/2008 |
| WO | 2009/018303 | 2/2009 |
| WO | 2009/020905 | 2/2009 |
| WO | 2009/026487 | 2/2009 |
| WO | 2009/033140 | 3/2009 |
| WO | 2009/049129 | 4/2009 |
| WO | 2009/055773 | 4/2009 |
| WO | 2009/064590 | 5/2009 |
| WO | 2009/070653 | 6/2009 |
| WO | 2009/100029 | 8/2009 |
| WO | 2009/108853 | 9/2009 |
| WO | 2009/108856 | 9/2009 |
| WO | 2009/108860 | 9/2009 |
| WO | 2009/108866 | 9/2009 |
| WO | 2009/152300 | 12/2009 |
| WO | 2010/019694 | 2/2010 |
| WO | 2010/059779 | 5/2010 |
| WO | 2010/065156 | 6/2010 |
| WO | 2010/099161 | 9/2010 |

OTHER PUBLICATIONS

European Communication Pursuant to Article 94(3) EPC, Application No. 08768266.2, dated Apr. 18, 2011.
European Search Reoprt, Application No. 08841700.1, dated Jan. 4, 2011.
European Search Report, Application No. 08713330.2, dated Jul. 22, 2011.
European Search Report, Application No. 09713926.5 dated Jul. 21, 2011.
Chinese Office Action, Application No. 200780005821.2 dated Jan. 26, 2011.
Canadian Office Action, Application No. 2,621,441, dated Feb. 1, 2011.
PCT International Preliminary Report on Patentability, PCT/US2009/065072 filed Nov. 19, 2009, dated Jun. 3, 2011.
PCT International Preliminary Report on Patentability, PCT/US2010/025173 filed Feb. 24, 2010, dated Sep. 9, 2011.
PCT International Preliminary Report on Patentability, PCT/US2009/038214 filed Mar. 25, 2009, dated Jun. 16, 2011.
European Search Report, Application No. 11151771-0, dated Feb. 8, 2011, 57-52774.
European Communication Pursuant to Article 94(3) EPC, Application No. 08767439.9, dated Mar. 15, 2011.
Chinese Office Action, Application No. 200680039776.8 dated Jun. 30, 2011.
Australian Office Action, Application No. 2006291165 dated Aug. 23, 2011.
European Search Report, Application No. 11151772-8, dated Feb. 8, 2011.
European Search Report, Application No. 11151769-4, dated Feb. 8, 2011.
European Seach Report, Application No. 11151749.6, dated Feb. 8, 2011.
Chinese Office Action, Application No. 200680036598.3 dated Feb. 24, 2011.
Alvarez-Secord, A. et al., "Maspin Expression in Epithelial Ovarian Cancer and Associations with Poor Prognosis: A Gynecologic Oncology Group Study," Gynecologic Oncology, 2006, pp. 390-397, vol. 101.
Cannistra, S.A., "Cancer of the Ovary," The New England Journal of Medicine, 2004, pp. 2519-2529, vol. 351, No. 25.
Chim, S.S.C. et al., "Detection and Characterization of Placental MicroRNAs in Maternal Plasma," Clinical Chemistry, 2008, pp. 482-490, vol. 54, No. 3.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Feng, G. et al., "Elevated Serum-Circulating RNA in Patients with Conventional Renal Cell Cancer," Anticancer Research, 2008, pp. 321-326, vol. 28.
He, L. et al., "A MicroRNA Polycistron as a Potential Human Oncogene," Nature, Jun. 2005, pp. 828-833, vol. 435.
Ishii, H. et al., "Effect of Adenoviral Transduction of the Fragile Histidine Triad Gene into Esophageal Cancer Cells," Cancer Research, Feb. 2001, pp. 1578-1584, vol. 61.
Jacobs, I.J. et al., "Prevalence Screening for Ovarian Cancer in Postmenopausal Women by CA 125 Measurement and Ultrasonography," BMJ, Apr. 1993, pp. 1030-1034, vol. 306.
Jacobs, I.J. et al., "Progress and Challenges in Screening for Early Detection of Ovarian Cancer," Molecular & Cellular Proteomics, 2004, pp. 355-366, vol. 3.
Jemal, A. et al., "Cancer Statistics, 2008," CA Cancer J. Clin., 2008, pp. 71-96, vol. 58, No. 2.
Lawrie, C.H. et al., "Detection of Elevated Levels of Tumour-Associated MicroRNAs in Serum of Patients with Diffuse Large B-Cell Lymphoma," British Journal of Haematology, 2008, pp. 672-675, vol. 141.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Mendell, J.T., "miRiad Roles for the miR-17-92 Cluster in Development and Disease," Cell, 2008, pp. 217.
Meng, F. et al., "MicroRNA-21 Regulates Expression of the PTEN Tumor Suppressor Gene in Human Hepatocellular Cancer," Gastroenterology, 2007, pp. 647-658, vol. 133.
Nam, E.J. et al., "MicroRNA Expression Profiles in Serous Ovarian Carcinoma," Clinical Cancer Research, 2008, pp. 2690-2695, vol. 14, No. 9.

(56) References Cited

OTHER PUBLICATIONS

Olivier, R.I. et al., "CA125 and Transvaginal Ultrasound Monitoring in High-Risk Women Cannot Prevent the Diagnosis of Advanced Ovarian Cancer," Gynecologic Oncology, 2006, pp. 20-26, vol. 100.
Petrocca, F. et al., "MicroRNAs Deregulation in Gastric Cancer," PNAS, Apr. 2006, p. 1338, vol. 47, Abstract #5690.
Saito, Y. et al., "Specific Activation of MicroRNA-127 with Downregulation of the Proto-Oncogene BCL6 by Chromatin-Modifying Drugs in Human Cancer Cells," Cancer Cell, Jun. 2006, pp. 435-443, vol. 9.
Schagen, F. et al., "Genetic Targeting of Adenovirus Vectors Using a Reovirus Signal-Based Attachment Protein," Molecular Therapy, May 2006, pp. 997-1005, vol. 13, No. 5.
Taylor, D.D. et al., "MicroRNA Signatures of Tumor-Derived Exosomes as Diagnostic Biomarkers of Ovarian Cancer," Gynecologic Oncology, 2008, pp. 13-21, vol. 110.
Thomson, M., Supplementary data for "A Custon Microarray Platform for Analysis of MicroRNA Gene Expression," Nature Methods, Oct. 2004, pp. 47-53, vol. 1, No. 1.
Tili, E. et al., "Expression and Function of Micro RNAs in Immune Cells During Normal or Disease State," International Journal of Medicine Sciences, 2008, pp. 73-79, vol. 5, No. 2.
Uil, T.G. et al., "Generation of an Adenoviral Vector Containing an Addition of a Heterologous Ligand to the Serotpe 3 Fiber Knob," Cancer Gene Therapy, Feb. 2003, pp. 121-124, vol. 10, No. 2.
Verschuur, A.C., "Acute Megakaryoblastic Leukemia," May 2004, pp. 1-5, Retrieved from the Internet: URL: http://www.orpga.net/data/patho/GB/uk-AMLM7.pdf.
Zawacka-Pankau, J. et al., "Expression and Simple, One-Step Purification of Fragile Histidine Triad (Fhit) Tumor Suppressor Mutant Forms in *Escherichia coli* and their Interaction with Protoporphyrin IX," Biotechnology Letters, Jun. 2007, pp. 877-883, vol. 29, No. 6.
Australian Office Action, Application No. 2007205257 dated Dec. 22, 2011.
Australian Office Action, Application No. 2007205234 dated Sep. 20, 2011.
European Communication Pursuant to Article 94(3)EPC, Application No. 06814375.9 dated Oct. 14, 2011.
European Communication Pursuant to Article 94(3) EPC, Application No. 08799295.4, dated Nov. 18, 2011.
European Communication Pursuant to Article 94(3) EPC, Application No. 07716208.9, dated Sep. 13, 2011.
European Search Report, Application No. 08770974.4, dated Oct. 21, 2011.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Wiemer et al., "The Role of MicroRNAs in Cancer: No Small Matter," European Journal of Cancer, Jun. 12, 2007, vol. 43, No. 10, pp. 1529-1544.
Akahoshi, M. et al., "Myeloproliferative Disorders Terminating in Acute Megakaryoblastic Leukemia with Chromosome 3q26 Abnormality," Cancer, 1987, pp. 2654-2661, vol. 60.
Akao, Y. et al., "let-7 MicroRNA Functions as a Potential Growth Suppressor in Human Colon Cancer Cells," Biol. Pharm. Bull., May 2006, pp. 903-906, vol. 29, No. 5.
Ambros, V. et al., "A Uniform System for MicroRNA Annotation," RNA, 2003, pp. 277-279, vol. 9.
Ambs, S. et al., "Genomic Profiling of MicroRNA and Messenger RNA Reveals Deregulated MicroRNA Expression in Prostate Cancer," Cancer Research, Aug. 2008, pp. 6162-6170, vol. 68, No. 15.
Aqeilan, R. I. et al., "Targeted Deletion of WWOX Reveals a Tumor Suppressor Function," PNAS, Mar. 2007, pp. 3949-3954, vol. 104, No. 10.
Baira, E. et al., "Ultraconserved Elements: Genomics, Function and Disease," RNA Biology, Jul. 2008, pp. 132-134, vol. 5, No. 3.
Bandres, E. et al., "Identification by Real-Time PCR of 13 Mature MicroRNAs Differentially Expressed in Colorectal Cancer and Non-Tumoral Tissues," Molecular Cancer, Jul. 2006, 10 pages, vol. 5, No. 29.
Bartel, D. P., "MicroRNAs: Target Recognition and Regulatory Functions," Cell, Jan. 2009, pp. 215-233, vol. 136.
Bednarek, A. K. et al., "WWOX, the FRA16D Gene, Behaves as a Suppressor of Tumor Growth," Cancer Research, Nov. 2001, pp. 8068-8073, vol. 61.
Bejenaro, et al., "Ultraconserved Elements in the Human Genome," Electronic Suppl. Data, Science, 2004.
Bejerano, G. et al., "Ultraconserved Elements in the Human Genome," Science, May 2004, pp. 1321-1325, vol. 304.
Bell, D. A., "Origins and Molecular Pathology of Ovarian Cancer," Modern Pathology, 2005, pp. S19-S32, vol. 18.
Bichi, R. et al., "Human Chronic Lymphocytic Leukemia Modeled in Mouse by Targeted TCL1 Expression," PNAS, May 2002, pp. 6955-6960, vol. 99, No. 10.
Bloomston, M. et al., "MicroRNA Expression Patterns to Differentiate Pancreatic Adenocarcinoma from Normal Pancreas and Chronic Pancreatitis," JAMA, May 2007, pp. 1901-1908 vol. 297, No. 1.
Blum, W. et al., "Clinical Response and miR-29b Predictive Significance in Older AML Patients Treated With a 10-Day Schedule of Decitabine," PNAS, Apr. 2010, pp. 7473-7478, vol. 107, No. 16.
Boland, C.R. et al., "Lynch Syndrome: Form, Function, Proteins, and Basketball," Gastroenterology, Aug. 2005, pp. 751-755, vol. 129, No. 2.
Brueckner, B. et al., "The Human let-7a-3 Locus Contains an Epigenetically Regulated MicroRNA Gene with Oncogenic Function," Cancer Research, Feb. 2007, pp. 1419-1423, vol. 67, No. 4.
Budhu, A. et al., "A Unique Metastasis-Related MicroRNA Expression Signature is a Prognostic Indicator of Survival and Recurrence in Hepatocellular Carcinoma," Hepatology, 2007, p. 791A, vol. 46, No. 4, Suppl. 1, Abstract #1249.
Budhu, A. et al., "Identification of Metastasis-Related MicroRNAs in Hepatocellular Carcinoma," Hepatology, Mar. 2008, pp. 897-907, vol. 47, No. 3.
Caldas, C. et al., "Sizing Up miRNAs as Cancer Genes," Nature Medicine, Jul. 2005, pp. 712-714, vol. 11, No. 7.
Calin, G. A. et al., "A MicroRNA Signature Associated with Prognosis and Progression in Chronic Lymphocytic Leukemia," The New England Journal of Medicine, Oct. 2005, pp. 1793-1801, vol. 353, No. 17.
Calin, G. A. et al., "Chromosomal Rearrangements and MicroRNAs: A New Cancer Link with Clinical Implications," The Journal of Clinical Investigation, Aug. 2007, pp. 2059-2066, vol. 117, No. 8.
Calin, G. A. et al., "Frequent Deletions and Down-Regulation of MicroRNA Genes miR15 and miR16 at 13q14 in Chronic Lymphocytic Leukemia," PNAS, Nov. 2002, pp. 15524-15529, vol. 99, No. 24.
Calin, G.A. et al., "Human MicroRNA Genes are Frequently Located at Fragile Sites and Genomic Regions Involved in Cancers," PNAS, Mar. 2004, pp. 2999-3004, vol. 101, No. 9.
Calin, G. A. et al., "MicroRNA Profiling Reveals Distinct Signatures in B Cell Chronic Lymphocytic Leukemias," PNAS, Aug. 2004, pp. 11755-11760, vol. 101, No. 32.
Calin, G. A. et al., "MicroRNA Signatures in Human Cancers," Nature Reviews Cancer, Nov. 2006, pp. 857-866, vol. 6.
Calin, G. A. et al., "MiR-15a and MiR-16-1 Cluster Functions in Human Leukemia," PNAS, Apr. 2008, pp. 5166-5171, vol. 105, No. 13.
Calin, G. A. et al., "Ultraconserved Regions Encoding ncRNAs are Altered in Human Leukemias and Carcinomas," Cancer Cell, Sep. 2007, pp. 215-229, vol. 12.
Canadian Intellectual Property Office, Requisition by the Examiner, Application No. 2,635,616, Dated Feb. 21, 2011.
Castoldi, M. et al., "A Sensitive Array for MicroRNA Expression Profiling (miChip) Based on Locked Nucleic Acids (LNA)," RNA, 2006, pp. 913-920, vol. 12.
Chan, J. A. et al., "MicroRNA-21 is an Antiapoptotic Factor in Human Glioblastoma Cells," Cancer Research, Jul. 2005, pp. 6029-6033, vol. 65, No. 14.
Chang, N.-S. et al., "Molecular Mechanisms Underlying WOX1 Activation During Apoptotic and Stress Responses," Biochemical Pharmacology, 2003, pp. 1347-1354, vol. 66.

(56) References Cited

OTHER PUBLICATIONS

Chang, T.-C. et al., "Widespread MicroRNA Repression by Myc Contributes to Tumorigenesis," Nat Genet., Jan. 2008, pp. 43-50, vol. 40, No. 1.
Chen, C.-Z. et al., "MicroRNAs as Regulators of Mammalian Hematopoiesis," Seminars in Immunology, 2005, pp. 155-165, vol. 17.
Cheng, A. M. et al., "Antisense Inhibition of Human miRNAs and Indications for an Involvement of miRNA in Cell Growth and Apoptosis," Nucleic Acids Research, 2005, pp. 1290-1297, vol. 33, No. 4.
Chinese Office Action, Application No. 200780040146.7 dated May 25, 2011.
Ciafre, S. A. et al., "Extensive Modulation of a Set of MicroRNAs in Primary Glioblastoma," Biochemical and Biophysical Research Communications, 2005, pp. 1351-1358, vol. 334.
Cimmino, A. et al., "miR-15 and miR-16 Induce Apoptosis by Targeting BCL2," PNAS, Sep. 2005, pp. 13944-13949, vol. 102, No. 39.
Cimmino, A. et al., Corrections to "miR-15 and miR-16 Induce Apoptosis by Targeting BCL2," PNAS, Feb. 2006, pp. 2464-2465, vol. 103, No. 7.
Costinean, S. et al., "Pre-B Cell Proliferation and Lymphoblastic Leukemia/ High-Grade Lymphoma in Eµ-miR155 Transgenic Mice," PNAS, May 2006, pp. 7024-7029, vol. 103, No. 18.
Croce, C. M. et al., "miRNAs, Cancer, and Stem Cell Division," Cell, 2005, pp. 6-7, vol. 36.
Croce, C. M. et al., "Role of FHIT in Human Cancer," Journal of Clinical Oncology, May 1999, pp. 1618-1624, vol. 17, No. 5.
Croce, C. M., "Causes and Consequences of MicroRNA Dysregulation in Cancer," Nature Reviews Genetics, Oct. 2009, pp. 704-714, vol. 10.
Croce, C. M., "Oncogenes and Cancer," The New England Journal of Medicine, Jan. 2008, pp. 502-511, vol. 358, No. 5.
Cui, S. et al., "MicroRNAs that Underlie Ovarian Cancer Development and Response to Chemotherapy," 98th AACR Annual Meeting, Apr. 14-18, 2007, Los Angeles, CA.
Dalmay, T. et al., "MicroRNAs and the Hallmarks of Cancer," Oncogene, 2006, pp. 6170-6175, vol. 25.
Davies, B.R. et al., "AZD6244 (ARRY-142886), a Potent Inhibitor of Mitogen-Activated Protein Kinase/Extracellular Signal-Regulated Kinase Kinase 1/2 Kinases: Mechanism of Action in vivo, Pharmacokinetic/Pharmacodynamic Relationship, and Potential for Combination in Preclinical Needs," Mol. Cancer Ther., Aug. 2007, vol. 6, No. 8, pp. 2209-2219.
Davies, F. E. et al., "Insights into the Multistep Transformation of MGUS to Myeloma Using Microarray Expression Analysis," Blood, Dec. 2003, pp. 4504-4511, vol. 102, No. 13.
Dohner, H. et al., "Genomic Aberrations and Survival in Chronic Lymphocytic Leukemia," The New England Journal of Medicine, Dec. 2000, pp. 1910-1916, vol. 343, No. 26.
Druck, etal., "FHIT," Atlas of Genetics and Cytogenetics in Oncology and Haematology, 2007, pp. 171-178, vol. 2.
Eis, P. S. et al., "Accumulation of miR-155 and BIC RNA in Human B Cell Lymphomas," PNAS, Mar. 2005, pp. 3627-3632, vol. 102, No. 10.
EP Search Report, Application No. 08782609.5 dated Oct. 28, 2010.
Esquela-Kerscher, A. et al., "Oncomirs—MicroRNAs with a Role in Cancer," Nature Reviews:Cancer, Apr. 2006, pp. 259-269, vol. 6.
European Communication Pursuant to Article 94(3) EPC, Application No. 07810382.7, dated Dec. 8, 2010.
European Communication Pursuant to Article 94(3) EPC, Application No. 07867402.5, dated Jan. 5, 2011.
European Patent Application, EP 1795203 A2, Croce et al., Application No. 06010581.4, filed Feb. 7, 1997, published Jun. 13, 2007.
European Search Report, Application No. 08798444.9-2402, PCT/US2008/073964, dated Dec. 16, 2010.
European Search Report, Application No. 08799295.4-2402, PCT/US2008/075565, dated Nov. 9, 2010.
European Search Report, Application No. 06800599.0 dated Oct. 19, 2009.
European Search Report, Application No. 06814375.9 dated Oct. 8, 2009.
European Search Report, Application No. 06825457.2 dated Sep. 16, 2009.
European Search Report, Application No. 07716208.9 dated Nov. 10, 2009.
European Search Report, Application No. 07717734.3 dated Nov. 9, 2009.
European Search Report, Application No. 07717903.4 dated Oct. 23, 2009.
European Search Report, Application No. 07753450.1 dated Jan. 12, 2009.
European Search Report, Application No. 07810382.7 dated Sep. 14, 2009.
European Search Report, Application No. 07867402.5 dated Mar. 16, 2010.
European Search Report, Application No. 07872618.9 dated Jul. 5, 2010.
European Search Report, Application No. 08767439.6 dated May 12, 2010.
European Search Report, Application No. 08768266.2 dated Jul. 1, 2010.
European Search Report, Application No. 08796821.0 dated Aug. 4, 2010.
European Search Report, Application No. 08841700.1 dated Jun. 2, 2010.
European Supplementary Search Report, Application No. 09715064.3 dated May 24, 2011.
Fabbri, M. et al., "MicroRNA-29 Family Reverts Aberrant Methylation in Lung Cancer by Targeting DNA Methyltransferases 3A and 3B," PNAS, Oct. 2007, pp. 15805-15810, vol. 104, No. 40.
Fabbri, M. et al., "MicroRNAs," The Cancer Journal, Jan./Feb. 2008, pp. 1-6, vol. 14, No. 1.
Fabbri, M. et al., "WWOX Gene Restoration Prevents Lung Cancer Growth In Vitro and In Vivo," PNAS, Oct. 2005, pp. 15611-15616, vol. 102, No. 43.
Felli, N. et al., "MicroRNAs 221 and 222 Inhibit Normal Erythropoiesis and Erythroleukemic Cell Growth via Kit Receptor Down-Modulation," PNAS, Dec. 2005, pp. 18081-18086, vol. 102, No. 50.
Flavin, RJ et al., "MicroRNA Gene Expression Profiling in Human Ovarian and Primary Peritoneal Serous Carcinomas" USCAP 96th Annual Meeting, Abstract #897, San Diego, CA, Mar. 2007.
Fong, Y. et al., "Muir-Torre-Like Syndrome in FHIT-Deficient Mice," PNAS, Apr. 2000, pp. 4742-4747, vol. 97, No. 9.
Ford, L.P., "A MicroRNA Expression Signature of Human Solid Tumors Defines Cancer Gene Targets," Leukemia Research, 2006, pp. 511-513, vol. 30.
Fox, T. et al., "A Single Amino Acid Substitution Makes ERK2 Susceptible to Pyridinyl Imidazole Inhibitors of p38 MAP Kinase," Protein Science, 1998, pp. 2249-2255, vol. 7.
Garofalo, M. et al., "miR-221&222 Regulate TRAIL Resistance and Enhance Tumorigenicity through PTEN and TIMP3 Downregulation," Cancer Cell, Dec. 2009, pp. 498-509, vol. 16.
Garzon, et al., "MicroRNA 29b Functions in Acute Myeloid Leukemia," Prepublished Online, www.bloodjournal.org, Oct. 2009, doi:10.1182/blood-2009-03-211938, pp. 5331-5341, vol. 114.
Garzon, R. et al., "MicroRNA Expression and Function in Cancer," Trends in Molecular Medicine, Oct. 2006, pp. 580-587, vol. 12, No. 12.
Garzon, R. et al., "MicroRNA Fingerprints During Human Megakaryocytopoiesis," PNAS, Mar. 2006, pp. 5078-5083, vol. 103, No. 13.
Garzon, R. et al., "MicroRNA Signatures Associated with Cytogenetics and Outcome in Acute Myeloid Leukemia," ASH Annual Meeting Abstracts, Nov. 2006, Abstract #151, Part 1, p. 498, vol. 108, Issue 11.
Garzon, R. et al., "MicroRNA Signatures Associated with Cytogenetics and Prognosis in Acute Myeloid Leukemia," Blood, Published Online Jan. 2008, DOI: 10.1182/blood-2007-07-098749.
Godlewski, J. et al., "Targeting of the Bmi-1 Oncogene/Stem Cell Renewal Factor by MicroRNA-128 Inhibits Glioma Proliferation and Self-Renewal," Cancer Research, Nov. 2008, pp. 9125-9130, vol. 68, No. 22.

(56) References Cited

OTHER PUBLICATIONS

Gourley, C. et al., "WWOX Gene Expression Abolishes Ovarian Cancer Tumorigenicity In Vivo and Decreases Attachment to Fibronectin via Integrin α3," Cancer Research, Jun. 2009, pp. 4835-4842, vol. 69, No. 11.
Griffiths-Jones, S. et al., "miRBase: MicroRNA Sequences, Targets and Gene Nomenclature," Nucleic Acids Research, 2006, pp. D140-D144, vol. 34.
Grifffhs-Jones, S. et al., "miRBase: Tools for MicroRNA Genomics," Nucleic Acids Research, 2008, pp. D154-D157, vol. 36.
Griffiths-Jones, S., "The MicroRNA Registry," Nucleic Acids Research, 2004, pp. D109-D111, vol. 32.
Guimaraes-Sternberg, C. et al., "MicroRNA Modulation of Megakaryoblast Fate Involves Cholinergic Signaling," Leukemia Research, 2006, pp. 583-595, vol. 30.
Guweidhi, A. et al. "Enhanced Expression of 14-3-3sigma in Pancreatic Cancer and its Role in Cell Cycle Regulation and Apoptosis," Carcinogenesis, 2004, pp. 1575-1585, vol. 25, No. 9.
Havelange, V. et al., "MicroRNAs: New Players in Acute Myeloid Leukemia," British Journal of Cancer, 2009, pp. 743-748, vol. 101.
Hayashita, Y. et al., "A Polycistronic MicroRNA Cluster, miR-17-92, is Overexpressed in Human Lung Cancers and Enhances Cell Proliferation," Cancer Research, Nov. 2005, pp. 9628-9632, vol. 65, No. 21.
He, X. et al., "MicroRNA and Esophageal Carcinoma," Journal of Nanjing Medical University, 2007, pp. 201-206, vol. 21, No. 4.
Herling, et al., "TCL1 Shows a Regulated Expression Pattern in Chronic Lymphocytic Leukemia that Correlates with Molecular Subtypes and Proliferative State," Leukemia, Feb. 2006, pp. 280-285, vol. 20, No. 2.
Hiromura, M. et al., "Identification of Nerve Growth Factor-Responsive Element of the TCL1 Promoter as a Novel Negative Regulatory Element," The Journal of Biological Chemistry, Sep. 2006, pp. 27753-27764, vol. 281, No. 38.
Huang, Y.-S. et al., "Microarray Analysis of MicroRNA Expression in Hepatocellular Carcinoma and Non-Tumorous Tissues Without Viral Hepatitis," Journal of Gastroenterology and Hepatology, 2008, pp. 87-94, vol. 23.
Iliopoulos, D. et al., "Fragile Genes as Biomarkers: Epigenetic Control of WWOX and FHIT in Lung, Breast and Bladder Cancer," Oncogene, 2005, pp. 1625-1633, vol. 24.
Iliopoulos, D. et al., "Inhibition of Breast Cancer Growth InVitro and In Vivo: Effect of Restoration of WWOX Expression," Clin. Cancer Research, Jan. 2007, pp. 268-274, vol. 13, No. 1.
Iorio, M. V. et al., "MicroRNA Gene Expression Deregulation in Human Breast Cancer," Cancer Research, Aug. 2005, pp. 7065-7070, vol. 65, No. 16.
Iorio, M. V. et al., "MicroRNA Signatures in Human Ovarian Cancer," Cancer Research, Sep. 2007, pp. 8699-8707, vol. 67, No. 18.
Ivanovska, I. et al., "MicroRNAs in the miR-106b Family Regulate p21/CDKN1A and Promote Cell Cycle Progression," Molecular and Cellular Biology, Apr. 2008, pp. 2167-2174, vol. 28, No. 7.
Jansen, A. P. et al., "Epidermal Expression of the Translation Inhibitor Programmed Cell Death 4 Suppresses Tumorigenesis," Cancer Research, Jul. 2005, pp. 6034-6041, vol. 65, No. 14.
Ji, J. et al., "MicroRNA Expression, Survival, and Response to Interferon in Liver Cancer," The New England Journal of Medicine, Oct. 2009, pp. 1437-1447, vol. 361, No. 15.
Ji, J. et al., "New Kids on the Block: Diagnostic and Prognostic MicroRNAs in Hepatocellular Carcinoma," Cancer Biology & Therapy, Aug. 2009, pp. 1-8, vol. 8, No. 16.
Ji, L. et al., "Induction of Apoptosis and Inhibition of Tumorigenicity and Tumor Growth by Adenovirus Vector-Mediated Fragile Histidine Triad (FHIT) Gene Overexpression," Cancer Research, Jul. 1999, pp. 3333-3339, vol. 59.
Jiang, J. et al., "Association of MicroRNA Expression in Hepatocellular Carcinomas with Hepatitis Infection, Cirrhosis, and Patient Survival," Clin Cancer Research, Jan. 2008, pp. 419-427, vol. 14, No. 2.
Jiang, J. et al., "Real-Time Expression Profiling of MicroRNA Precursors in Human Cancer Cell Lines," Nucleic Acids Research, 2005, pp. 5394-5403, vol. 33, No. 17.
John, B. et al., "Human MicroRNA Targets," PLOS Biology, Nov. 2004, pp. 1862-1879, vol. 2, Issue 11.
Johnson, S. M. et al., "RAS is Regulated by the let-7 MicroRNA Family," Cell, Mar. 2005, pp. 635-647, vol. 120.
Johnson, S. M. et al., "RAS is Regulated by the let-7 MicroRNA Family," Supplemental Data, Cell, Mar. 2005, pp. 635-647, vol. 120.
Kawasaki, H. et al., "MicroRNA-196 Inhibits HOXB8 Expression in Myeloid Differentiation of HL60 Cells," Nucleic Acids Symposium Series, 2004, pp. 211-212, No. 48.
Kelly, L.M. et al., "CT53518, A Novel Selective FLT3 Antagonist for the Treatment of Acute Myelogenous Leukemia (AML)," Cancer Cell, Jun. 2002, pp. 421-432, vol. 1.
Kim, H. et al., "Elevated mRNA Levels of DNA Methyltransferase-1 as an Independent Prognostic Factor in Primary Nonsmall Cell Lung Cancer," Cancer, Sep. 2006, pp. 1042-1049, vol. 107, No. 5.
Kotoula, V. et al., "In Situ Detection of MicroRNAs 146b, 221 and 222 in Human Carcinoma Tissues Reveals Tumor-Type Specific Expression Patterns," In: Proceedings of the 98th Annual Meeting of the American Association for Cancer Research, Apr. 14-18, 2007, Los Angeles, CA: AACR, 2007, 2 pages, Abstract No. 1780.
Koturbash, I. et al., "Role of Epigenetic Effectors in Maintenance of the Long-Term Persistent Bystander Effect in Spleen In Vivo," Carcinogenesis, 2007, pp. 1831-1838, vol. 28, No. 8.
Kozomara, A. et al., "miRBase: Integrating MicroRNA Annotation and Deep-Sequencing Data," Nucleic Acids Research, 2011, pp. D152-D157, vol. 39.
Krek, A. et al., "Combinatorial MicroRNA Target Predictions," Nature Genetics, May 2005, pp. 495-500, vol. 37, No. 5.
Kulshreshtha, R. et al., "A MicroRNA Signature of Hypoxia," Molecular and Cellular Biology, Mar. 2007, pp. 1859-1867, vol. 27, No. 5.
Kuroki, et al., "Genetic Alterations of the Tumor Suppressor Gene WWOX in Esophageal Squamous Cell Carcinoma," Cancer Research, Apr. 2002, pp. 2258-2260, vol. 62.
Kutay, H. et al., "Downregulation of miR-122 in the Rodent and Human Hepatocellular Carcinomas," Journal of Cellular Biochemistry, 2006, pp. 671-678, vol. 99.
Lagos-Quintana, M. et al., "Identification of Tissue-Specific MicroRNAs from Mouse," Current Biology, Apr. 2002, pp. 735-739, vol. 12.
Lagos-Quintana, M. et al., "New MicroRNAs From Mouse to Human," RNA, 2003, pp. 175-179, vol. 9, No. 2.
Landgraf, P. et al., "A Mammalian MicroRNA Expression Atlas Based on Small RNA Library Sequencing," Cell, Jun. 2007, pp. 1401-1414, vol. 129.
Landi, M. T. et al., "Gene Expression Signature of Cigarette Smoking and Its Role in Lung Adenocarcinoma Development and Survival," PLOS One, Feb. 2008, pp. 1-8, vol. 3, Issue 2.
Lanza, G. et al., "mRNA/microRNA Gene Expression Profile in Microsatellite Unstable Colorectal Cancer," Molecular Cancer, 2007, pp. 1-11, vol. 6, No. 54.
Lee, E. J. et al., "Expression Profiling Identifies MicroRNA Signature in Pancreatic Cancer," Int. J. Cancer, 2006, pp. 1046-1054, vol. 120.
Lewis, B. P. et al., "Prediction of Mammalian MicroRNA Targets," Cell, Dec. 2003, pp. 787-798, vol. 115.
Li, S.-C. et al., "Bioinformatic Discovery of MicroRNA Precursors from Human ESTs and Introns," BMC Genomics, 2006, vol. 7.
Lin, R.-K. et al., "Alteration of DNA Methyltransferases Contributes to 5'CpG Methylation and Poor Prognosis in Lung Cancer," Lung Cancer, 2007, pp. 205-213, vol. 55.
Lipp, E., "MicroRNAs Inform Cancer Research: Alterations in the Expression of miRNA Genes Contribute to Pathogenesis on Broad Basis," Genetic Engineering & Biotechnology News, Dec. 2009, pp. 38-39, genengnews.com.
Liu, C.-G. et al., "An Oligonucleotide Microchip for Genome-Wide MicroRNA Profiling in Human and Mouse Tissues," PNAS, Jun. 2004, pp. 9740-9744, vol. 101, No. 26.

(56) References Cited

OTHER PUBLICATIONS

Lu, J. et al., "MicroRNA Expression Profiles Classify Human Cancers," Nature, Jun. 2005, pp. 834-838, vol. 435, Supplementary Information.
Lu, J. et al., "MicroRNA Expression Profiles Classify Human Cancers," Nature, Jun. 2005, pp. 834-838, vol. 435.
Lujambio, A. et al., "A MicroRNA DNA Methylation Signature for Human Cancer Metastasis," PNAS, Sep. 2008, pp. 13556-13561, vol. 105, No. 36.
Ma, G. et al., "Expression of Programmed Cell Death 4 and Its Clinicopathological Significance in Human Pancreatic Cancer," Department of General Surgery, the First Affiliated Hospital, China Medical University, Oct. 2005, pp. 597-600.
Mack, G. S., "MicroRNA Gets Down to Business," Nature Biotechnology, Jun. 2007, pp. 631-638, vol. 25, No. 6.
Marchetti, A. et al., "EGFR Mutations in Non-Small-Cell Lung Cancer: Analysis of a Large Series of Cases and Development of a Rapid and Sensitive Method for Diagnostic Screening with Potential Implications on Pharmacologic Treatment," Journal of Clinical Oncology, Feb. 2005, pp. 857-865, vol. 23, No. 4.
Marcucci, et al., "MicroRNA Expression in Cytogenetically Normal Acute Myeloid Leukemia," NEJM, May 2008, pp. 1919-1928, vol. 358, No. 18.
Mattie, M. D. et al., "Optimized High-Throughput MicroRNA Expression Profiling Provides Novel Biomarker Assessment of Clinical Prostate and Breast Cancer Biopsies," Molecular Cancer, Jun. 2006, 14 pages, vol. 5, No. 24.
McManus, M. T., "MicroRNAs and Cancer," Seminars in Cancer Biology, 2003, pp. 253-258, vol. 13.
Medina, P.P. et al., "OncomiR Addiction in an In Vivo Model of MicroRNA-21-Induced Pre-B-Cell Lymphoma," Nature Letters, Sep. 2010, pp. 86-91, vol. 467.
Medina, P.P., "OncomiR Addicton in an in vivo Model of MicroRNA-21-Induced Pre-B-Cell Lymphoma," Supplementary Information, Sep. 2010, p. 1-22.
Megraw, M. et al., "miRGen: A Database for the Study of Animal MicroRNA Genomic Organization and Function," Nucleic Acids Research, 2007, pp. D149-D155, vol. 35.
Meng, F. et al., "Involvement of Human MicroRNA in Growth and Response to Chemotherapy in Human Cholangiocarcinoma Cell Lines," Gastroenterology, 2006, pp. 2113-2129, vol. 130.
Mi, S. et al., "MicroRNA Expression Signatures Accurately Discriminate Acute Lymphoblastic Leukemia from Acute Myeloid Leukemia," PNAS, Dec. 2007, pp. 19971-19976, vol. 104, No. 50.
Michael, M. Z. et al., "Reduced Accumulation of Specific MicroRNAs in Colorectal Neoplasia," Molecular Cancer Research, Oct. 2003, pp. 882-891, vol. 1.
Miller, M. K. et al., "Concurrent Chronic Lymphocytic Leukemia Cutis and Acute Myelogenous Leukemia Cutis in a Patient with Untreated CLL," The American Journal of Dermatopathology, 2001, pp. 334-340, vol. 23, No. 4.
Mitchell, P. S. et al., "Circulating MicroRNAs as Stable Blood-Based Markers for Cancer Detection," PNAS, Jul. 2008, pp. 10513-10518, vol. 105, No. 30.
Mitrovic, T. et al., "Cancer Gene Therapy," Arch. Oncology, 2005, pp. 23-26, vol. 13, No. 1.
Mountzios, G. et al., "Mechanisms of Disease: Signal Transduction in Lung Carcinogenesis—A Comparison of Smokers and Never-Smokers," Nature Clinical Practice Oncology, Oct. 2008, pp. 610-618, vol. 5, No. 10.
Murakami, Y. et al., "Comprehensive Analysis of MicroRNA Expression Patterns in Hepatocellular Carcinoma and Non-Tumorous Tissues," Oncogene, 2006 pp. 2537-2545, vol. 25., published online Dec. 5, 2005.
Naegeli, K. et al., "Novel Mechanisms of Ovarian Cancer Growth Inhibition, via MicroRNA Downregulation and Oxidative Damage, by a Ratioanlly Designed Histone Deacetylase Inhibitor," Abstract #2475, 98th ACCR Annual Meeting, Apr. 14-18, 2007, Los Angeles, CA.
Nakanishi, H. et al., "ALL1 Fusion Proteins Induce Deregulation of EphA7 and ERK Phosphorylation in Human Acute Leukemias," PNAS, Sep. 2007, pp. 14442-14447, vol. 104, No. 36.
Negrini, M. et al., "MicroRNAs in Human Cancer: From Research to Therapy," Journal of Cell Science, Apr. 2007, pp. 1833-1840, vol. 120.
Nicoloso, M.S. et al., "MicroRNAsz—The Micro Steering Wheel of Tumour Metastases," Nature Reviews: Cancer, Apr. 2009, pp. 293-302, vol. 9.
Notice of Allowance and Fees Due in U.S. Appl. No. 12/160,064, filed Jul. 3, 2008, mailing date Nov. 20, 2009.
Notice of Allowance and Fees Due in U.S. Appl. No. 12/298,221, filed Nov. 10, 2008, mailing date Nov. 30, 2009.
Nurden, A.T., "Qualitative Disorders of Platelets and Megakaryocytes," Journal of Thrombosis and Haemostasis, 2005, vol. 3, pp. 1773-1782.
Office Action issued in U.S. Appl. No. 12/083,067, filed Jun. 20, 2008, mailing date Jul. 8, 2010.
Office Action issued in U.S. Appl. No. 12/160,034, filed Jul. 3, 2008, mailing date Jun. 7, 2010.
Office Action issued in U.S. Appl. No. 12/160,061, filed Jul. 3, 2008, mailing date Mar. 12, 2010.
Office Action issued in U.S. Appl. No. 12/160,061, filed Jul. 3, 2008, mailing date Apr. 24, 2009.
Office Action issued in U.S. Appl. No. 12/160,061, filed Jul. 3, 2008, mailing date Oct. 30, 2009.
Office Action issued in U.S. Appl. No. 12/160,064, filed Jul. 3, 2008, mailing date Aug. 10, 2009.
Office Action issued in U.S. Appl. No. 12/293,471, filed Oct. 9, 2008, mailing date Jun. 8, 2010.06140.
Office Action issued in U.S. Appl. No. 12/373,358, filed Feb. 11, 2009, mailing date Aug. 20, 2010.
Office Action issued in U.S. Appl. No. 12/442,018, filed Mar. 27, 2009, mailing date Apr. 15, 2010.
Palamarchuk, A. et al., "Akt Phosphorylates Tcl1 Oncoprotein and Inhibits Its Repressor Activity," Cancer Research, Jun. 2005, pp. 4515-4519, vol. 65, No. 11.
Pawelczyk, T. et al., "Expression in *Escherichia coli* and Simple Purification of Human Fhit Protein," Protein Expr. Purlf., Apr. 2000, pp. 320-326, vol. 18, No. 3.
PCT International Preliminary Report on Patentability, PCT/US/2007/023660 filed Nov. 1, 2007, dated May 5, 2009.
PCT International Preliminary Report on Patentability, PCT/US/2008/072081 filed Aug. 4, 2008, dated Feb. 9, 2010.
PCT International Preliminary Report on Patentability, PCT/US2006/029889 filed Jul. 31, 2006, dated Feb. 5, 2008.
PCT International Preliminary Report on Patentability, PCT/US2006/035100 filed Sep. 11, 2006, dated Mar. 18, 2008.
PCT International Preliminary Report on Patentability, PCT/US2006/038824 filed Oct. 4, 2006, dated Apr. 9, 2008.
PCT International Preliminary Report on Patentability, PCT/US2007/000024 filed Jan. 3, 2007, dated Jul. 8, 2008.
PCT International Preliminary Report on Patentability, PCT/US2007/000103 filed Jan. 3, 2007, dated Jul. 8, 2008.
PCT International Preliminary Report on Patentability, PCT/US2007/000159 filed Jan. 3, 2007, dated Jul. 8, 2008.
PCT International Preliminary Report on Patentability, PCT/US2007/006824 filed Mar. 19, 2007, dated Sep. 23, 2008.
PCT International Preliminary Report on Patentability, PCT/US2007/009910 filed Apr. 24, 2007, dated Oct. 28, 2008.
PCT International Preliminary Report on Patentability, PCT/US2007/015892 filed Jul. 12, 2007, dated Jan. 13, 2009.
PCT International Preliminary Report on Patentability, PCT/US2007/020215 filed Sep. 17, 2007, dated Mar. 24, 2009.
PCT International Preliminary Report on Patentability, PCT/US2008/001157 filed Jan. 29, 2008, dated Aug. 4, 2009.
PCT International Preliminary Report on Patentability, PCT/US2008/005503 filed Apr. 29, 2008, dated Nov. 3, 2009.
PCT International Preliminary Report on Patentability, PCT/US2008/007196 filed Jun. 9, 2008, dated Dec. 11, 2009.
PCT International Preliminary Report on Patentability, PCT/US2008/066870 filed Jun. 13, 2008, dated Dec. 17, 2009.

(56) References Cited

OTHER PUBLICATIONS

PCT International Preliminary Report on Patentability, PCT/US2008/071532 filed Jul. 30, 2008, dated Feb. 2, 2010.
PCT International Preliminary Report on Patentability, PCT/US2008/073964 filed Aug. 22, 2008, dated Feb. 24, 2010.
PCT International Preliminary Report on Patentability, PCT/US2008/075565 filed Sep. 8, 2008, dated Mar. 9, 2010.
PCT International Preliminary Report on Patentability, PCT/US2008/079482 filed Oct. 10, 2008, dated Apr. 13, 2010.
PCT International Preliminary Report on Patentability, PCT/US2008/081294 filed Oct. 27, 2008, dated Apr. 27, 2010.
PCT International Preliminary Report on Patentability, PCT/US2009/035458 filed Feb. 27, 2009, dated Aug. 31, 2010.
PCT International Preliminary Report on Patentability, PCT/US2009/035463 filed Feb. 27, 2009, dated Aug. 31, 2010.
PCT International Preliminary Report on Patentability, PCT/US2009/035470 filed Feb. 27, 2009, dated Aug. 31, 2010.
PCT International Preliminary Report on Patentability, PCT/US2009/035482 filed Feb. 27, 2009, dated Aug. 31, 2010.
PCT International Search Report and the Written Opinion, PCT/US2007/006824 filed Mar. 19, 2007, dated Mar. 3, 2008.
PCT International Search Report and the Written Opinion, PCT/US2006/29889 filed Jul. 31, 2006, dated Jul. 10, 2007.
PCT International Search Report and the Written Opinion, PCT/US2006/35100 filed Sep. 11, 2006, dated Sep. 5, 2007.
PCT International Search Report and the Written Opinion, PCT/US2006/38824 filed Oct. 4, 2006, dated Aug. 9, 2007.
PCT International Search Report and the Written Opinion, PCT/US2007/00024 filed Jan. 3, 2007, dated Nov. 5, 2007.
PCT International Search Report and the Written Opinion, PCT/US2007/00103 filed Jan. 3, 2007, dated Dec. 3, 2007.
PCT International Search Report and the Written Opinion, PCT/US2007/00159 filed Jan. 3, 2007, dated Apr. 11, 2008.
PCT International Search Report and the Written Opinion, PCT/US2007/006824 filed Mar. 19, 2007, dated May 14, 2008.
PCT International Search Report and the Written Opinion, PCT/US2007/09910 filed Apr. 24, 2007, dated Feb. 13, 2008.
PCT International Search Report and the Written Opinion, PCT/US2007/15892 filed Jul. 12, 2007, dated Sep. 30, 2008.
PCT International Search Report and the Written Opinion, PCT/US2007/20215 filed Sep. 17, 2007, dated Jul. 25, 2008.
PCT International Search Report and the Written Opinion, PCT/US2007/23660 filed Nov. 1, 2007, dated Sep. 16, 2008.
PCT International Search Report and the Written Opinion, PCT/US2008/01157 filed Jan. 29, 2008, dated Aug. 7, 2008.
PCT International Search Report and the Written Opinion, PCT/US2008/05503 filed Apr. 29, 2008, dated Sep. 25, 2008.
PCT International Search Report and the Written Opinion, PCT/US2008/07196 filed Jun. 9, 2008, dated Nov. 19, 2008.
PCT International Search Report and the Written Opinion, PCT/US2008/66870 filed Jun. 13, 2008, dated Nov. 10, 2008.
PCT International Search Report and the Written Opinion, PCT/US2008/71532 filed Jul. 30, 2008, dated Apr. 17, 2009.
PCT International Search Report and the Written Opinion, PCT/US2008/72081 filed Aug. 4, 2008, dated Jan. 14, 2009.
PCT International Search Report and the Written Opinion, PCT/US2008/73964 filed Aug. 22, 2008, dated Dec. 24, 2008.
PCT International Search Report and the Written Opinion, PCT/US2008/75565 filed Sep. 8, 2008, dated Dec. 9, 2008.
PCT International Search Report and the Written Opinion, PCT/US2008/79482 filed Oct. 10, 2008, dated Dec. 22, 2008.
PCT International Search Report and the Written Opinion, PCT/US2008/81294 filed Oct. 27, 2008, dated Mar. 26, 2009.
PCT International Search Report and the Written Opinion, PCT/US2008/84821 filed Nov. 26, 2008, dated Feb. 17, 2009.
PCT International Search Report and the Written Opinion, PCT/US2009/35458 filed Feb. 27, 2009, dated Jul. 28, 2009.
PCT International Search Report and the Written Opinion, PCT/US2009/35463 filed Feb. 27, 2009, dated Aug. 13, 2009.
PCT International Search Report and the Written Opinion, PCT/US2009/35470 filed Feb. 27, 2009, dated Jun. 16, 2009.
PCT International Search Report and the Written Opinion, PCT/US2009/35482 filed Feb. 27, 2009, dated Jul. 17, 2009.
PCT International Search Report and the Written Opinion, PCT/US2009/38214 filed Mar. 25, 2009, dated Aug. 14, 2009.
PCT International Search Report and the Written Opinion, PCT/US2009/46999 filed Jun. 11, 2009, dated Nov. 23, 2009.
PCT International Search Report and the Written Opinion, PCT/US2009/53586 filed Aug. 12, 2009, dated Oct. 28, 2009.
PCT International Search Report and the Written Opinion, PCT/US2009/65072 filed Nov. 19, 2009, dated Mar. 3, 2010.
PCT International Search Report and the Written Opinion, PCT/US2010/025173 filed Feb. 24, 2010, dated Jul. 6, 2010.
Pedersen, I. M. et al., "Interferon Modulation of Cellular MicroRNAs as an Antiviral Mechanism," Nature, Oct. 2007, pp. 919-922, vol. 449.
Pekarsky, Y. et al., "Animal Models for Chronic Lymphocytic Leumekia," Journal of Cellular Biochemistry, 2007, pp. 1109-1118, vol. 100.
Pekarsky, Y. et al., "Tcl1 Enhances Akt Kinase Activity and Mediates Its Nuclear Translocation," PNAS, Mar. 2000, pp. 3028-3033, vol. 97, No. 7.
Pekarsky, Y. et al., "Tcl1 Expression in Chronic Lymphocytic Leukemia is Regulated by miR-29 and miR-181," Cancer Research, Dec. 2006, pp. 11590-11593, vol. 66, No. 24.
Pekarsky, Y. et al., "Tcl1 Functions as a Transcriptional Regulator and is Directly Involved in the Pathogenesis of CLL," PNAS, Dec. 2008, pp. 19643-19648, vol. 105, No. 50.
Petrocca, F. et al., "E2F1-Regulated MicroRNAs Impair TGFβ-Dependent Cell-Cycle Arrest and Apoptosis in Gastric Cancer," Cancer Cell, Mar. 2008, pp. 272-286, vol. 13.
Pichiorri, F. et al., "MicroRNAs Regulate Critical Genes Associated with Multiple Myeloma Pathogenesis," PNAS, Sep. 2008, pp. 12885-12890, vol. 105, No. 35.
Pineau, P. et al., "miR-221 Overexpression Contributes to Liver Tumorigenesis," PNAS, Jan. 2010, pp. 264-269, vol. 107, No. 1.
Porkka, K.P. et al., "MicroRNA Expression Profiling in Prostate Cancer," Cancer Research, 2007, pp. 6130-6135, vol. 67, No. 13.
Prueitt, R. L. et al., "Expression of MicroRNAs and Protein-Coding Genes Associated with Perineural Invasion in Prostate Cancer," The Prostate, 2008, pp. 1152-1164, vol. 68.
Pruitt, K.D. et al., "NCBI Reference Sequence (RefSeq): A Curated Non-Redundant Sequence Database of Genomes, Transcripts and Proteins," Nucleic Acids Research, 2005, pp. D501-D504, vol. 33.
Qin, H. R. et al., "A Role for the WWOX Gene in Prostate Cancer," Cancer Research, Jul. 2006, pp. 6477-6481, vol. 66, No. 13.
Ramkissoon, S. H, et al., "Hematopoietic-Specific MicroRNA Expression in Human Cells," Leukemia Research, 2006, pp. 643-647, vol. 30.
Roldo, C. et al., "MicroRNA Expression Abnormalities in Pancreatic Endocrine and Acinar Tumors Are Associated With Distinctive Pathologic Feature and Clinical Behavior," Journal of Clinical Oncology, Oct. 2006, pp. 4677-4684, vol. 24, No. 29.
Rozovskaia, T. et al., "Expression Profiles of Acute Lymphoblastic and Myeloblastic Leukemias with ALL-1 Rearrangements," PNAS, Jun. 2003, pp. 7853-7858, vol. 100, No. 13.
Saini, H. K. et al., "Annotation of Mammalian Primary MicroRNAs," BMC Genomics, 2008, vol. 9.
Santanam, U. et al., "Chronic Lymphocytic Leukemia Modeled in Mouse by Targeted miR-29 Expression," PNAS, Jul. 2010, pp. 12210-12215, vol. 107, No. 27.
Sasaki, Y.T.F. et al., "Coordinated Expression of ncRNAs and HOX mRNAs in the Human HOXA Locus," Biochemical and Biophysical Communications, 2007, pp. 724-730, vol. 357.
Schetter, A. J. et al., "MicroRNA Expression Profiles Associated With Prognosis and Therapeutic Outcome in Colon Adenocarcinoma," JAMA, Jan. 2008, pp. 425-436, vol. 299, No. 4.
Schetter, A.J. et al., "Association of Inflammation-Related and MicroRNA Gene Expression with Cancer Specific Mortality of Colon Adenocarcinoma," Clin. Cancer Res., Sep. 2009, pp. 5878-5887, vol. 15, No. 18.

(56) References Cited

OTHER PUBLICATIONS

Schmittgen, T. D. et al., "A High-Throughput Method to Monitor the Expression of MicroRNA Precursors," Nucleic Acids Research, Feb. 2004, vol. 32, No. 4.

Seike, M. et al., "MiR-21 is an EGFR-Regulated Anti-Apoptotic Factor in Lung Cancer in Never-Smokers," PNAS, Jul. 2009, pp. 12085-12090. vol. 106, No. 29.

Seike, M. et al., "MiR-21 is an EGFR-Regulated Anti-Apoptotic Factor in Lung Cancer in Never-Smokers," Supporting Information, PNAS, Jul. 2009, pp. 12085-12090. vol. 106, No. 29.

Seike, M., "MicroRNA Expression Profiles in Lung Cancer Cooperated with Drug Sensitivity to EGFR Tyrosine Kinase Inhibitor," J. Nippon Med. School, 2009, pp. 275-276, vol. 76, No. 5.

Seth, P., "Vector-Mediated Cancer Gene Therapy," Cancer Biology & Therapy, May 2005, pp. 512-517, vol. 4, Issue 5.

Sevinsky, J. R. et al., "Extracellular Signal-Regulated Kinase Induces the Megakaryocyte GPIIb/CD41 Gene Through MafB/Kreisler," Molecular and Cellular Biology, May 2004, pp. 4534-4545, vol. 24, No. 10.

Sharma, S. et al., "Development of Inhalational Agents for Oncologic Use," Journal of Clinical Oncology, Mar. 2001, Abstract, vol. 19, Issue 6.

Shen, H, et al., "A Novel Polymorphism in Human Cytosine DNA-Methyltransferase-3B Promoter is Associated with an Increased Risk of Lung Cancer," Cancer Research, Sep. 2002, pp. 4992-4995, vol. 62.

Slack, F.J., "Big Roles for Small RNAs," Nature, Feb. 2010, p. 616, vol. 463.

State Intellectual Property Office of the People's Republic of China, Notification of the First Office Action, Application No. 200780005791.5, dated Mar. 24, 2011.

Suarez-Saiz, F.J. et al., "MicroRNA Expression Profiling in Acute Myelogenous Leukemia," Canada Blood, Nov. 2004, Abstract #1131, p. 320A.

Taccioli, C. et al., "Ucbase & miRfunc: A Database of Ultraconserved Sequences and MicroRNA Function," Nucleic Acids Research, 2009, pp. D41-D48, vol. 37.

Takamizawa, J. et al., "Reduced Expression of the let-7 MicroRNAs in Human Lung Cancers in Association with Shortened Postoperative Survival," Cancer Research, Jun. 2004, pp. 3753-3756, vol. 64.

Tang, X. et al., "A Simple Array Platform for MicroRNA Analysis and Its Application in Mouse Tissues," RNA, Aug. 2007, pp. 1-20, vol. 13.

Thomson, J. M. et al., "A Custom Microarray Platform for Analysis of MicroRNA Gene Expression," Nature Methods, Oct. 2004, pp. 1-7, vol. 1, No. 1.

Thorgeirsson, S. S. et al., "Functional Genomics of Hepatocellular Carcinoma," Hepatology, Feb. 2006, pp. S145-S150, vol. 43, No. 2, Suppl. 1.

Tockman, M. S. et al., "Considerations in Bringing a Cancer Biomarker to Clinical Application," Cancer Research, May 1992, pp. 2711s-2718s, vol. 52.

Trapasso, F. et al., "Fhit Interaction with Ferredoxin Reductase Triggers Generation of Reactive Oxygen Species and Apoptosis of Cancer Cells," Journal of Biological Chemistry, May 2008, pp. 13736-13744, vol. 283, No. 20.

Tricoli, J. V. et al., "MicroRNA: Potential for Cancer Detection, Diagnosis, and Prognosis," Cancer Research, May 2007, pp. 4553-4555, vol. 67, No. 10.

Ueda, T. et al., "Relation Between MicroRNA Expression and Progression and Prognosis of Gastric Cancer: A MicroRNA Expression Analysis," Published Online; www.thelancet.com/oncology, Dec. 2009, DOI:10.1016/S1470-2045(09)70343-2.

Valeri, N. et al., "Epigenetics, miRNAs, and Human Cancer: A New Chapter in Human Gene Regulation," Mamm Genome, Aug. 2009, pp. 573-580, vol. 20.

Valeri, N. et al., "Modulation of Mismatch Repair and Genomic Stability by miR-155," PNAS, Apr. 2010, pp. 6982-6987, vol. 107, No. 15.

Varnholt, H. et al., "MicroRNA Gene Expression Profile of Hepatitis C Virus-Associated Hepatocellular Carcinoma," Hepatology, Apr. 2008, pp. 1223-1232, Vo. 47, No. 4.

Virgilio, L. et al., "Identification of the TCL1 Gene Involved in T-Call Malignancies," Proc. Natl. Acad. Sci., Dec. 1994, pp. 12530-12534, vol. 91.

Visone, R. et al., "MiRNAs and Cancer," The American Journal of Pathology, Apr. 2009, pp. 1131-1138, vol. 174, No. 4.

Volinia, et al., "Reprogramming of MirRNA Networks in Cancer and Leukemia," Genome Research, 2010, pp. 589-599, vol. 20.

Volinia, S. et al., "A MicroRNA Expression Signature of Human Solid Tumors Defines Cancer Gene Targets," PNAS, Feb. 2006, pp. 2257-2261, vol. 103, No. 7.

Wang, E. et al., "Ontogeny and Oncogenesis Balance the Transcriptional Profile of Renal Cell Cancer," Cancer Research, Oct. 2004, pp. 7279-7287, vol. 64.

Wang, X. et al., "Association Between CpG Island Methylation of the WWOX Gene and Its Expression in Breast Cancers," Tumor Biology, Feb. 2009, pp. 8-14, vol. 30.

Weidhaas, J., "Using MicroRNAs to Understand Cancer Biology," Published Online Dec. 21, 2009, DOI: 10.1016/S1470-2045(09)70386-9.

Wijermans, P.W., "Low Dose Azanucleosidesfor High Risk (s) MDS and AML," Haematologica Reports,Nov. 2006, pp. 74-76. vol. 2, Issue, 15.

Yamashita, T. et al., "Activation of Hepatic Stem Cell Marker EpCAM by Wnt-β-Catenin Signaling in Hepatocellular Carcinoma," Cancer Research, Nov. 2007, pp. 10831-10839, vol. 67, No. 22.

Yamashita, T. et al., "EpCAM and α-Fetoprotein Expression Defines Novel Prognostic Subtypes of Hepatocellular Carcinoma," Cancer Research, Mar. 2008, pp. 1451-1461, vol. 68, No. 5.

Yanaihara, N. et al., "Unique MicroRNA Molecular Profiles in Lung Cancer Diagnosis and Prognosis," Cancer Cell, Mar. 2006, pp. 189-198, vol. 9.

Yang, J. et al., "Analysis of Sequence Variations in 59 MicroRNAs in Hepatocellular Carcinomas," Mutation Research, Aug. 2008, pp. 205-209, vol. 638.

Yendamuri, S. et al., "WW Domain Containing Oxidoreductase Gene Expression is Altered in Non-Small Cell Lung Cancer," Cancer Research, Feb. 2003, pp. 878-881, vol. 63.

Yoon, S. et al., "Prediction of Regulatory Modules Comprising MicroRNAs and Target Genes," Bioinformatics Genes and Genomes, 2005. pp. ii93-ii100, vol. 21, Suppl. 2.

Yu, L.-G. et al., "Protein Phosphatase 2A, a Negative Regulator of the ERK Signaling Pathway, Is Activated by Tyrosine Phosphorylation of Putative HLA Class II-Associated Protein I (PHAPI)/pp32 in Response to the Antiproliferative Lectin, Jacalin," The Journal of Biological Chemisty, Jul. 2004, pp. 41377-41383, vol. 279, No. 40.

Zeng, Y. et al., "Recognition and Cleavage of Primary MicroRNA Precursors by the Nuclear Processing Enzyme Drosha," The EMBO Journal, 2005, pp. 138-148, vol. 24.

Zhang, L. et al., "Genomic and Epigenetic Alterations Deregulate MicroRNA Expression in Human Epithelial Ovarian Cancer," PNAS, May 2008, pp. 7004-7009, vol. 105, No. 19.

Zhang, L. et al., "MicroRNAs Exhibit High Frequency Genomic Alterations in Human Cancer," PNAS, Jun. 2006, pp. 9136-9141, vol. 103, No. 24.

Zhang, L. et al., Supporting Information, PNAS 2008, pp. 1-11.

Zhang, Z. et al., "Three Biomarkers Identified from Serum Proteomic Analysis for the Detection of Early Stage Ovarian Cancer," Cancer Research, Aug. 2004, pp. 5882-5890, vol. 64.

Zhu, S. et al., "MicroRNA-21 Targets the Tumor Suppressor Gene Tropomyosin 1 (TPM 1)," Journal of Biological Chemistry, May 2007, pp. 14328-14336, vol. 282, No. 19.

Chinese Notification of First Office Action, CN Application No. 200980126520.4 filed Jun. 11, 2009, dated Dec. 4, 2012.

Chinese Notification of Second Office Action, Application No. 200980126520.4 dated Aug. 14, 2013.

* cited by examiner

| Table 1A. Clinical Characteristics of the Subjects ||||
|---|---|---|---|
| Clinical variable | Cohort 1 (n=241) | Cohort 2 (n=135) | p value* |
| Gender | | | |
| Female | 30 | 14 | |
| Male | 211 | 111 | 0.87[a] |
| No data | 0 | 10 | |
| Age-year | | | |
| Median (range) | 50 (13-83) | 50 (20-77) | 0.29[b] |
| Alanine transaminase (ALT) | | | |
| Normal (≤50U/L) | 145 | 107 | |
| Abnormal (>50U/L) | 96 | 16 | <0.001[a] |
| No data | 0 | 12 | |
| HBV | | | |
| Negative | 16 | 6 | |
| Positive | 224 | 118 | 0.64[a] |
| No data | 1 | 11 | |
| Tumor size-cm | | | |
| <=3 | 88 | 46 | |
| >3 | 153 | 78 | 0.91[a] |
| No data | 0 | 11 | |
| Multinodular | | | |
| No | 214 | 107 | |
| Yes | 27 | 17 | 0.50[a] |
| No data | 0 | 11 | |
| Cirrhosis | | | |
| No | 17 | 16 | |
| Yes | 223 | 108 | 0.08[a] |
| No data | 1 | 11 | |
| TNM Stage | | | |
| I | 97 | 81 | |
| II | 90 | 29 | |
| III-IV | 54 | 14 | <0.001[c] |
| No data | 0 | 11 | |
| Alpha fetoprotein (AFP) | | | |
| Negative (≤20ng/ml) | 77 | 49 | |
| Positive (>20ng/ml) | 162 | 75 | 0.20[a] |
| No data | 2 | 11 | |
| Adjuvant Therapy** | | | |
| Yes | 39 | 72 | |
| No | 202 | 63 | <0.001[a] |
| Survival-month | | | |
| Median (range) | >60 (2-67) | 67 (2-82) | 0.89[d] |
| * [a]Fisher's exact test; [b]un-paired t-test; [c]Chi-square test; [d]Log-rank test ||||
| ** Cohort 1: Transcatheter arterial chemoembolization (TACE) (n=34); Chemotherapy (n=3); IFNα (n=1); lymphokine activated killer (LAK) cell therapy (n=1); Cohort 2: IFNα (n=72). ||||

Figure 4A - Table 1

Supplementary Table 1. Clinical Characteristics of Two Independent Clinical Trials

| Clinical variable | IFN Test (Cohort 2) (n=135) | IFN Validation (Cohort 3) (n=79) | p value |
|---|---|---|---|
| Gender | | | |
| Female | 14 | 14 | |
| Male | 111 | 65 | 0.21[a] |
| No data | 10 | 0 | |
| Age-year | | | |
| Median (range) | 50 (20-77) | 52 (24-75) | 0.23[b] |
| Alanine transaminase (ALT) | | | |
| Normal (≤50U/L) | 107 | 44 | |
| Abnormal (>50U/L) | 16 | 35 | <0.001[a] |
| No data | 12 | 0 | |
| HBV | | | |
| Negative | 6 | 9 | |
| Positive | 118 | 70 | 0.10[a] |
| No data | 11 | 0 | |
| Tumor size-cm | | | |
| <=3 | 46 | 22 | |
| >3 | 78 | 57 | 0.22[a] |
| No data | 11 | 0 | |
| Multinodular | | | |
| No | 107 | 63 | |
| Yes | 17 | 16 | 0.25[a] |
| No data | 11 | 0 | |
| Cirrhosis | | | |
| No | 16 | 0 | |
| Yes | 108 | 0 | NA[c] |
| No data | 11 | 79 | |
| TNM Stage | | | |
| I | 81 | 7 | |
| II | 29 | 34 | |
| III-IV | 14 | 38 | <0.001[d] |
| No data | 11 | 0 | |
| Alpha fetoprotein (AFP) | | | |
| Negative (≤20ng/ml) | 49 | 33 | |
| Positive (>20ng/ml) | 75 | 46 | 0.77[a] |
| No data | 11 | 0 | |
| IFNα Therapy | | | |
| Yes | 72 | 39 | |
| No | 63 | 40 | 0.67[a] |
| Survival-month | | | |
| Median (range) | 67 (2-82) | >60 (5-60) | 0.06[e] |

* [a]Fisher's exact test; [b]un-paired test; [c]Not available; [d]Chi-square test; [e]Log-rank test

Figure 4B - Supplemental Table 1

Supplementary Table 2. Clinical Characteristic of Cases Used to Search for Gender-Related microRNAs

| Clinical variable | Female (n=30) Value[a] | Male G1 (n=31) Value | Male G2 (n=31) Value | p value[b] | | |
|---|---|---|---|---|---|---|
| | | | | Female vs Male G1 | Female vs Male G2 | Male G1 vs Male G2 |
| Age-year | | | | | | |
| Median | 52 | 52 | 52 | | | |
| Range | 25-72 | 26-71 | 27-71 | 0.93[c] | 0.93[c] | 1.00[c] |
| ALT[d] | | | | | | |
| Normal | 24 | 20 | 18 | | | |
| Abnormal | 6 | 11 | 13 | 0.26 | 0.10 | 0.80 |
| Tumor size-cm | | | | | | |
| <=3 | 16 | 9 | 10 | | | |
| >3 | 14 | 22 | 21 | 0.07 | 0.12 | 1.00 |
| Multinodular | | | | | | |
| No | 25 | 27 | 26 | | | |
| Yes | 5 | 4 | 5 | 0.73 | 1.00 | 1.00 |
| TNM Stage | | | | | | |
| I | 15 | 14 | 13 | | | |
| II | 11 | 7 | 9 | | | |
| III | 4 | 10 | 9 | 0.18[e] | 0.33[e] | 0.84[e] |
| AFP[f] | | | | | | |
| Negative | 9 | 14 | 6 | | | |
| Positive | 20 | 17 | 25 | 0.30 | 0.38 | 0.06 |
| No data | 1 | 0 | 0 | | | |
| Survival Months | | | | | | |
| Range | 3.0-67.1 | 4.5-67.1 | 2.3-65.4 | 0.31[g] | 0.09[g] | 0.55[g] |

[a] Each value represents the number of patients.
[b] Fisher's exact test
[c] Un-paired t-test
[d] Normal: ≤50 (U/L); Abnormal >50 (U/L)
[e] Chi-square test
[f] Negative: ≤20 (ng/ml); Positive >20 (ng/ml)
[g] Log-rank test

Figure 4C - Supplemental Table 2

| Table 2. Univariate and Multivariate Cox Regression Analysis of miR-26 Expression Levels and Overall Survival in Subjects with HCC[a] |||
|---|---|---|
| Clinical Variable | Hazard Ratio (95% CI[b]) | p-value |
| UNIVARIATE ANALYSIS[c] | | |
| miRNA-26a (Low vs. High) | 2.3 (1.1-5.0) | 0.03 |
| miRNA-26b (Low vs. High) | 2.3 (1.1-4.9) | 0.04 |
| Age | 1.0 (1.0-1.0) | 0.41 |
| Gender (Male vs. Female) | 1.4 (0.6-3.7) | 0.47 |
| AFP (>20ng/ml vs. ≤20ng/ml) | 1.2 (0.6-2.5) | 0.58 |
| Cirrhosis (Yes vs. No) | 0.7 (0.3-1.8) | 0.46 |
| ALT (>50U/L vs. ≤50U/L) | 1.2 (0.5-2.8) | 0.73 |
| Tumor size (>3cm vs. ≤3cm) | 1.2 (0.6-2.4) | 0.56 |
| Tumor encapsulation (No vs. Yes) | 1.3 (0.7-2.7) | 0.39 |
| Multinodular (Yes vs. No) | 1.1 (0.5-2.7) | 0.81 |
| TNM staging (II-III vs. I) | 2.2 (1.2-4.3) | 0.02 |
| | | |
| MULTIVARIATE ANALYSIS[d] for miR-26a | | |
| miRNA-26 (Low vs. High) | 2.2 (1.0-4.7) | 0.05 |
| TNM staging (II-III vs. I) | 1.9 (1.0-3.9) | 0.05 |
| Gender (Male vs. Female) | 1.1 (0.4-2.8) | 0.88 |
| | | |
| MULTIVARIATE ANALYSIS[d] for miR-26b | | |
| miRNA-26 (Low vs High) | 2.2 (1.1-4.9) | 0.04 |
| TNM staging (II-III vs. I) | 2.1 (1.1-4.2) | 0.03 |
| Gender (Male vs. Female) | 1.0 (0.4-2.6) | 0.99 |
| [a]The analysis was performed on control cases (n=60) (cohort 2) dichotomized by miR-26a/b low level group and miR-26a/b high level group; [b]95% CI, 95% confidence interval; [c]Univariate analysis Cox proportional hazards regression; [d]Multivariate analysis, Cox proportional hazards regression; Significant p values (<0.05) are highlighted in bold. |||

Figure 5A - Table 2

| Table 3. Univariate and Multivariate Cox Regression Analysis of Interferon Therapy and Overall Cancer Survival in Subjects with Low miR-26 Expression[a] | | |
|---|---|---|
| Clinical Variable | Hazard Ratio (95% CI[b]) | p-value |
| Cases with low miR-26a expression (n=59) | | |
| UNIVARIATE ANALYSIS[c] | | |
|   Treatment (IFN vs Control) | 0.2 (0.1-0.6) | 0.003 |
|   Age | 1.0 (1.0-1.0) | 0.64 |
|   Gender (Male vs Female) | 1.3 (0.4-3.7) | 0.65 |
|   AFP (>20ng/ml vs ≤20ng/ml) | 1.8 (0.8-4.1) | 0.15 |
|   Cirrhosis (Yes vs No) | 0.7 (0.3-2.1) | 0.57 |
|   ALT (>50U/L vs ≤50U/L) | 1.1 (0.4-3.0) | 0.79 |
|   Tumor size (>3cm vs ≤3cm) | 1.7 (0.8-3.6) | 0.15 |
|   Tumor encapsulation (No vs Yes) | 1.8 (0.9-3.6) | 0.12 |
|   Multinodular (Yes vs No) | 0.9 (0.3-2.3) | 0.82 |
|   TNM staging (II-III vs I) | 2.7 (1.3-5.5) | 0.005 |
| | | |
| MULTIVARIATE ANALYSIS[d] | | |
|   Treatment (IFN vs Control) | 0.3 (0.1-0.7) | 0.005 |
|   TNM staging (II-III vs I) | 2.4 (1.2-4.9) | 0.02 |
|   Gender (Male vs Female) | 1.4 (0.5-4.0) | 0.55 |
| | | |
| Cases with low miR-26b expression (n=58) | | |
| UNIVARIATE ANALYSIS | | |
|   Treatment (IFN vs Control) | 0.4 (0.2-0.9) | 0.04 |
|   Age | 1.0 (1.0-1.0) | 0.82 |
|   Gender (Male vs Female) | 1.4 (0.4-4.7) | 0.57 |
|   AFP (>20ng/ml vs ≤20ng/ml) | 1.9 (0.9-4.0) | 0.10 |
|   Cirrhosis (Yes vs No) | 0.7 (0.3-1.8) | 0.43 |
|   ALT (>50U/L vs ≤50U/L) | 1.9 (0.8-4.6) | 0.17 |
|   Tumor size (>3cm vs ≤3cm) | 2.0 (1.0-4.3) | 0.06 |
|   Tumor encapsulation (No vs Yes) | 1.6 (0.8-3.1) | 0.20 |
|   Multinodular (Yes vs No) | 1.1 (0.4-2.6) | 0.87 |
|   TNM staging (II-III vs I) | 2.7 (1.4-5.3) | 0.004 |
| | | |
| MULTIVARIATE ANALYSIS | | |
|   Treatment (IFN vs Control) | 0.4 (0.2-0.9) | 0.04 |
|   TNM staging (II-III vs I) | 2.6 (1.3-5.1) | 0.007 |
|   Gender (Male vs Female) | 1.5 (0.5-5.1) | 0.48 |
| [a]The analysis was performed on the cases with low miR-26 expression of cohort2; [b]95% CI, 95% confidence interval; [c]Univariate analysis, Cox proportional hazards regression; [d]Multivariate analysis, Cox proportional hazards regression; Significant p values (<0.05) are highlighted in bold. | | |

Figure 5B - Table 3

Supplemental Table 3. Eight Gender-Related microRNAs

| Gender-miRNA | Genomic Location | Parametric p-value | Permutation p-value | Mean Intensities in Female | Mean Intensities in Male | Expression in Female |
|---|---|---|---|---|---|---|
| Non-HCC | | | | | | |
| miR-321* | - | 0.001 | 0.003 | 4585 | 2618 | up |
| miR-26a-1 | 3p22.3 | 0.01 | 0.01 | 19879 | 14417 | up |
| miR-10b | 2q31.1 | 0.02 | 0.02 | 735 | 535 | up |
| miR-125b-1 | 11q24.1 | 0.02 | 0.02 | 4211 | 2838 | up |
| miR-99b | 19q13.41 | 0.04 | 0.04 | 2628 | 2071 | up |
| miR-325 | Xq21.1 | 0.05 | 0.06 | 1885 | 1146 | up |
| miR-342 | 14q32.2 | 0.04 | 0.03 | 306 | 373 | down |
| HCC | | | | | | |
| miR-129-2 | 11p11.2 | 0.007 | 0.004 | 893 | 1179 | down |

* miR-321 is reported as a fragment of Arg-tRNA.

Figure 6A - Supplemental Table 3

Figure 6B - Table 4:
Top 20 list of gene networks from INGENUITY™ Pathway Analysis

| ID | Genes in Network | Score* | # of Genes | Top Functions |
|---|---|---|---|---|
| 1 | 14-3-3, ACLY, CPOX, CTDP1, Cyclin B, DAXX, DNM1, GAPDH, GML, HK3, HUWE1, IRF5, Jnk dimer, LRDD, MED22, MED28, Ndpk, NELF, NME1, NME2, PDCD2, PIN1, PKMYT1, RNA polymerase II, RPS6KA1, Rsk, SFN, SNCAIP, STRAP, TBXAS1, TP53, TP53BP1, TTC5, ZBTB17, ZNF74 | 2 | 9 | Cancer, Cell-To-Cell Signaling and Interaction, Cellular Function and Maintenance |
| 2 | AP3D1, ARRB1, ATP5E, ATP5I, ATP6V1D, Calmodulin, CCT6A, CD3EAP, CDC34, Ck2, DIRAS3, ENO1, F Actin, G6PD, H+-transporting two-sector ATPase, IL1A, INA, Insulin, MAP6, MRPS10, Peptidylprolyl isomerase, PPIA, PTPRZ1, Ras homolog, RHOT2, RPS2, SFRS1, SFRS11, SHROOM3, SNRP70, STK11, SUGT1, TALDO1, UBA52, WNT2 | 0 | 8 | Cancer, Cell Cycle, Carbohydrate Metabolism |
| 3 | BCL3, BCR, BRE, C5AR1, CCL8, CDH22, DIABLO, ERC1, Glutathione peroxidase, GMFB, GRB7, Ikb, IKK, IL1, IL17A, LDHA, LY96, MTPN, NFATC2, NFkB, NOL14, NUP62, PNPT1, RBCK1, RIPK3, S100P, SAP30, SLC2A6, Sod, Tnf receptor, TNFRSF14, TRAF1, TRAF2, TRIB3 | 8 | 7 | Cell Death, Gene Expression, Carbohydrate Metabolism |

Figure 6B - Table 4

Figure 6B - Table 4:
Top 20 list of gene networks from INGENUITY™ Pathway Analysis

| ID | Genes in Network | Score* | # of Genes | Top Functions |
|---|---|---|---|---|
| 4 | Actin, Adaptor protein 2, ALG5, ATP13A2, ATPase, BCAR1, BHLHB3, BRUNOL4, Caspase, CENTD2, Cyclin A, DDX11, DDX39, E2f, EID1, GARNL1, HIST1H2AG, Histone h3, HNRPK, KEAP1, KHDRBS1, MCM2, MCM5, PFDN4, PFDN5, PI3K, Rb, RUVBL1, RUVBL2, SYNCRIP, SYT3, TCF3, TGM2, THOC1, THOC2 | 6 | 6 | Gene Expression, RNA Post-Transcriptional Modification, Molecular Transport |
| 5 | Akt, ALDOA, ATXN2L, Cbp/p300, CHFR, DGKZ, EPO, Esr1-estrogen, ETV6, FAM14A, FAM89B, GC-GCR dimer, HMGB1, IL12RB2, INPP5E, JAK, MPL, N-cor, NCOR2, NOSIP, NR0B1, Nuclear factor 1, OGG1, PGR, PRMT2, PTPRF, PTPRS (includes EG:5802), STAT, STAT2, STAT5a/b, Thyroid hormone receptor, TYK2, TYRO3, UCN, WDR1 | 4 | 5 | Cellular Growth and Proliferation, Immune and Lymphatic System Development and Function, Tissue Morphology |
| 6 | ADM, Alkaline Phosphatase, Ap1, ARHGEF6, BIN1, BMP2K, CAD, CCL4, CD37, CD209, CSNK1E, Dynamin, ECE1, ELK1, ETV5, Fgf, FGF4, FGF12, JUN/JUNB/JUND, LDL, Mapk, MAX, MHC Class II, MSC, MXD3, NPC2, PLC gamma, PSMC3IP, SCARB2, SLA,SPRY1, SYK, Tgf beta, VAV, WIPF1 | 2 | 4 | Cellular Function and Maintenance,Cellular Compromise,Immune and Lymphatic System Development and Function |
| 7 | B2M, BCL7B, CD3, DUB, EEF2, GPR109B, Gsk3, Hexokinase, HK1, Ige, IGHG1, IL10, JUN, KLRC3, MAFK, Mek, MHC Class I, MYB, Nfat, NMB, Rap1, Ras, RASSF5, RELB,RIT1, SAMD4A, SCRIB, SIT1, Sos, SPI1, TCR, TYROBP, USP11, USP22, USP33 | 0 | 3 | Immune and Lymphatic System Development and Function, Tissue Morphology, Developmental Disorder |
| 8 | ADA, Adenylate Cyclase, ARF5, CACNG2, CALCB, Calpain, CaMKII, CAPN3, CAPN10, CORO1B, Creb, ERK1/2, G-protein beta, GLMN, GNAO1, GNB5, GRM3, HSF2, Integrin, ITGAM, KPNB1, MAG, MMP1, PDGF BB, Pka, Pkc(s), PLC, Pld, PP2A, PPP2R5B, RPS6KB1, SLC32A1, SNAP23, SNRPA, SYNE1 | 8 | 2 | Amino Acid Metabolism,Cell Cycle,Cell-To-Cell Signaling and Interaction |
| 9 | ADRB1, Alcohol group acceptor phosphotransferase, AMPK, Calcineurin protein(s), CUL5, DNA-directed RNA polymerase, EWSR1, FZR1, GRK4, GTF2A2, HCFC1, Hsp70, Hsp90, Jnk, LDB3, LIMK1, Mek1/2,MYOZ3, Nos, NOS1, P38 MAPK, p70 S6k, Pak, PAK2, Pdgf, POLR1D, POLR2A, POLR2E, Rac, RRM2, SETD1A, TFIIA, TK1, TOM1, Ubiquitin | 2 | 9 | Behavior,Amino Acid Metabolism, Cancer |

Figure 6B - Table 4 cont.

Figure 6B - Table 4:
Top 20 list of gene networks from INGENUITY™ Pathway Analysis

| ID | Genes in Network | Score* | # of Genes | Top Functions |
|---|---|---|---|---|
| 10 | ADCYAP1, ANKRD11, BET1L, beta-estradiol, CPLX2, CREB1, ESRRA, FAM105A, FHL5, GALNT7, GOSR1, HEXIM1, HEXIM2, NADH2 dehydrogenase (ubiquinone), NAPB, NAPG, NCOA1, NCOA2, NDUFA3, NDUFA7, NDUFA10, NDUFC1, NDUFC2, NDUFS6, NDUFV3, phosphate, PRPF31, REST, SNAP25, Snare, TRIM9, TSPAN14, UHRF1BP1, UQCR | 7 | 6 | Gene Expression, Cell Death, Connective Tissue Development and Function |
| 11 | ACPP, beta-estradiol, C11ORF10, CFD, CHST3, CHST12, CHST13, GSTM3, HES1, HS3ST2, HS3ST5, HS3ST6, HS3ST3A1, HS3ST3B1, HS3ST4, LAGE3, LHFPL2, MMD, MX2, NUDT1, PFKL, PPRC1, RBM15, SAPS2, SMP2A, sulfotransferase, SULT1A2, SULT1A4, SULT1B1, SULT1C2, SULT1C3, SULT1C4, SULT4A1, TMEM37, UST | 6 | 5 | Carbohydrate Metabolism, Small Molecule Biochemistry, Amino Acid Metabolism |
| 12 | ANAPC11, AOAH, BUB1, DNAJA2, DNAJB1, DNAJB5, ENC1, FKBP15, GBP5, GCLM, HSPA9, hydrogen peroxide, IFI6, IFNB1, LILRA2, LILRB3, LRRC47, MRPL20, NFE2L2, OSGIN1, PFDN5, PRDX6, PSMD, PSMD1, PSMD2, PSMD5, PSMD7, PSMD9, PSMD12, RAE1, RPL5, SNCA, UQCRFS1, UQCRH, XAF1 | 6 | 5 | Cancer, Cell Death, Cellular Compromise |
| 13 | ARHGEF2, C20ORF117, CDC45L, CDCA7L, CTSL2, CYFIP2, EXOSC1, EXOSC2, EXOSC3, EXOSC4, EXOSC5, EXOSC7, EXOSC8, EXOSC9, FXC1, GAS1, IFI202B, INSR, MAP4, MARK4, MNT, MXI1, MYBBP1A, MYC, NOL5A, NUDC, PLEKHF1, PRL2C2, RPL32, RPS13, RPS20, RPS15A, STRA13, SURF6, XRN1 | 4 | 4 | RNA Post-Transcriptional Modification, Cell Cycle, Connective Tissue Development and Function |
| 14 | 5-hydroxytryptamine, 5-hydroxytryptophan, APBB2, CAMK1, CIB2, DNAJC3, FKBP2, FKBP7, FKBP10, FKBP11, FKBP14, FKBP1B, GORASP2, GPNMB, HNF1A, HNMT, IL6, MIA2, PBSN, PDIA2, PIM1, PPIB, PRL, RAB27B, RAB33B, RABAC1, REG1A, RP9, SBNO2, SLC4A2, SPCS3, TMED10, TUBA1B, UNC13D, XBP1 | 4 | 4 | Molecular Transport, Small Molecule Biochemistry, Cancer |
| 15 | ACOT7, APEX1, ARL4A, ARNT2, CALB2, CCNG2, CCS, CHD2, CNDP2, FAM50A, FKBP3, G6PD2, GAK, GREM2, GSTA3, HGF, HGFAC, HIF1A, IGF2, IL13RA2, IRS2, KLK1B9, KLK1B22, KRT5, PCSK4, PNRC1, progesterone, RAB20, REG1B, RNF103, SMUG1, SPSB1, STAT3, TSSK2, ZNF592 | 4 | 4 | Cancer, Cellular Movement, Gastrointestinal Disease |

Figure 6B - Table 4 cont.

Figure 6B - Table 4:
Top 20 list of gene networks from INGENUITY™ Pathway Analysis

| ID | Genes in Network | Score* | # of Genes | Top Functions |
|---|---|---|---|---|
| 16 | ADAMTS7, ARSB, ARSC2, ARSD, ARSE, ARSF, ARSG, ARSH, ARSI, ARSJ, ARSK, Aryl Sulfatase, B4GALT3, CDKN2A, GCM1, GTSE1, HRAS, ING1, MIF, NANOG, NSUN5C, OTP, RECQL4, RPL39, S100B, SELPLG, SULF2, TIMM13, TOPORS, TP53, TPP1, TTC1, ZMAT3, Zn2+, ZNF408 | 4 | 4 | Cellular Compromise, Cancer, Tumor Morphology |
| 17 | AP2A1, ARL4C, ATP, BATF3, BCKDK, C14ORF153, C9ORF86, CASP3, CD40LG, CEBPA, CHKB, DDX21, Ethanolamine kinase, ETNK1, GRSF1, IL2, INCENP, KIF2A, KLRB1, LST1, MAGEA3, MRPS12, MT1H, MT2A, PDCD1LG2, RNASE3, SERPINB1, SPINK7, SWAP70, TBCD, TNFRSF13C, TUBA3C, TUBB2A, TUBG1 | 4 | 4 | Cancer, Infectious Disease, Cellular Growth and Proliferation |
| 18 | amino acids, APP, BTK, CDC2L2, CHAT, CLSTN1, CPM, DAPK3, DGUOK, DPYSL2, DUSP7, DYNC1I1, FANCC, FER, FPRL1, FYB, HOMER1, IBTK, ICMT, KIF5A, KIF5B, KIF5C, KLC1, KLC2, LILRA6, MAPK8IP2, MAPK8IP3, MPZL1, PHKG2, PHLDA2, PPME1, PTPN11, SPTAN1, ST8SIA1, TXK | 3 | 3 | Amino Acid Metabolism, Post-Translational Modification, Small Molecule Biochemistry |
| 19 | ARHGAP10, ARHGAP26, BCLAF1, Ck2,DEDD, DEDD2, DSG2, EGF, EIF5, EIF4A2, EIF4E, EIF4G3, GLE1, GTP, MYCBPAP, NOL3, NUP155, NUPL2, PLEKHG5, POP1, POP4, POP7, PXN, RAB11B, REPS1, RHOA, RHPN2, RND2, RPP21, RPP30, RPP38, RPP40, SAFB2, TCOF1, UBOX5 | 3 | 3 | Protein Synthesis, Cell Signaling, DNA Replication, Recombination, and Repair |
| 20 | AATF, BUB3, BUB1, C17ORF49, CDKN1A, CHMP4A, CHMP4B, CHMP4C, CPSF3, CSTF2, EAF1, ELL, ELL2, F2, HSPA9, IL32, LRSAM1, MET, MGRN1, MLL, NCBP2, NCBP1, PDCD6IP, SPSB2, SRM, STAMBP, SYMPK, TSG101, TUBG2, UBE2S, VPS24, VPS28, VPS37C, VPS4A, ZNF205 | 3 | 3 | RNA Post-Transcriptional Modification, Cellular Development, Hematological Disease |

Figure 6B - Table 4 cont.

USE OF MIR-26 FAMILY AS A PREDICTIVE MARKER FOR HEPATOCELLULAR CARCINOMA AND RESPONSIVENESS TO THERAPY

STATEMENT REGARDING FEDERALLY SPONSORED RESEARCH

This invention was made with government support under the National Cancer Institute Grant Nos. Z01 BC 010313 and Z01 BC 010876. The government has certain rights in this invention.

CROSS-REFERENCE TO RELATED APPLICATIONS

This application claims the benefit of PCT application No. PCT/US09/046999 filed Jun. 11, 2009 which claims priority to U.S. Provisional Application No. 61/131,800 filed Jun. 11, 2008, the entire disclosure of which is expressly incorporated herein by reference.

TECHNICAL FIELD AND INDUSTRIAL APPLICABILITY OF THE INVENTION

This disclosure describes the identification of miR-26 as a predictive marker for HCC patient prognosis and response to interferon (IFN)-α adjunctive therapy.

BACKGROUND

Hepatocellular carcinoma (HCC) is one of the most prevalent human malignancies worldwide, with an increasing incidence in the United States (Parkin et al., *CA Cancer J. Clin.* 55(2):74-108, 2005). HCC arises most frequently in patients with inflammatory livers resulting either from viral hepatitis caused by infection with hepatitis B virus (HBV) or hepatitis C virus (HCV), or from metabolic disorders or toxic insults. Viral hepatitis contributes to over 80% of HCC cases in the world (Thorgeirsson and Grisham, *Nat. Genet.* 31(4):339-3465, 2002; Budhu and Wang, *J. Leukoc. Biol.* 80(6):1197-1213, 2006). One of the key features of HCC is its gender disparity with a striking male dominance (i.e. 2-6 times more common in males than in females) (El Serag and Rudolph, *Gastroenterology* 132(7):2557-2576, 2007). Classical in vivo carcinogenesis experiments also reveal a higher susceptibility to HCC in male rodents (Ghebranious and Sell, *Hepatology* 27(2):383-391, 1998; Nakatani et al., *Jpn. J. Cancer Res.* 92(3):249-256, 2001; Rogers et al., *Cancer Res.* 67(24):11536-11546, 2007; Naugler et al., *Science* 317(5834):121-124, 2007). Moreover, female HCC patients tend to have a longer survival than male patients (Ng et al., *Cancer* 75(1):18-22, 1995; Dohmen et al., *J. Gastroenterol. Hepatol.* 18(3):267-272, 2003; Tangkijvanich et al., *World J. Gastroenterol.* 10(11):1547-1550, 2004.). These results indicate that tumor biology and host microenvironment may differ significantly between males and females.

A recent study suggests that the gender disparity observed in HCC may be due to an induction of Kupffer cell-produced interleukin-6 (IL-6), which can be inhibited by estrogen (Naugler et al., *Science* 317(5834):121-124, 2007). Consistent with this idea, other studies have revealed that serum IL-6 is highly elevated in several aggressive malignancies including HCC, and its expression, which can be produced by tumor cells, is associated with metastatic diseases and poor prognosis (Ashizawa et al., *Gastric Cancer* 8(2):124-131, 2005; Porta et al., *Ann. Oncol.* 19(2):353-358, 2008). These studies suggest that the procarcinogeneic activities of IL-6 may be regulated by sex hormones and tumors with activated IL-6 may be biologically distinct and more aggressive.

Surgery remains the only effective treatment modality for HCC to date with a potential to cure. However, only about 10-20% patients with HCC are currently eligible for surgical intervention. In addition, patients who receive curative resections often have a high frequency of relapse. Thus, a need remains to develop diagnostic tools that provide a sufficient resolution in assisting patient stratification for prognosis and therapy.

SUMMARY OF THE DISCLOSURE

MicroRNAs (miRs) are small, single-stranded RNA molecules that regulate gene expression. It is disclosed herein that expression of microR-26 (miR-26) is decreased in HCC tumor tissue relative to non-cancerous tissue and a low level of miR-26 is associated with a poor clinical outcome. It is also disclosed herein that a low expression level of miR-26 is correlated with a favorable response to interferon (IFN)-α therapy in HCC patients. Thus, provided herein is a method of predicting the clinical outcome of a patient diagnosed with HCC, comprising detecting the level of miR-26 expression in a HCC tumor sample obtained from the patient, wherein a decrease in the level of miR-26 expression in the tumor sample relative to a control predicts a decrease in survival, a favorable response to IFN-α therapy, or both.

Also provided is a method of selecting a patient diagnosed with HCC as a candidate for IFN-α therapy, comprising detecting the level of miR-26 expression in a HCC tumor sample obtained from the patient, wherein decrease in the level of miR-26 expression in the tumor sample relative to a control indicates the patient is a candidate for IFN-α therapy.

Further provided is a method of treating a patient diagnosed with HCC, comprising (i) detecting the level of miR-26 expression in a tumor sample obtained from the patient; (ii) comparing the level of miR-26 expression in the tumor sample to a control; and (iii) selecting a method of treatment for the patient, wherein treatment comprises IFN-α therapy only if the patient has a 1.5-fold or greater decrease in the level of miR-26 expression in the tumor sample relative to the control.

In some embodiments of the methods provided herein, the control is a non-cancerous tissue sample obtained from the patient. In other embodiments, the control is a liver sample from a healthy subject or a standard value.

Further provided is a method of identifying a therapeutic agent for the treatment of HCC, comprising screening candidate agents in vitro to select an agent that increases expression of miR-26 in HCC cells, thereby identifying an agent for the treatment of HCC. In some embodiments, screening comprises contacting the candidate agents with the HCC cells. The candidate agents can be any type of molecule, including, but not limited to cytokines or small molecules.

The foregoing and other features and advantages of the disclosure will become more apparent from the following detailed description of several embodiments which proceeds with reference to the accompanying figures.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 1A: The expression levels of miR-26a-1 in female (n=30) and male non-cancerous hepatic tissues (n=194), determined by microarray analysis. An un-paired t-test was used.

FIG. 1B: The relative expression levels of miR-26a from female cases (n=26) and age-matched male G1 and G2 cases (n=56) were determined by qRT-PCR. Un-paired t-tests were used.

FIG. 1C: Comparisons of relative levels of miR-26a-1 between 224 paired NT and T tissues when dichotomized by miR-26 status in tumors. Paired t-tests were used: p<0.001 from the low miR-26-1 group; p=0.23 from the high miR-26-1 group. The data in FIGS. 1A-1C are expressed as log 2 relative expression normalized to a disease-free normal liver pool (n=8).

FIG. 1D: miR-26a-1 expression levels in tumors, determined by microarray analysis, and survival outcomes. A log rank test was used and a median expression level was used as a cutoff. Low miR-26 expression (n=106) was classified as the lower 50th percentile (with a mean 2.69-fold reduction in T compared to NT). High miR-26 expression (n=111) was classified as the upper 50th percentile (with a mean 0.98-fold reduction in T compared to NT).

FIG. 2A: A multidimensional scaling plot of 224 HCC cases based on the expression of 11,580 genes. Samples are colored based on median dichotomization into low miR-26 expression (blue or light) or high miR-26 expression (red or dark).

FIG. 2B: A Venn diagram of mRNAs coexpressed in low miR-26 HCCs.

FIG. 2C: Gene networks of NFkB/IL-6 signaling in low miR-26 HCCs. Upregulated genes in low miR-26 HCC are highlighted in orange or light gray. Genes in gray print are not on the significant gene list but are reported to be associated with the network. Solid lines and dotted lines represent direct and indirect interactions, respectively, while arrows represent positive regulation (i.e., acts on) of gene expression. Genes connected by lines represent binding only. Detailed network relationships and network shapes are described in FIG. 15.

FIGS. 3A-3B: The association of miR-26a expression with overall survival in HCC patients from control groups (cohort 2, panel FIG. 3A; cohort 3, panel FIG. 3B). Cohort 2: high miR-26a cases, n=24; low miR-26a cases, n=35. Cohort 3: high miR-26a cases, n=21; low miR-26a cases, n=19.

FIGS. 3C-3D: The association of IFN adjuvant therapy with overall survival in HCC patients with low miR-26a expression. Cohort 2: IFN cases, n=24; control cases, n=35. Cohort 3: IFN cases, n=20; control cases, n=19.

FIGS. 3E-3F: The association of IFN adjuvant therapy with overall survival in HCC patients with high miR-26a expression. Cohort 2: IFN cases, n=35; control cases, n=24. Cohort 3: IFN cases, n=19; control cases, n=21.

FIG. 4A: Table 1—Clinical characteristics of the subjects for Cohort 1 and Cohort 2.

FIG. 4B: Supplemental Table 1—Clinical characteristics of the subjects for INF tests—Cohort 2 and Cohort 3.

FIG. 4C: Supplemental Table 2—Clinical characteristics of cases used to search for gender-related microRNAs.

FIG. 5A: Table 2—Univariate and Multivariate Cox Regression Analysis of miR-26 Expression Levels and Overall Survival in Subjects with HCC.

FIG. 5B: Table 3—Univariate and Multivariate Cox Regression Analysis of Interferon Therapy and Overall Cancer Survival in Subjects with Low miR-26 Expression.

FIG. 6A: Supplemental Table 3—Eight Gender-Related microRNAs.

FIG. 6B: Table 4—Top 20 list of gene networks from INGENUITY™ Pathway Analysis.

FIG. 7A: The expression levels of miR-26a-2 in female (n=30) and male non-tumor hepatic tissues (n=194).

FIG. 7B: Comparisons of relative levels of miR-26a-2 between paired T and NT when dichotomized by miR-26 status. A median expression level was used as a cutoff. Low miR-26 expression was classified as the lower 50th percentile (with a mean 2.69-fold reduction in T compared to NT). High miR-26 expression was classified as the upper 50th percentile (with a mean 0.98-fold reduction in T compared to NT). The data in FIG. 7A and FIG. 7B were determined by microarray analysis and expressed as log 2 relative expression normalized to a disease-free normal liver pool (n=8).

FIG. 7C: miR-26a-2 expression levels in tumors and survival outcomes.

FIGS. 7D-7F: Similar results as in FIG. 7A-7C with miR-26b expression status.

FIG. 10A: Expression levels of IL-6 in 82 paired tumors (T) and non-tumor tissues (NT) determined by qRT-PCR. Student's t-test was performed to examine the IL-6 differential expression between T and NT.

FIGS. 10B-10C: Correlation of expression levels between IL-6 and miR-26a (B FIG. 10B) or miR-26b (FIG. 10C) in 82 paired tumors and non-tumor tissues determined by qRT-PCR. The data are shown as the T/NT ratio on a log 2 scale.

FIGS. 12A-12B: The association of miR-26b expression with overall survival in control cases from cohort 2 (FIG. 6A) or cohort 3 (FIG. 12B). Cohort 2: high miR-26b cases, n=23; low miR-26b cases, n=36. Cohort 3: high miR-26b cases, n=21; low miR-26b cases, n=19.

FIGS. 12C-12D: The association of IFN adjuvant therapy with overall survival in HCC patients with low miR-26b expression. Cohort 2: IFN cases, n=22; control cases, n=36. Cohort 3: IFN cases, n=20; control cases, n=19.

FIGS. 12E-12F: The association of IFN adjuvant therapy with overall survival in HCC patients with high miR-26a expression. Cohort 2: IFN cases, n=37; control cases, n=23. Cohort 3: IFN cases, n=19; control cases, n=21.

SEQUENCE LISTING

Figures 1A, 1B, 1C, 1D:
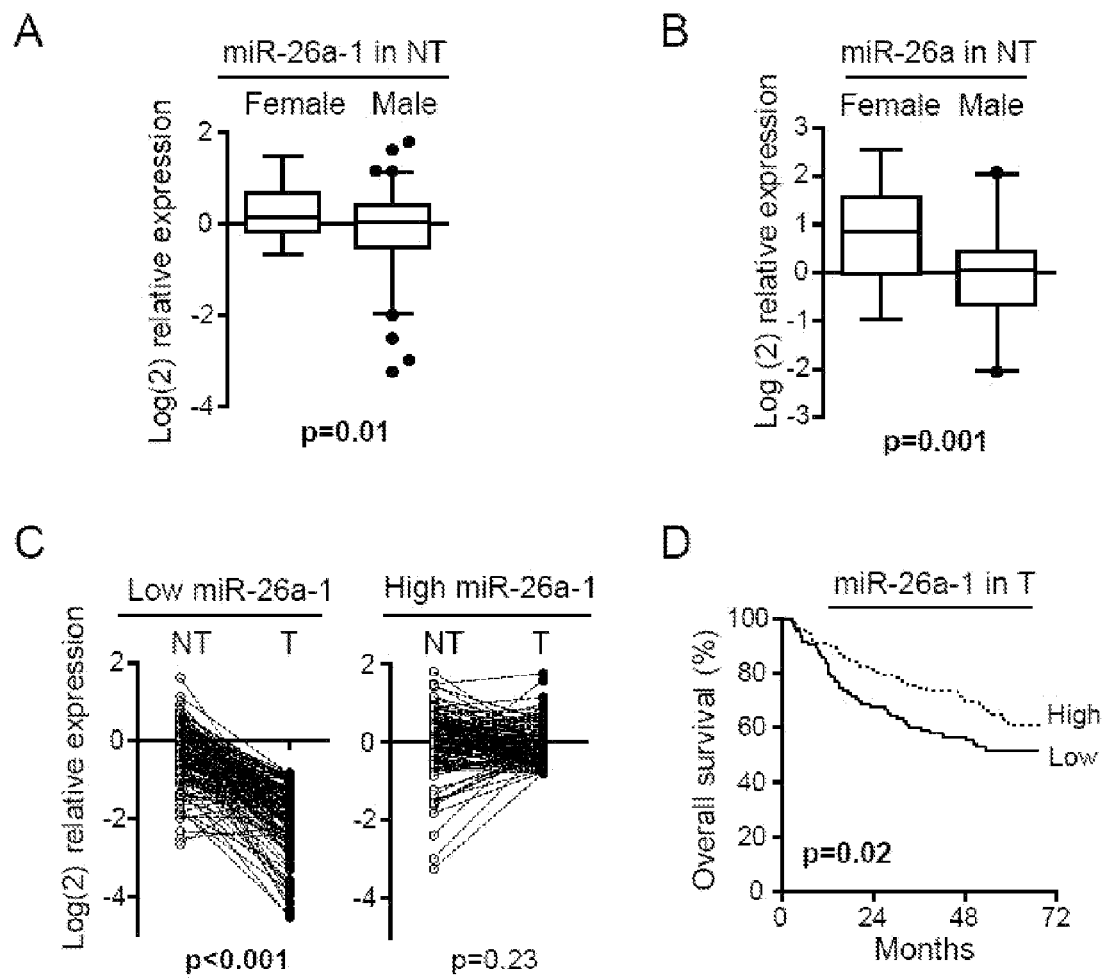
FIGS. 1A-1D: miR-26 expression in male and female hepatic tissues and tumors.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

[SEQ ID NO: 1] is the nucleotide sequence of the precursor form of human miR-26a-1=guggccucgu ucaaguaauc caggauaggc ugugcagguc ccaaugggcc uauucuuggu

[SEQ ID NO: 2] is the nucleotide sequence of the precursor form of human miR-26a-2=ggcuguggcu ggauucaagu aauccaggau aggcuguuuc caucugugag gccuauucuu gauuacuugu uucuggaggc agcu

[SEQ ID NO: 3] is the nucleotide sequence of the precursor form of human miR-26b=ccgggaccca guucaaguaa uucaggauag guugugugcu guccagccug uucuccauua cuuggcucgg ggaccgg

[SEQ ID NO: 4] is the nucleotide sequence of the mature form of human miR-26a-1 and miR-26a-2=uucaaguaau ccaggauagg cu.

[SEQ ID NO: 5] is the nucleotide sequence of the mature form of human miR-26b=uucaaguaau ucaggauagg u.

DETAILED DESCRIPTION

Abbreviations

1NN 1-Nearest neighbor
3NN 3-Nearest neighbor
AFP Alpha-fetoprotein
ALT Alanine aminotransferase
CCP Compound covariate predictor
DLD Diagonal linear discriminant
DNA Deoxyribonucleic acid
HBV Hepatitis B virus
HCC Hepatocellular carcinoma
HCV Hepatitis C virus
IFN Interferon
IL Interleukin
ISH In situ hybridization
miR MicroRNA
miRNA MicroRNA
mRNA Messenger RNA
NC Nearest centroid
PCR Polymerase chain reaction
pre-miRNA Precursor microRNA
qRT-PCR Quantitative reverse transcriptase polymerase chain reaction
RNA Ribonucleic acid
siRNA Small interfering RNA
snRNA Small nuclear RNA
SVM Support vector machines
TACE Transcatheter arterial chemoembolization
TNM Tumor-node-metastasis

TERMS

It is to be understood that both the foregoing general description and the following detailed description are exemplary and explanatory only and are not intended to limit the scope of the current teachings. In this application, the use of the singular includes the plural unless specifically stated otherwise.

The use of the word "a" or "an" when used in conjunction with the term "comprising" in the claims and/or the specification may mean "one," but it is also consistent with the meaning of "one or more," "at least one," and "one or more than one."

Also, the use of "comprise", "contain", and "include", or modifications of those root words, for example but not limited to, "comprises", "contained", and "including", are not intended to be limiting. The term "and/or" means that the terms before and after can be taken together or separately. For illustration purposes, but not as a limitation, "X and/or Y" can mean "X" or "Y" or "X and Y".

It is understood that an miRNA is derived from genomic sequences or a gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary miRNA probes of the invention can be or be at least 60, 65, 70, 75, 80, 85, 90, 95, or 100% complementary to their target.

The term "combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB.

The section headings used herein are for organizational purposes only and are not to be construed as limiting the described subject matter in any way. All literature and similar materials cited in this application, including patents, patent applications, articles, books, treatises, and internet web pages are expressly incorporated by reference in their entirety for any purpose. In the event that one or more of the incorporated literature and similar materials defines or uses a term in such a way that it contradicts that term's definition in this application, this application controls.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjunctive therapy: A treatment used in combination with a primary treatment to improve the effects of the primary treatment. For example, a patient diagnosed with HCC may undergo liver resection as a primary treatment and interferon (IFN)-α therapy as an adjunctive therapy.

Candidate: As used herein, a "candidate" for IFN-α therapy is a patient that is predicted to respond favorably to IFN-α therapy for the treatment of HCC.

Clinical outcome: Refers to the health status of a patient following treatment for a disease or disorder, such as HCC, or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

Control: A "control" refers to a sample or standard used for comparison with an experimental sample, such as a tumor sample obtained from a HCC patient. In some embodiments, the control is a liver sample obtained from a healthy patient or a non-cancerous tissue sample obtained from a patient diagnosed with HCC. In some embodiments, the control is a historical control or standard value (i.e. a previously tested control sample or group of samples that represent baseline or normal values, such as the level of miR-26 expression in non-cancerous tissue).

Cytokines: Proteins produced by a wide variety of hematopoietic and non-hematopoietic cells that affect the behavior of other cells. Cytokines are important for both the innate and adaptive immune responses.

Decrease in survival: As used herein, "decrease in survival" refers to a decrease in the length of time before death of a patient, or an increase in the risk of death for the patient.

Detecting level of expression: As used herein, "detecting the level of miR-26 expression" refers to quantifying the amount of miR-26 present in a sample. Detecting expression of miR-26, or any microRNA, can be achieved using any method known in the art or described herein, such as by qRT-PCR. Detecting expression of miR-26 includes detecting expression of either a mature form of miR-26 or a precursor form that is correlated with miR-26 expression. Typically, miRNA detection methods involve sequence specific detection, such as by RT-PCR miR-26-specific primers and probes can be designed using the precursor and mature miR-26 nucleic acid sequences, which are known in the art and provided herein as SEQ ID NOs: 1-5.

Hepatocellular carcinoma (HCC): HCC is a primary malignancy of the liver typically occurring in patients with inflammatory livers resulting from viral hepatitis, liver toxins or hepatic cirrhosis (often caused by alcoholism).

Interferon (IFN)-α: Interferons are a type of cytokine produced by a variety of different cell types, including leukocytes (such as T cells, B cells and natural killer cells) and fibroblasts. Interferon is induced in response to exposure to foreign agents such as viruses, parasites and tumors. Double-stranded RNA, often indicative of a viral infection, is a common inducer of interferon. Interferons are important for inhibiting viral replication, activating natural killer cells and macrophages, and increasing antigen presentation to lymphocytes. Interferons include IFN-α, IFN-β and IFN-γ. As used herein, "IFN therapy" or "IFN-α therapy" for HCC refers to treatment with IFN-α. As used herein, "a favorable response to IFN therapy" or "a favorable response to IFN-α therapy" means a patient treated with IFN-α has an increase in survival (an increase in the length of time until death, or an increased chance of survival), an improvement in the symptoms of HCC, a decrease in spread or metastasis of HCC, a decrease in severity or aggressiveness of disease, or any other appropriate clinical parameter for measuring a positive response to therapy.

MicroRNA (miRNA, miR): Single-stranded RNA molecules that regulate gene expression. MicroRNAs are generally 21-23 nucleotides in length. MicroRNAs are processed from primary transcripts known as pri-miRNA to short stem-loop structures called precursor (pre)-miRNA and finally to functional, mature microRNA. Mature microRNA molecules are partially complementary to one or more messenger RNA molecules, and their primary function is to down-regulate gene expression. MicroRNAs regulate gene expression through the RNAi pathway.

MicroRNA-26: Refers to a family of microRNAs (also referred to as miRs) that currently includes miR-26a-1, miR-26a-2 and miR-26b. The term "microRNA-26" also includes any as yet unidentified members of the microRNA-26 family that are differentially expressed in HCC tumors relative to healthy tissues.

miR-26 expression: As used herein, "low miR-26 expression" and "high miR-26 expression" are relative terms that refer to the level of miR-26 found in a sample, such as a healthy or HCC liver sample. In some embodiments, low and high miR-26 expression are determined by comparison of miR-26 levels in a group of non-cancerous and HCC liver samples. Low and high expression can then be assigned to each sample based on whether the expression of miR-26 in a sample is above (high) or below (low) the average or median miR-26 expression level. For individual samples, high or low miR-26 expression can be determined by comparison of the sample to a control or reference sample known to have high or low expression, or by comparison to a standard value. Low and high miR-26 expression can include expression of either the precursor or mature forms or miR-26, or both.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as HCC) refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Screening: As used herein, "screening" refers to the process used to evaluate and identify candidate agents that increase expression of miR-26. In some cases, screening involves contacting a candidate agent (such as an antibody, small molecule or cytokine) with HCC cells and testing the effect of the agent on expression of miR-26. Expression of a microRNA can be quantified using any one of a number of techniques known in the art and described herein, such as by microarray analysis or by qRT-PCR.

Small molecule: A molecule, typically with a molecular weight less than about 1000 Daltons, or in some embodiments, less than about 500 Daltons, wherein the molecule is capable of modulating, to some measurable extent, an activity of a target molecule.

Therapeutic: A generic term that includes both diagnosis and treatment.

Therapeutic agent: A chemical compound, small molecule, or other composition, such as an antisense compound, antibody, protease inhibitor, hormone, chemokine or cytokine, capable of inducing a desired therapeutic or prophylactic effect when properly administered to a subject. For example, therapeutic agents for HCC include agents that prevent or inhibit development or metastasis of HCC. As used herein, a "candidate agent" is a compound selected for screening to determine if it can function as a therapeutic agent for HCC. In some embodiments, the candidate agent is identified as a therapeutic agent if the agent increases expression of miR-26 in HCC cells. "Incubating" includes a sufficient amount of time for an agent to interact with a cell or tissue. "Contacting" includes incubating an agent in solid or in liquid form with a cell or tissue. "Treating" a cell or tissue with an agent includes contacting or incubating the agent with the cell or tissue.

Therapeutically effective amount: A quantity of a specified pharmaceutical or therapeutic agent sufficient to achieve a desired effect in a subject, or in a cell, being treated with the agent. For example, this can be the amount of a therapeutic agent that increases expression of miR-26 and/or the amount of a therapeutic agent that prevents, treats or ameliorates HCC in a patient. The effective amount of the agent will be dependent on several factors, including, but not limited to the subject or cells being treated, and the manner of administration of the therapeutic composition.

Tumor, neoplasia, malignancy or cancer: The result of abnormal and uncontrolled growth of cells. Neoplasia, malignancy, cancer and tumor are often used interchangeably and refer to abnormal growth of a tissue or cells that results from excessive cell division. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Tumor-Node-Metastasis (TNM): The TNM classification of malignant tumors is a cancer staging system for describing the extent of cancer in a patient's body. T describes the size of the primary tumor and whether it has invaded nearby tissue; N describes any lymph nodes that are involved; and M describes metastasis. TNM is developed and maintained by the International Union Against Cancer to achieve consensus on one globally recognized standard for classifying the extent of spread of cancer. The TNM classification is also used by the American Joint Committee on Cancer and the International Federation of Gynecology and Obstetrics.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Overview of Several Embodiments

It is disclosed herein that expression of miR-26 is decreased in HCC tumor tissue relative to non-cancerous tissue, and a low level of miR-26 is associated with a poor clinical outcome. It is also disclosed herein that a low expression level of miR-26 is correlated with a favorable response to IFN-α therapy in HCC patients.

Thus, provided herein is a method of predicting the clinical outcome of a patient diagnosed with HCC, comprising detecting the level of miR-26 expression in a HCC tumor sample obtained from the patient, wherein a decrease in the level of miR-26 expression in the tumor sample relative to a control predicts a decrease in survival, a favorable response to IFN-α therapy, or both. Also provided is a method of selecting a patient diagnosed with HCC as a candidate for IFN-α therapy, comprising detecting the level of miR-26 expression in a HCC tumor sample obtained from the patient, wherein a decrease in the level of miR-26 expression in the tumor sample relative to a control indicates the patient is a candidate for IFN-α therapy.

In one embodiment of the methods, the miR-26 is miR-26a-1. In another embodiment, the miR-26 is miR-26a-2. In another embodiment, the miR-26 is miR-26b. In other embodiments, miR-26 is a combination of two or more of miR-26a-1, miR-26a-2 and miR-26b.

In some embodiments, the control is non-cancerous tissue sample obtained from the same patient. In other embodiments, the control is a liver sample obtained from a healthy subject, such as a healthy liver donor. In another example, the control is a standard calculated from historical values. Tumor samples and non-cancerous tissue samples can be obtained according to any method known in the art. For example, tumor and non-cancerous samples can be obtained from HCC patients that have undergone liver resection, or they can be obtained by extraction using a hypodermic needle, by microdissection, or by laser capture. Control (non-cancerous) samples can be obtained, for example, from a cadaveric donor or from a healthy liver donor.

Expression of miR-26 in the tumor sample is decreased (relative to a control) by an amount sufficient to impart a phenotypic effect, such as rendering the tumor more susceptible to treatment by IFN-α, altering the rate of growth of the tumor, rendering the tumor capable of metastasis. While not wishing to be bound by theory, the phenotypic effect is thought to be mediated by differential gene expression regulated by miR-26. The phenotypic effect can also be an increase or decrease in expression of one or more miR-26 regulated genes. In some embodiments, expression of miR-26 in the tumor sample is decreased at least 1.1-fold, at least 1.2-fold, at least 1.3-fold or at least 1.4-fold. In one embodiment, expression of miR-26 in the tumor sample is decreased at least 1.5-fold relative to the control. In another embodiment, expression of miR-26 in the tumor sample is decreased at least 2-fold relative to the control. In another embodiment, expression of miR-26 in the tumor sample is decreased at least 2.5-fold relative to the control. In another embodiment, expression of miR-26 in the tumor sample is decreased at least 3-fold relative to the control. In another embodiment, expression of miR-26 in the tumor sample is decreased at least 3.5-fold relative to the control. In another embodiment, expression of miR-26 in the tumor sample is decreased at least 4-fold relative to the control. In other embodiments, expression of miR-26 in the tumor sample is decreased at least 5-fold, at least 6-fold, at least 7-fold, at least 8-fold, at least 9-fold, or at least 10-fold. Expression of miR-26 can be detected and quantified using any method known in the art, such as, but not limited to microarray and qRT-PCR.

Further provided is a method of identifying a therapeutic agent for the treatment of HCC, comprising screening candidate agents in vitro to select an agent that increases expression of miR-26 in HCC cells, thereby identifying an agent for the treatment of HCC.

In some embodiments, screening comprises contacting the candidate agents with the HCC cells. The HCC cells can be primary cells obtained from a HCC patient, or the HCC cells can be immortalized or transformed cells. In one embodiment, expression of miR-26 in the HCC cells is increased at least 2-fold relative to untreated cells. In another embodiment, expression of miR-26 in the HCC cells is increased at least 3-fold relative to untreated cells. In another embodiment, expression of miR-26 in the HCC cells is increased at least 4-fold relative to untreated cells.

The candidate agents can be any type of agent, such as a protein, peptide, small molecule, antibody or nucleic acid. In some embodiments, the candidate agent is a cytokine. In some embodiments, the candidate agent is a small molecule. Screening includes both high-throughout screening and screening individual or small groups of candidate agents.

Further provided is a method of treating a patient diagnosed with HCC, comprising (i) detecting the level of miR-26 expression in a tumor sample obtained from the patient; (ii) comparing the level of miR-26 expression in the tumor sample to a control; and (iii) selecting a method of treatment for the patient, wherein treatment comprises IFN-α therapy only if the patient has a 1.5-fold or greater decrease in the level of miR-26 expression in the tumor sample relative to the control. In some embodiments, the miR-26 is miR-26a-1, miR-26a-2, miR-26b, or a combination thereof.

In some embodiments, the method of treatment further comprises liver resection. In some embodiments, IFN-α therapy comprises administration of IFN-α.

In one embodiment, the control is a non-cancerous tissue sample obtained from the patient. In another embodiment, the control is a liver sample from a healthy subject. In another embodiment, the control is a standard value.

In some embodiments of the method, expression of miR-26 in the tumor sample is decreased at least 2-fold, at least 2.5-fold, at least 3-fold or at least 4-fold.

Tumor Tissue Samples

The methods provided herein include detecting the level of miR-26 expression in tumor and non-tumor tissue samples. In some embodiments, the tissue samples are obtained from subjects diagnosed with HCC and, in some cases, from healthy subjects or cadaveric donors. A "sample" refers to part of a tissue that is either the entire tissue, or a diseased or healthy portion of the tissue. As described herein, tumor tissue samples are compared to a control. In some embodiments, the control is non-cancerous tissue sample obtained from the same subject, such as non-cancerous hepatic tissue surrounding the HCC tumor. In other embodiments, the control is a liver sample obtained from a healthy patient or a non-cancerous tissue sample from a cadaver. In other embodiments, the reference sample is a standard based on historical values.

Tissue samples can be obtained from a subject using any method known in the art. For example, tissue samples can be obtained from HCC patients who have undergone liver resection as a treatment for HCC. From these patients, both tumor tissue and surrounding non-cancerous hepatic tissue can be obtained. In some embodiments, the non-cancerous tissue sample used as a control is obtained from a cadaver. In other embodiments, the non-cancerous tissue sample is obtained from a healthy liver donor (see Kim et al., *Hepatology* 39(2): 518-527, 2004).

In some embodiments, tissue samples are obtained by biopsy. Biopsy samples can be fresh, frozen or fixed, such as formalin-fixed and paraffin embedded. Samples can be removed from a patient surgically, by extraction (for example by hypodermic or other types of needles), by microdissection, by laser capture, or by any other means known in the art.

Methods of Detecting miR-26 Expression

The sequences of precursor microRNAs (pre-miRNAs) and mature miRNAs are publicly available, such as through the miRBase database, available online by the Sanger Institute (see Griffiths-Jones et al., *Nucleic Acids Res.* 36:D154-D158, 2008; Griffiths-Jones et al., *Nucleic Acids Res.* 34:D140-D144, 2006; and Griffiths-Jones, *Nucleic Acids Res.* 32:D109-D111, 2004). The sequences of the precursor and mature forms of miR-26 family members are provided herein as SEQ ID NOs: 1-5. Although the precursor forms of miR-26a-1 and miR-16a-2 are different, the sequences of the mature forms of these miRs are identical (SEQ ID NO: 4).

Detection and quantification of microRNA expression can be achieved by any one of a number of methods well known in the art (see, for example, U.S. Patent Application Publication Nos. 2006/0211000 and 2007/0299030, herein incorporated by reference) and described below. Using the known sequences for miR-26 family members, specific probes and primers can be designed for use in the detection methods described below as appropriate.

In some cases, the miRNA detection method requires isolation of nucleic acid from a sample, such as a cell or tissue sample. Nucleic acids, including RNA and specifically miRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain miRNAs and small interfering RNAs (siRNAs).

Microarray

A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used, for example, to measure the expression levels of large numbers of messenger RNAs (mRNAs) and/or miRNAs simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

Microarray analysis of miRNAs can be accomplished according to any method known in the art (see, for example, PCT Publication No. WO 2008/054828; Ye et al., Nat. Med. 9(4):416-423, 2003; Calin et al., N. Engl. J. Med. 353(17): 1793-1801, 2005, each of which is herein incorporated by reference). In one example, RNA is extracted from a cell or tissue sample, the small RNAs (18-26-nucleotide RNAs) are size-selected from total RNA using denaturing polyacrylamide gel electrophoresis. Oligonucleotide linkers are attached to the 5' and 3' ends of the small RNAs and the resulting ligation products are used as templates for an RT-PCR reaction with 10 cycles of amplification. The sense strand PCR primer has a fluorophore attached to its 5' end, thereby fluorescently labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

In an alternative method, total RNA containing the small RNA fraction (including the miRNA) extracted from a cell or tissue sample is used directly without size-selection of small RNAs, and 3' end labeled using T4 RNA ligase and either a fluorescently-labeled short RNA linker. The RNA samples are labeled by incubation at 30° C. for 2 hours followed by heat inactivation of the T4 RNA ligase at 80° C. for 5 minutes. The fluorophore-labeled miRNAs complementary to the corresponding miRNA capture probe sequences on the array will hybridize, via base pairing, to the spot at which the capture probes are affixed. The microarray scanning and data processing is carried out as described above.

There are several types of microarrays than be employed, including spotted oligonucleotide microarrays, pre-fabricated oligonucleotide microarrays and spotted long oligonucleotide arrays. In spotted oligonucleotide microarrays, the capture probes are oligonucleotides complementary to miRNA sequences. This type of array is typically hybridized with amplified PCR products of size-selected small RNAs from two samples to be compared (such as non-cancerous tissue and HCC liver tissue) that are labeled with two different fluorophores. Alternatively, total RNA containing the small RNA fraction (including the miRNAs) is extracted from the two samples and used directly without size-selection of small RNAs, and 3' end labeled using T4 RNA ligase and short RNA linkers labeled with two different fluorophores. The samples can be mixed and hybridized to one single microarray that is then scanned, allowing the visualization of up-regulated and down-regulated miRNA genes in one assay.

In pre-fabricated oligonucleotide microarrays or single-channel microarrays, the probes are designed to match the sequences of known or predicted miRNAs. There are commercially available designs that cover complete genomes (for example, from Affymetrix or Agilent). These microarrays give estimations of the absolute value of gene expression and therefore the comparison of two conditions requires the use of two separate microarrays.

Spotted long Oligonucleotide Arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing.

Quantitative RT-PCR

Quantitative RT-PCR (qRT-PCR) is a modification of polymerase chain reaction used to rapidly measure the quantity of a product of polymerase chain reaction. qRT-PCR is commonly used for the purpose of determining whether a genetic sequence, such as a miR, is present in a sample, and if it is present, the number of copies in the sample. Any method of PCR that can determine the expression of a nucleic acid molecule, including a miRNA, falls within the scope of the present disclosure. There are several variations of the qRT-PCR method known in the art, three of which are described below.

Methods for quantitative polymerase chain reaction include, but are not limited to, via agarose gel electrophoresis, the use of SYBR Green (a double stranded DNA dye), and the use of a fluorescent reporter probe. The latter two can be analyzed in real-time.

With agarose gel electrophoresis, the unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown.

The use of SYBR Green dye is more accurate than the agarose gel method, and can give results in real time. A DNA binding dye binds all newly synthesized double stranded DNA and an increase in fluorescence intensity is measured, thus allowing initial concentrations to be determined. However, SYBR Green will label all double-stranded DNA, including any unexpected PCR products as well as primer dimers, leading to potential complications and artifacts. The reaction is prepared as usual, with the addition of fluorescent double-stranded DNA dye. The reaction is run, and the levels of fluorescence are monitored (the dye only fluoresces when bound to the double-stranded DNA). With reference to a standard sample or a standard curve, the double-stranded DNA concentration in the PCR can be determined.

The fluorescent reporter probe method uses a sequence-specific nucleic acid based probe so as to only quantify the probe sequence and not all double stranded DNA. It is commonly carried out with DNA based probes with a fluorescent reporter and a quencher held in adjacent positions (so-called dual-labeled probes). The close proximity of the reporter to the quencher prevents its fluorescence; it is only on the breakdown of the probe that the fluorescence is detected. This process depends on the 5' to 3' exonuclease activity of the polymerase involved.

The real-time quantitative PCR reaction is prepared with the addition of the dual-labeled probe. On denaturation of the double-stranded DNA template, the probe is able to bind to its complementary sequence in the region of interest of the template DNA. When the PCR reaction mixture is heated to activate the polymerase, the polymerase starts synthesizing the complementary strand to the primed single stranded template DNA. As the polymerization continues, it reaches the probe bound to its complementary sequence, which is then hydrolyzed due to the 5'-3' exonuclease activity of the polymerase, thereby separating the fluorescent reporter and the quencher molecules. This results in an increase in fluorescence, which is detected. During thermal cycling of the real-time PCR reaction, the increase in fluorescence, as released from the hydrolyzed dual-labeled probe in each PCR cycle is monitored, which allows accurate determination of the final, and so initial, quantities of DNA.

In Situ Hybridization

In situ hybridization (ISH) applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of miRNAs.

Sample cells or tissues are treated to increase their permeability to allow a probe, such as a miRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a non-cancerous or HCC liver sample. Since the sequences of miR-26 family members are known, miR-26 probes can be designed accordingly such that the probes specifically bind miR-26.

In Situ PCR

In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

Use of miR-26 as a Predictive Marker of HCC Prognosis and for Identification of Therapeutic Agents for Treatment of HCC It is disclosed herein that miR-26 is an independent predictor of survival prognosis in HCC patients. HCC tumor samples with low miR-26 expression compared to non-cancerous tissue from the same subject or from a healthy subject, predicts a decrease in survival. In addition, when therapy outcomes from IFN-α treatment of HCC patients were stratified, only patients with low miR-26 expression in tumors responded to IFN-α therapy favorably. Thus, miR-26 status in tumors can be used as a clinical tool in HCC patients' prognosis and for selecting appropriate HCC patients who can benefit from IFN-α adjuvant therapy to prevent relapse. In some cases, IFN-α therapy is used after radical liver resection.

In some embodiments, the expression level of miR-26 in a HCC tumor sample is directly compared with the expression level of miR-26 in surrounding non-cancerous tissue from the same patient. In other embodiments, miR-26 expression in the tumor sample is compared to the expression level of miR-26 in a liver sample obtained from a healthy subject, such as a liver donor. In some cases, the non-cancerous tissue used as a control sample is obtained from a cadaver. In other embodiments, expression of miR-26 in the tumor sample is compared with a standard level based on historical values. For example, the standard can be set based on average expression levels of miR-26 in non-cancerous liver tissue samples obtained from a cohort of subjects. For instance, the cohort of subjects can be a group of HCC patients enrolled in a clinical trial. The cohort of subject can also be a group of cadaveric donors.

Low expression of one or more miR-26 family members in a HCC tumor sample relative to a control indicates a poor prognosis for the patient and identifies the patient as a good candidate for IFN-α adjunctive therapy. As used herein, "poor prognosis" generally refers to a decrease in survival, or in other words, an increase in risk of death or a decrease in the time until death. Poor prognosis can also refer to an increase in severity of the disease, such as an increase in spread (metastasis) of the cancer to other organs. In one embodiment, low expression of miR-26 is indicated by at least a 1.5-fold decrease in expression relative to the control. In other embodiments, low expression of miR-26 is indicated by at least a 2-fold, at least a 2.5-fold, at least a 3-fold, at least a 3.5-fold, or at least a 4-fold decrease in miR-26 expression relative to the control.

The finding that patients with HCC tumors having higher levels of miR-26 expression have a better chance of survival indicates that compounds that increase expression of miR-26 will be useful as therapeutic agents for the treatment of HCC. Thus, provided herein is a method of identifying therapeutic agents for the treatment of HCC, comprising screening candidate agents in vitro to select an agent that increases expression of miR-26 in HCC cells. In some embodiments, screening comprises contacting the candidate agents with HCC cells and detecting any change in the expression level of miR-26 in the cells. The HCC cells can be primary cells obtained from a HCC patient, immortalized or transformed cells obtained from a patient, or the cells can be commercially available immortalized cell lines, such as, but not limited to MHCC97, HepG2, Hep3B or SNU-423 cells.

An increase in expression of miR-26 following treatment with the candidate agent identifies the agent as a therapeutic agent for the treatment of HCC. Methods of screening candidate agents to identify therapeutic agents for the treatment of disease are well known in the art. Methods of detecting expression levels of miR-26 are known in the art and are described herein, such as, but not limited to, microarray analysis, RT-PCR (including qRT-PCR), in situ hybridization, in situ PCR, and Northern blot analysis. In one embodiment, screening comprises a high-throughput screen. In another embodiment, candidate agents are screened individually.

The candidate agents can be any type of molecule, such as, but not limited to nucleic acid molecules, proteins, peptides, antibodies, lipids, small molecules, chemicals, cytokines, chemokines, hormones, or any other type of molecule that may alter miR-26 expression either directly or indirectly. In some embodiments, the candidate agents are molecules that play a role in the NFκB/IL-6 signaling pathway. In other embodiments, the candidate agents are molecules that play a role in the IL-10, STAT3 or interferon-inducible factor signaling networks. In one embodiment, the candidate agents are cytokines. In another embodiment, the candidate agents are small molecules.

Also described herein is a method for the characterization of hepatocellular carcinoma (HCC), wherein at least one feature of HCC is selected from one or more of the group consisting of: presence or absence of HCC; diagnosis of HCC; prognosis of HCC; therapy outcome prediction; therapy outcome monitoring; suitability of HCC to treatment, such as suitability of HCC to chemotherapy treatment and/or radiotherapy treatment; suitability of HCC to hormone treatment; suitability of HCC for removal by invasive surgery; suitability of HCC to combined adjuvant therapy.

Also described herein is a kit for the detection of HCC, the kit comprising at least one detection probe comprising one or more members of the miR-26 family. The kit can be in the form or comprises an oligonucleotide array.

Also described herein is a method for the determination of suitability of a HCC patient for treatment comprising: i) isolating at least one tissue sample from a patient suffering from HCC; ii) performing the characterization of at least one tissue sample and/or utilizing a detection probe, to identify at least one feature of the HCC; iii) based on the at least one feature identified in step ii), diagnosing the physiological status of the patient; iv) based on the diagnosis obtained in step iii), determining whether the patient would benefit from treatment of the HCC.

In certain embodiments, the at least one feature of the cancer is selected from one or more of the group consisting of: presence or absence of the cancer; type of the cancer; origin of the cancer; diagnosis of cancer; prognosis of the cancer; therapy outcome prediction; therapy outcome monitoring; suitability of the cancer to treatment, such as suitability of the cancer to chemotherapy treatment and/or radiotherapy treatment; suitability of the cancer to hormone treatment; suitability of the cancer for removal by invasive surgery; suitability of the cancer to combined adjuvant therapy.

Also described herein is a method of for the determination of suitability of a cancer for treatment, wherein the at least one feature of the cancer is suitability of the cancer to treatment, such as suitability of the cancer to chemotherapy treatment and/or radiotherapy treatment; suitability of the cancer to hormone treatment; suitability of the cancer for removal by invasive surgery; suitability of the cancer to combined adjuvant therapy.

Also described herein is a method for the determination of the likely prognosis of a HCC patient comprising: i) isolating at least one tissue sample from a patient suffering from HCC; and, ii) characterizing at least one tissue sample to identify at least one feature of the HCC; wherein the feature allows for the determination of the likely prognosis of the HCC patient.

The following examples are provided to illustrate certain particular features and/or embodiments. These examples should not be construed to limit the disclosure to the particular features or embodiments described.

EXAMPLES

The Examples below describe the analysis of gender-dependent microRNA profiles in HCC and their predictive values in survival prognosis and therapeutic outcomes. For these studies, two independent cohorts of 379 total HCC patients were analyzed. The first cohort was a test cohort to identify potential microRNAs associated with HCC. The second cohort (the validation cohort) was used to confirm the results obtained from the test cohort. Using this strategy, members of miR-26 were identified as gender-related microRNAs as they were more abundantly expressed in female hepatic tissues. In addition, the expression levels of miR-26 family members were significantly downregulated in a subset of HCC tumor samples as compared to their paired non-cancerous tissues regardless of gender. Tumors with reduced miR-26 expression had a distinct gene expression profile, and cases with low miR-26 expression were associated with poor survival prognosis. The data described below suggests that miR-26 functions as a tumor suppressor and tumors with miR-26 silencing may be biologically unique.

Example I

Materials, Methods and Patient Characteristics

Clinical Specimens

Snap frozen or paraffin-embedded specimens of both tumors (T) and surrounding non-tumor hepatic tissues (NT) were obtained with informed consent from 455 HCC patients who underwent radical resection at the Liver Cancer Institute of Fudan University, Shanghai (376 cases) and at the University of Hong Kong Medical Centre, Hong Kong (79 cases), China (4). The study was approved by the Institutional Review Board of the corresponding institutes. A normal liver tissue sample pool was obtained from 8 disease-free liver donors (24). A previously described cohort of 241 HCC cases (cohort 1: test cohort), with available microRNA microarray data (22), was used to search for microRNAs associated with gender and survival. Among them, 17 had missing miR-26 expression data and 9 had missing survival data, leaving 224 cases for miR-26 expression analysis and 217 cases for survival analyses. HCC cases (n=135) from prospective randomized control trials (RCT) (cohort 2: validation cohort and IFN test cohort) (3) to evaluate adjuvant IFN therapy were used as an independent validation cohort by quantitative reverse transcription polymerase chain reaction (qRT-PCR). Among cohort 2, 6 had missing miR-26 expression data and 12 had missing survival data, leaving 129 cases (60 controls, 69 IFN cases) for miR-26 expression analysis and 118 cases (59 controls, 59 IFN cases) for survival analysis. The remaining 79 HCC cases (40 controls, 39 IFN cases) from another prospective RCT (cohort 3: IFN validation cohort) were used to validate the association between miR-26 and interferon therapy (4). Additional methodology is described in detail in the Supplementary Appendix.

Characteristics of the Patients

The study involved two independent cohorts consisting of 376 patients from the Liver Cancer Institute in Shanghai (Table 1) and an additional IFN validation cohort (FIG. 4—Supplemental Table 1) from the University of Hong Kong, all with histologically-confirmed HCC and a majority (90.5%) of hepatitis B virus (HBV) chronic carriers. Cohort 1 consisted of 241 patients, while cohort 2 consisted of 135 patients who participated in a prospective RCT of interferon therapy (3). Cohort 3 consisted of 79 HCC patients from another prospective RCT of interferon therapy (4). All patients received liver resections with curative intent. A majority of the patients were males (85.1%), with cirrhosis (88.1%), elevated serum AFP (62.2%) and a solitary presentation (84.4%). Clinical variables were similar between test and validation cohorts, with the exception of serum alanine transaminase (ALT) level, TNM staging and adjuvant therapy. Liver inflammation activity in these HBV-related HCC patients, as indicated by ALT levels, was significantly lower in cohort 2 cases than cohort 1 or cohort 3 and more early stage HCC cases were found in cohort 2. In addition, 39 patients in cohort 1 received prophylactic adjuvant therapies, but the responses appeared minimum (p=0.9; log rank test). In contrast, 53.3% of patients in cohort 2 and 49.4% in cohort 3 received an 'intent-to-cure' IFN adjuvant therapy, which improved overall survival (3; 4).

Gender-Related MicroRNAs and Clinical Outcome

To search for differentially expressed microRNAs between male and female liver samples, we globally analyzed the microRNA expression profiles of 241 cases from cohort 1, where both tumor (T) and non-tumor (NT) microRNA array data were available (GEO accession number, GSE6857) (22). To avoid potential confounding factors, an age-matched and balanced case set was used to identify gender-dependent microRNAs, which contained all female cases (n=30) and two age-matched male groups, i.e., G1 (n=31) and G2 (n=31). The clinical characteristics of female cases and male G1 or G2 cases were similar (FIG. 4C—Supplemental Table 2).

Class comparison analysis revealed that 15 (female vs. male G1) or 45 (female vs. male G2) microRNAs were differentially expressed in NT tissues, while 7 overlapped. In contrast, only one overlapping microRNA, miR-129-2, was found in tumors (FIG. 6A—Supplemental Table 3). Therefore, there were more consistent differences in microRNA expression in hepatic microenvironments than in tumors.

Among the overlapping microRNAs, miR-26a-1 was chosen for further analysis since its level was most significantly different between genders and was most abundant. Analysis with cohort 1 cases showed that miR-26a-1 level was significantly higher in female livers than males (FIG. 1A).

This was validated by mature miR-26 expression in female cases (n=26) and age-matched male cases (n=56) using qRT-PCR (FIG. 1B).

The inventors herein then reasoned that miR-26 may act as a gender-dependent tumor suppressor gene and if so, silencing of miR-26 would be a frequent event in tumors. Analyses showed that a significant reduction of miR-26a-1 in T compared to NT samples was observed in only low miR-26 cases (p<0.001) but not in high miR-26 cases (p=0.23) (FIG. 1C) when 224 HCC cases were dichotomized (low or high miR-26 based on the median level of miR-26a-1 in tumors).

The median fold change (T/NT ratio) was 0.37 in low miR-26a-1 cases and 0.98 in high miR-26a-1 cases, suggesting that silencing of miR-26 was only associated with low miR-26 cases. Moreover, the low miR-26 cases were associated with poor survival (FIG. 1D).

Figures 7A, 7B, 7C, 7D, 7E, 7F:
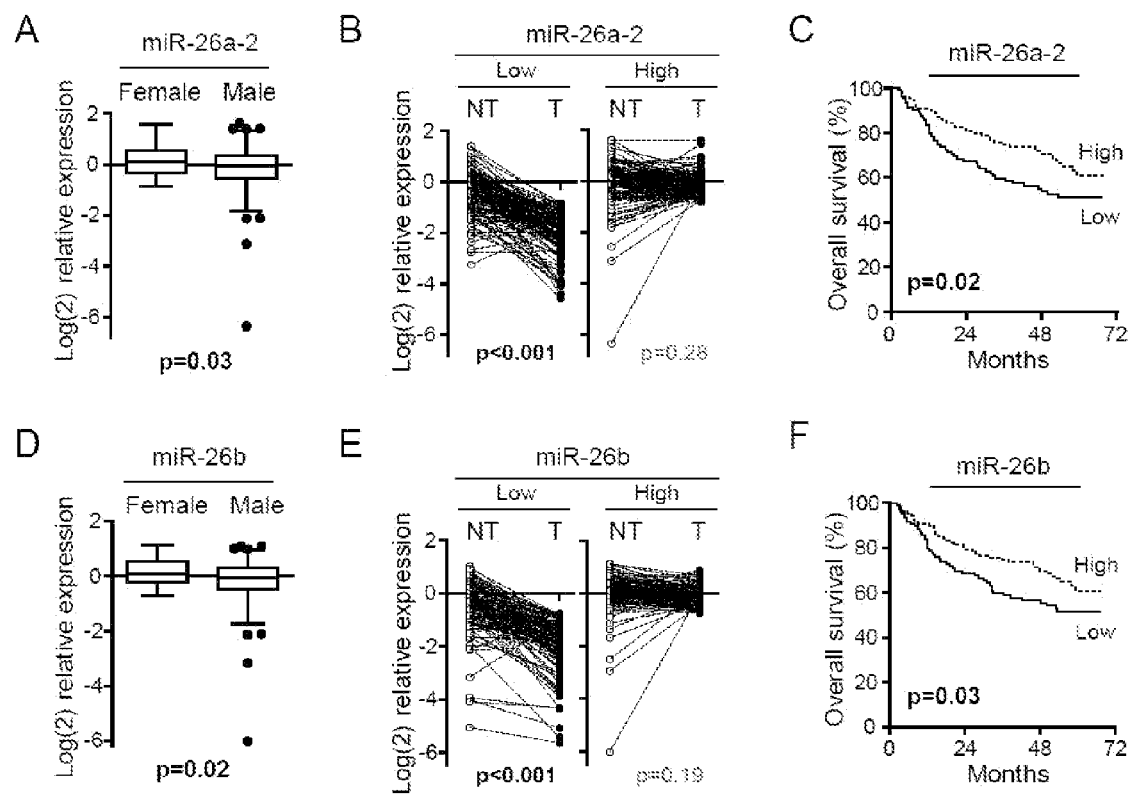
FIGS. 7A-7F: The abundance of miR-26 expression in male and female hepatic tissues and tumors from the test cohort.

In humans, there are three miR-26 members, i.e., miR-26a-1, miR-26a-2 and miR-26b. These microRNAs are evolutionarily highly conserved with 26a-1 and 26a-2 sharing an identical mature sequence, suggesting their functional redundancy. The expression patterns of all three miR-26 members and their associations with survival were similar (FIG. 7).

The inventors herein now show that miR-26 members were more abundantly expressed in female livers and their silencing may be important in the development of a subset of HCCs with poor outcome.

Distinct Gene Expression Patterns are Associated with Low miR-26 HCCs

Figure 2A:
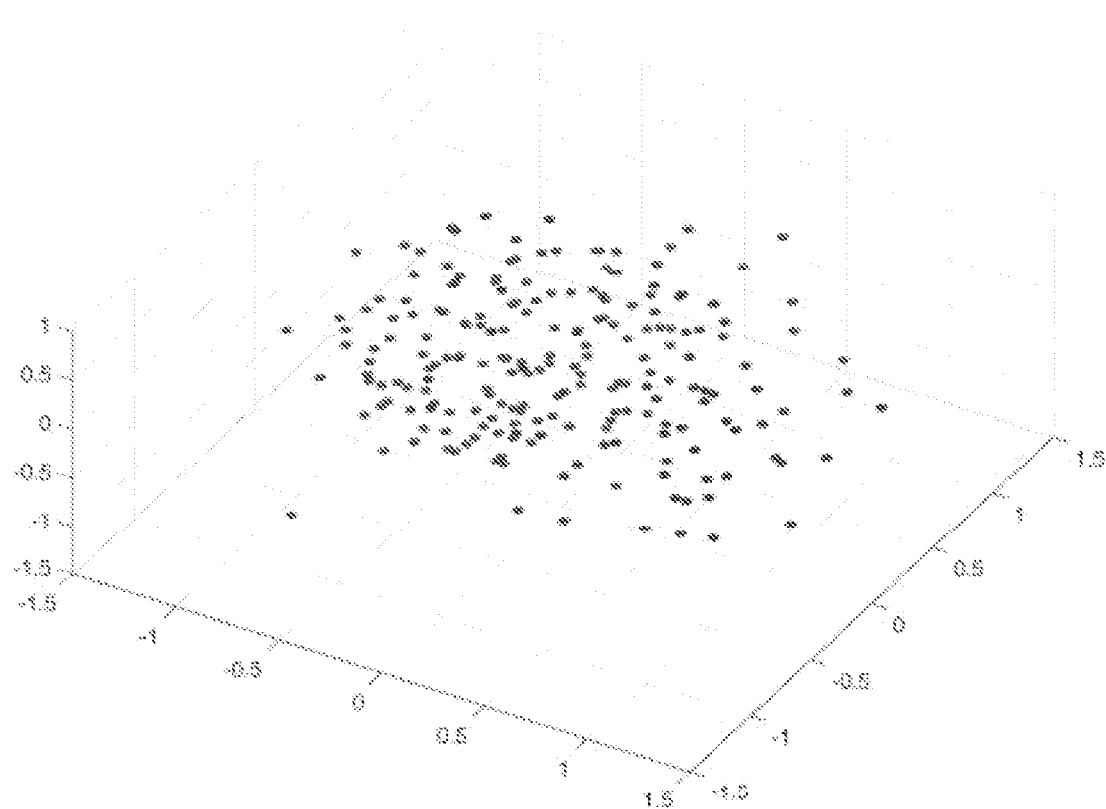
FIGS. 2A-2C: Distinct transcriptional activities in low miR-26 HCCs.
Figure 8:
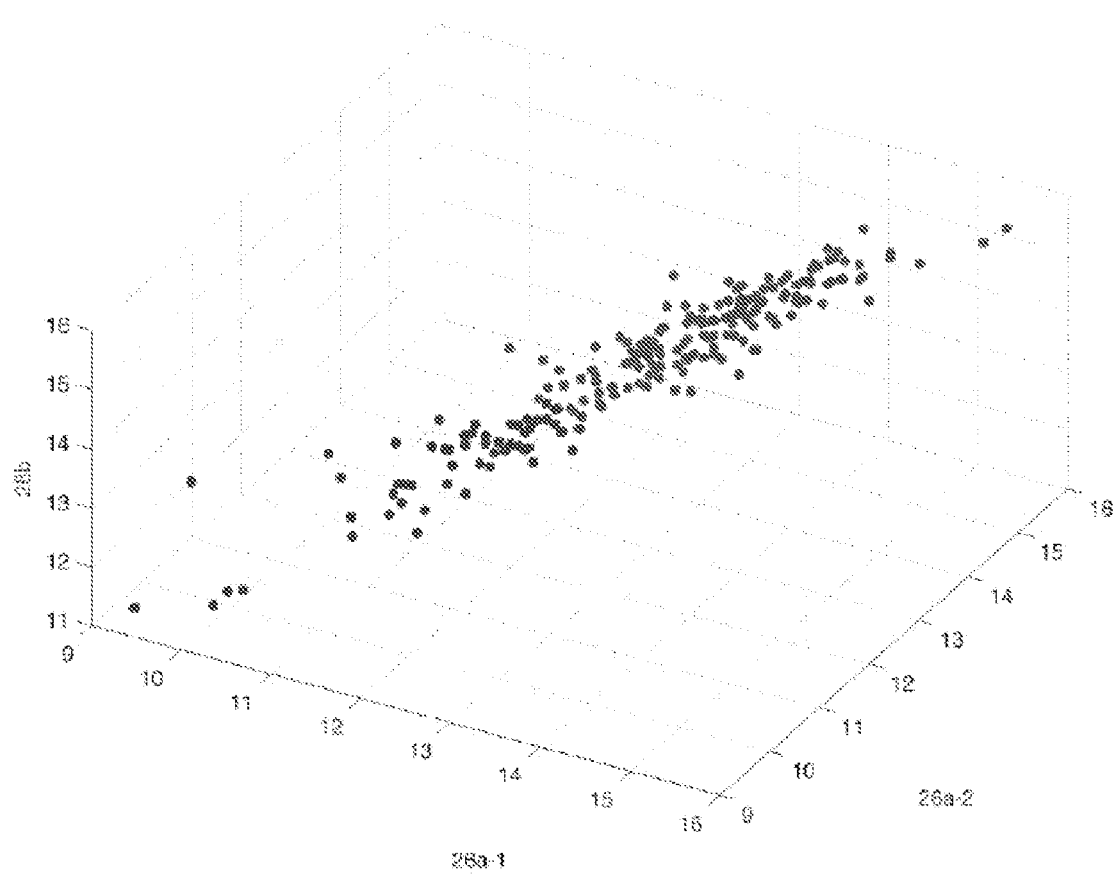
FIG. 8: Sample stratification based on miR-26 expression status. HCC samples were classified based on their average microRNA expression (i.e., miR-26a-1, 26a-2, and 26b). Median expression was used to separate cases into low miR-26 (blue or light) and high miR-26 (red or dark). The position of each dot (case) is determined by three microRNA expression levels (miR-26a-1, miR-26a-2 and miR-26b). The stratification outcomes were used to generate the MDS plot.

To test whether that the low miR-26 HCCs may be biologically distinct, the inventors herein analyzed 224 matched HCC cases with available microRNA and mRNA microarray data. The mRNA microarray data were based on the expression of ~21,000 mRNA genes (GEO accession number, GSE5975) (27). Multidimensional scaling analysis, based on the first three principal components of all genes, revealed that a majority of low miR-26 cases clustered separately from high miR-26 cases (FIG. 2A), according to the dichotomized expression status of the three miR-26s (FIG. 8).

Figure 2B:
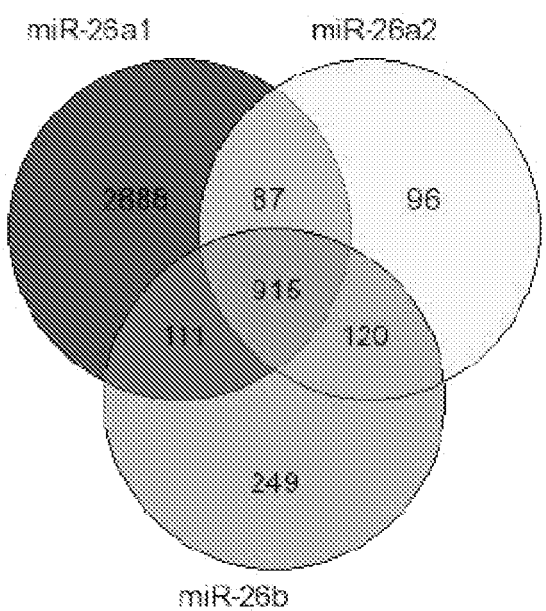

Class comparison analysis showed that the expression of a significant number of genes differed in tumors between low and high miR-26s groups and 915 genes were in common (FIG. 2B).

Figures 9A, 9B:
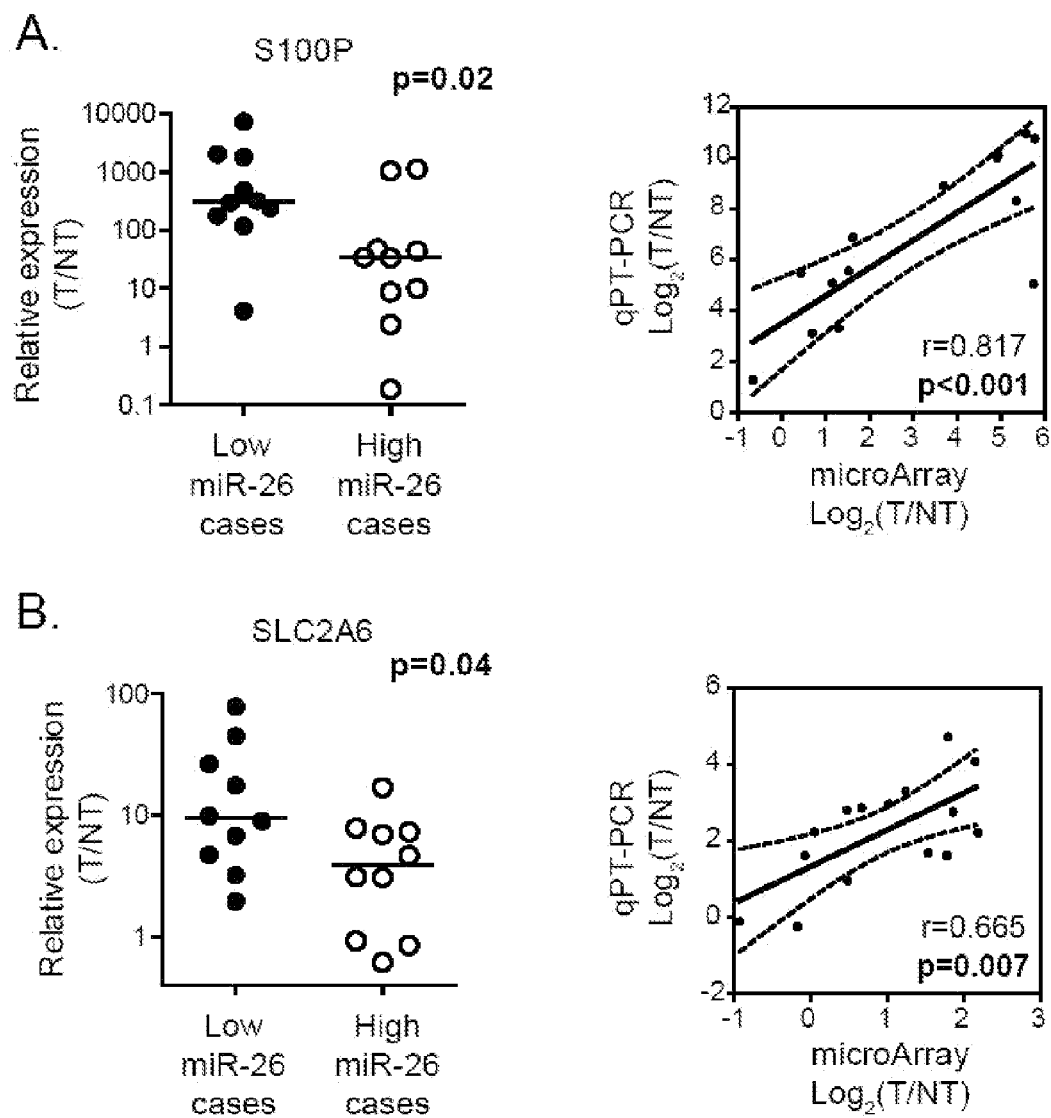
FIGS. 9A-9B: Expression of S100P and SLC2A6 in HCC and their correlation between microarray and qRT-PCR. Expression levels of S100P (FIG. 9A) and SLC2A6 (FIG. 9B) in 10 HCCs with low-miR-26 level and 10 HCC cases with high miR-26 level determined by qRT-PCR (left panel). A linear regression and correlation among data from qRT-PCR versus microarray is shown with r (spearman) and p-value indicated (right panel). Expression status is shown as the tumor (T)/non-tumor (NT) ratio.

SLC2A6 and S100P were selected among the differentially expressed genes for validation by qRT-PCR (FIG. 9).

Further, a multivariate class prediction analysis resulted in a significant class prediction of low miR-26 cases with 80.3% overall accuracy. Thus, low miR-26 HCC cases are distinct in their gene expression patterns compared to high miR-26 HCC cases.

Among the 915 overlapping genes, 770 were overexpressed in low miR-26 HCCs. Gene network analyses using these 770 genes revealed a series of putative tumorigenesis-networks with a high score (>10) (FIG. 6B—Table 4).

Figure 2C:
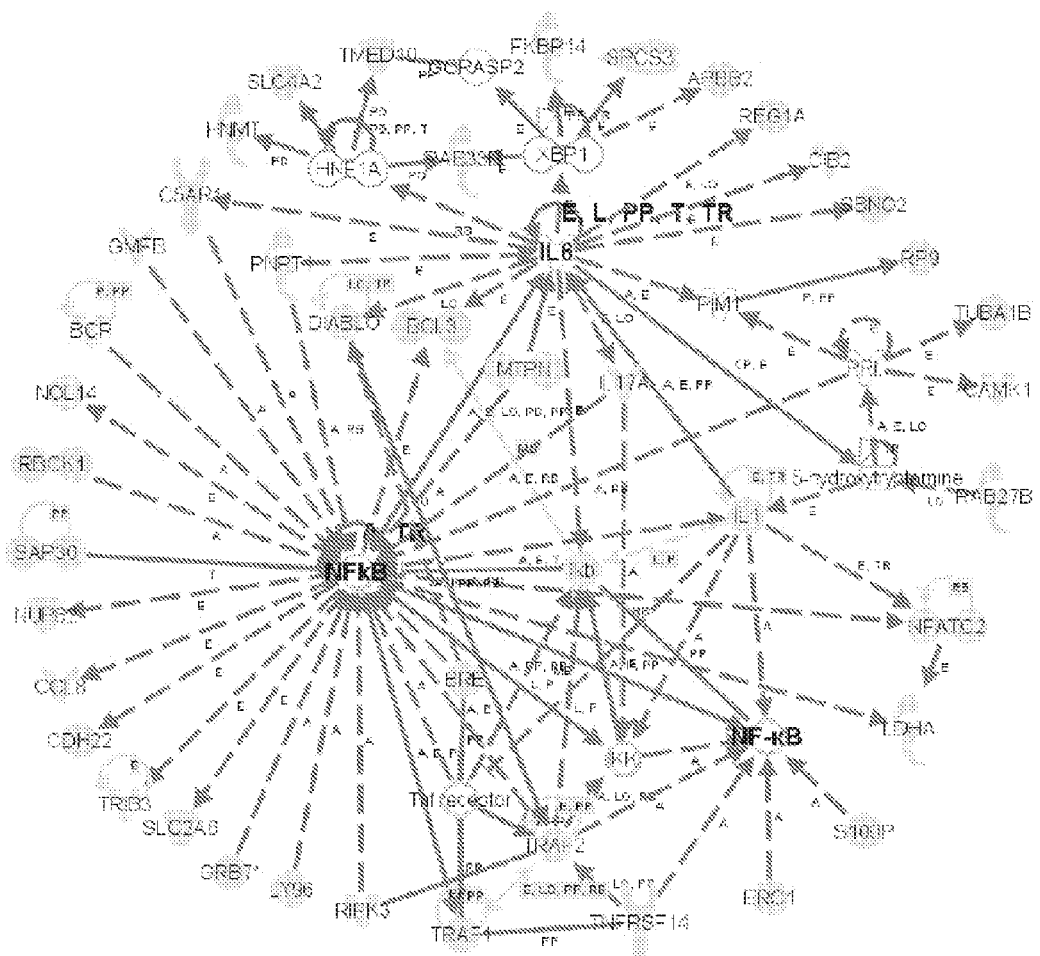

Examination of the enriched genes in various categories revealed several significant signaling networks, the most striking of which showed a predominant activation of the NFκB/IL-6 signaling pathway in low miR-26 cases (FIG. 2C).

Figure 10A:
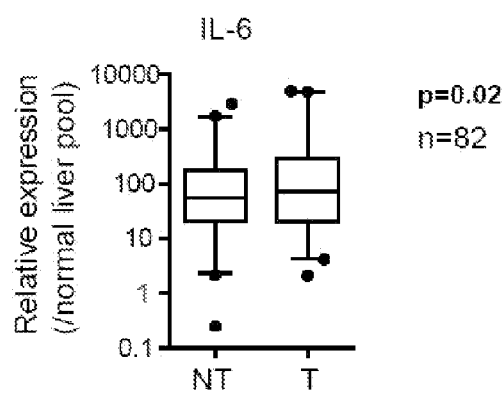
FIGS. 10A-10C: Expression of miR-26 and IL-6 in HCC.
Figure 10B:
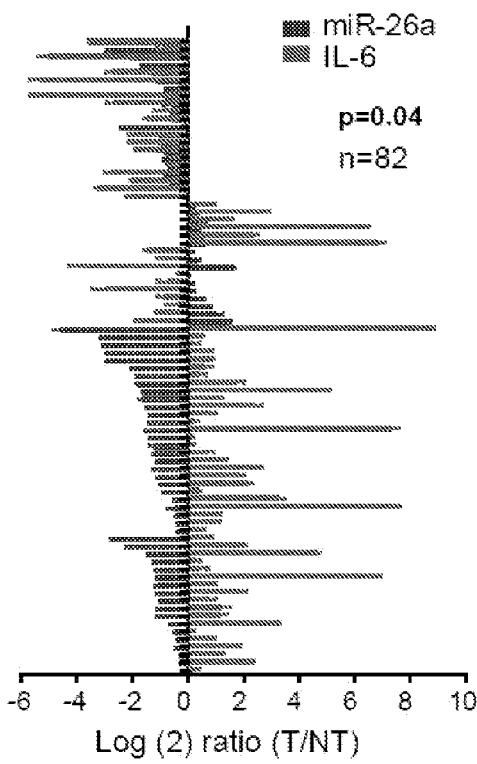
Figure 10C:
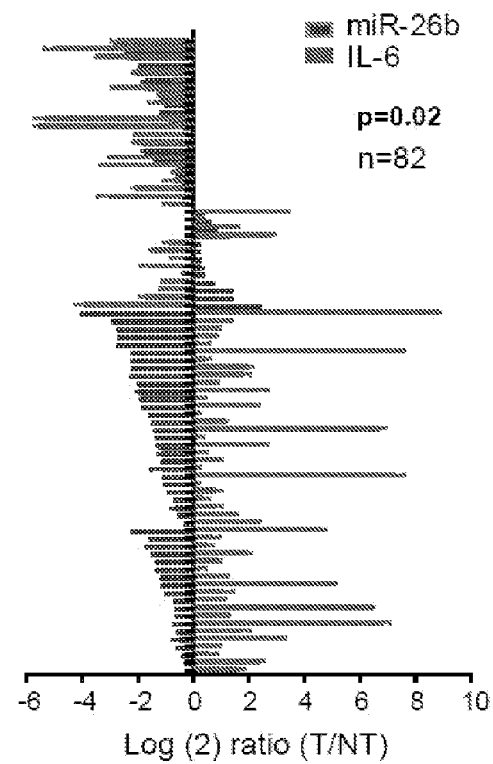

We measured the level of the NFκB target gene, IL-6, by qRT-PCR, as it was related to HCC and HCC gender disparity. Most of the HCC cases with a reduced miR-26 level had a concomitant elevation of IL-6 expression (FIG. 10). Taken together, these data show that low miR-26 HCCs have a distinct gene profile.

Validation with Independent Cohorts

Figure 11:
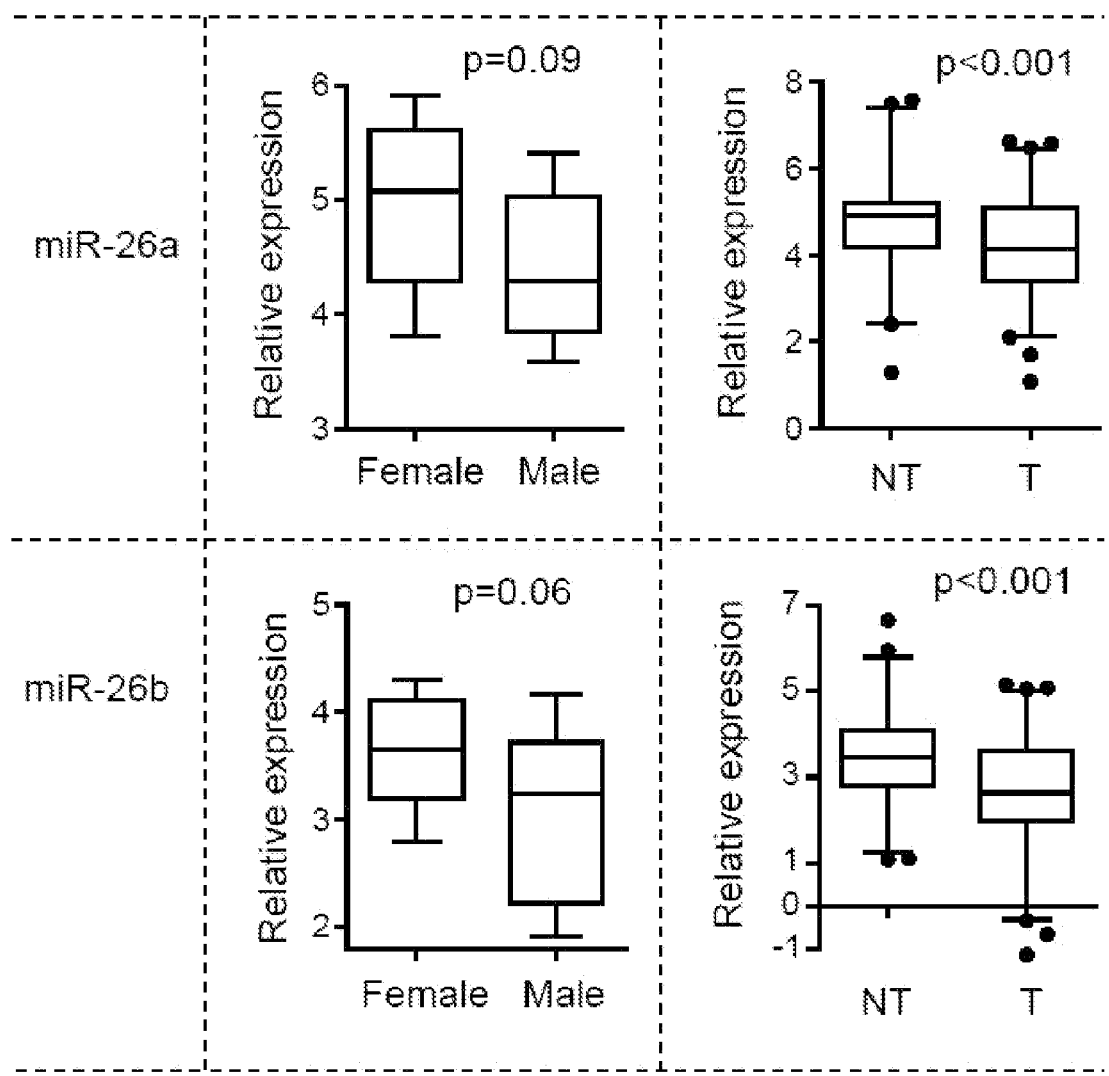
FIG. 11: The abundance of miR-26 expression in male and female hepatic tissues and tumors from a validation cohort. Decreased expression of miR-26a and miR-26b in tumors (right panels) with a more abundant expression in female than male non-tumor tissues (left panels) is validated in an independent validation cohort from a retrospective randomized clinical trial. Expression levels of miR-26a and miR-26b were measured by qRT-PCR. P values are from un-paired t-tests.

To validate the association of gender-dependent miR-26s with survival, we detected mature miR-26s by qRT-PCR in T and NT tissues from cohort 2. As IFN adjuvant therapy altered survival outcome, we analyzed the control group. Consistent with cohort 1, miR-26 expression was more abundant in female NT tissues but a significant reduction was observed in tumors, regardless of gender (FIG. 11).

Figures 3A, 3B, 3C, 3D, 3E, 3F:
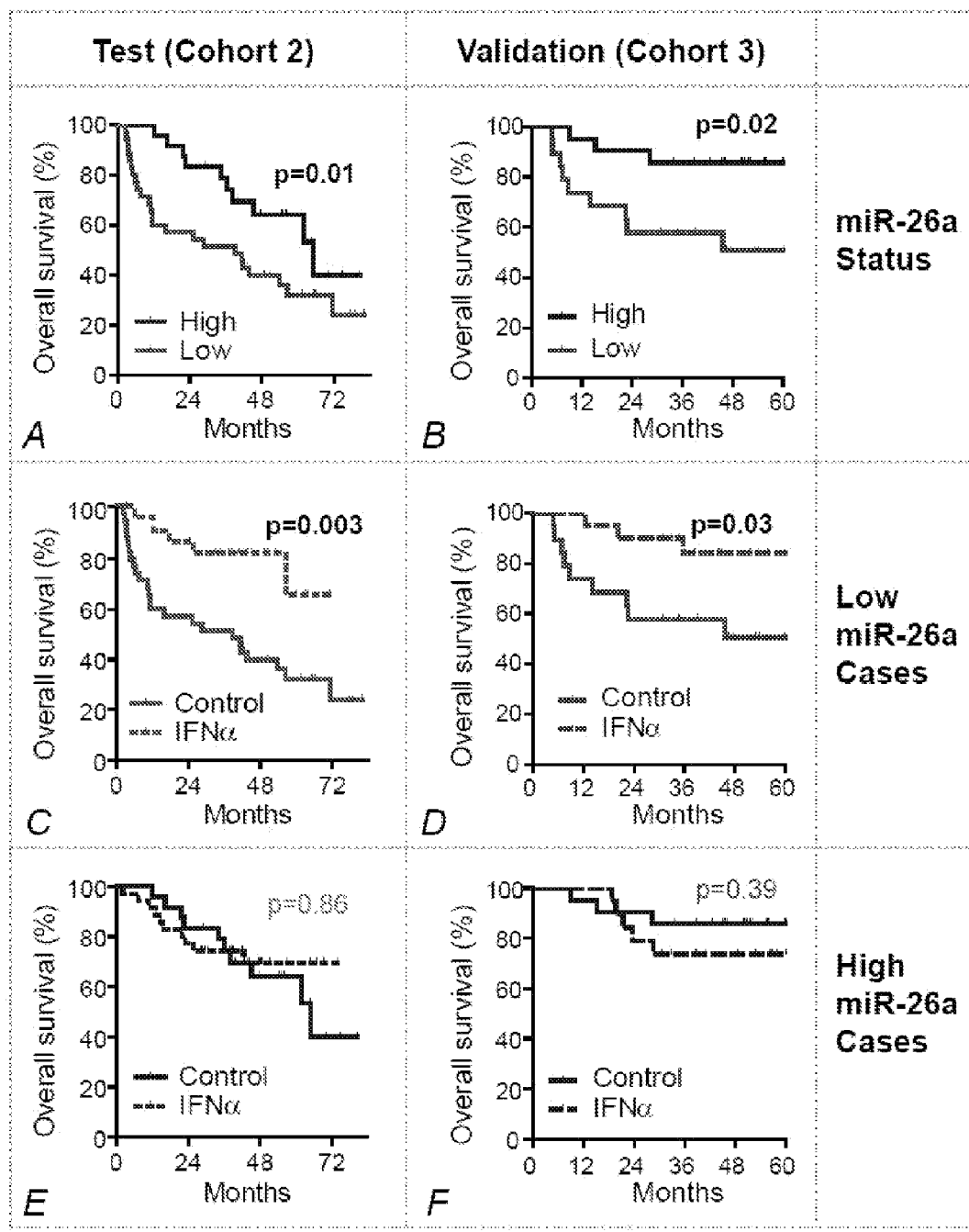
FIGS. 3A-3F: The association of miR-26a expression in tumors with survival prognosis in two prospective randomized control trials with IFN treatment (IFN test cohort, n=118; IFN validation cohort, n=79).
Figures 12A, 12B, 12C, 12D, 12E, 12F:
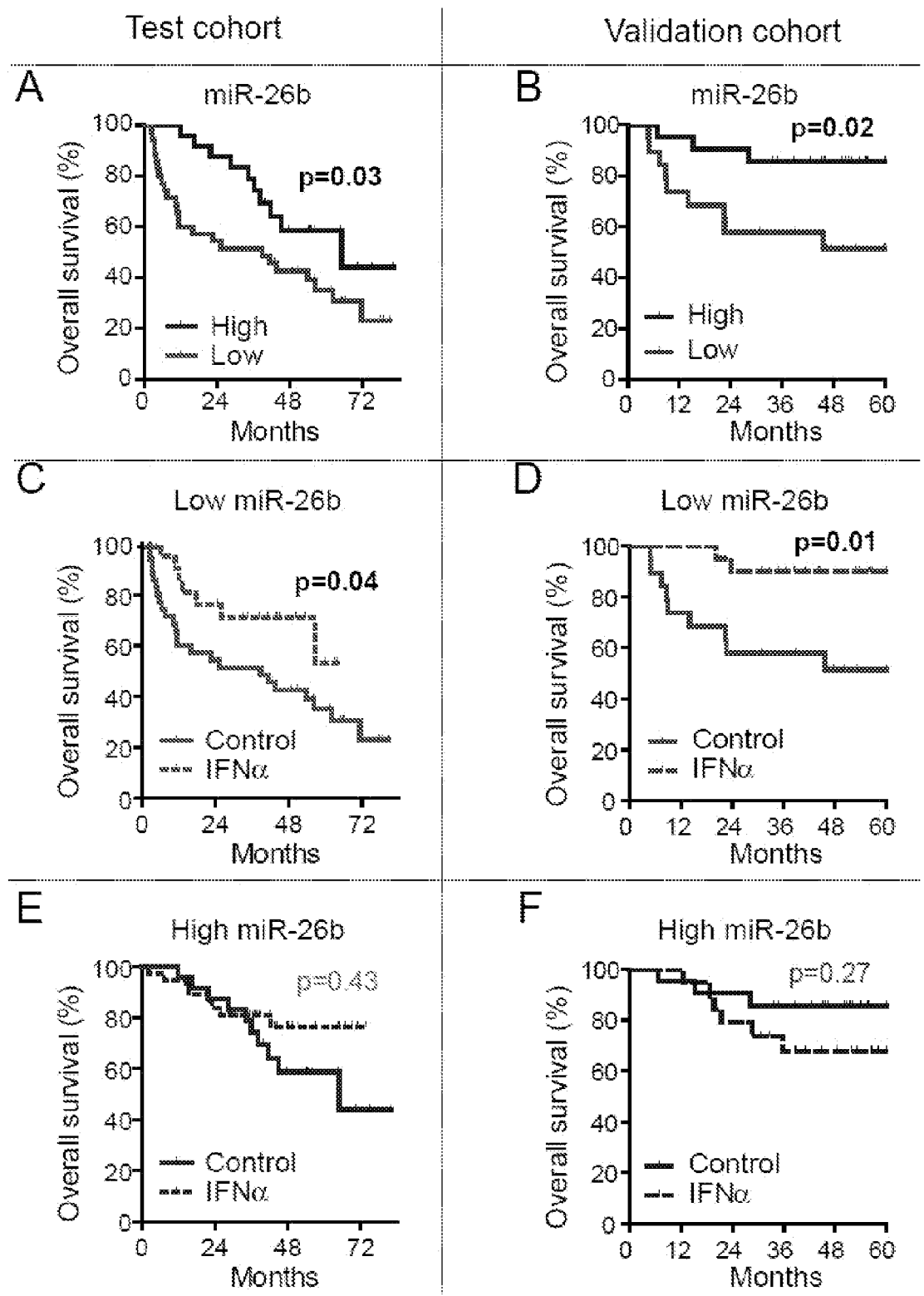
FIGS. 12A-12F: The association of miR-26b expression in tumors with survival prognosis in two prospective randomized control trials for IFN adjuvant therapy.

Moreover, low miR-26 expression in tumors was significantly associated with poor patient survival (FIG. 3A, FIG. 12A).

Another independent cohort (cohort 3) showed consistent results (FIG. 3B, FIG. 12B).

Cox proportional hazards regression analysis was used to further evaluate the association of miR-26 expression with prognosis in controls among cohort 2 (Table 2).

In univariate analysis, low miR-26a tumor expression and TNM staging were significantly associated with prognosis. The final multivariate model revealed that low miR-26a expression in tumors was an independent predictor of poor survival. A similar trend was found for miR-26b. Thus, the dichotomized miR-26 expression values were independent predictors of prognosis.

miR-26 Expression and Therapeutic Outcome

Low miR-26 HCCs appeared to be biologically distinct with an enrichment of genes functionally linked to immunobiology including those in the NFκB/IL-6 pathway. While not wishing to be bound by theory, the inventors herein now believe that such a tumor may be 'addictive' in its response to cytokine-mediated activity. Since cohort 2 consisted of cases treated with IFN, the inventors analyzed associations between miR-26 expression and therapeutic outcome.

Patients with low miR-26a expression in tumors had a significantly improved overall survival after receiving IFN adjuvant therapy when compared to those in the control group (p=0.003) (FIG. 3C), which was validated in cohort 3 (FIG. 3D).

In contrast, patients with high miR-26a expression from both cohorts did not respond to IFN (FIGS. 3E-3F).

Similar results were obtained with miR-26b expression (FIG. 12C-12F). Cox proportional hazards regression analysis was used to evaluate the effect of treatment on survival in low miR-26 groups of cohort 2 (FIG. 5B-Table 3).

In both univariate and multivariate analyses, TEN treatment was associated with a significantly improved survival in the low miR-26 group. An interaction analysis between miR-26 expression, IFN treatment, and survival also showed that miR-26 expression significantly affects IFN-associated survival outcome in these two cohorts (miR-26a, p=0.004; miR-26b, p=0.02). Thus, miR-26 is an independent predictor of IFN response.

DISCUSSION

This is the largest study to date analyzing gender-dependent microRNA profiles in HBV-related HCCs and their predictive values in survival prognosis and therapeutic outcomes using three independent cohorts.

The inventors herein have not shown that miR-26s were more abundantly expressed in female hepatic tissues, but their expression was significantly downregulated in a subset of HCCs compared to their paired non-cancerous tissues regardless of gender. These results indicate that miR-26s are gender and tumor-related microRNAs.

Also, tumors with reduced miR-26 expression had a distinct gene expression profile, and cases with low miR-26 expression had poor prognosis but responded favorably to IFN therapy.

Figure 13:
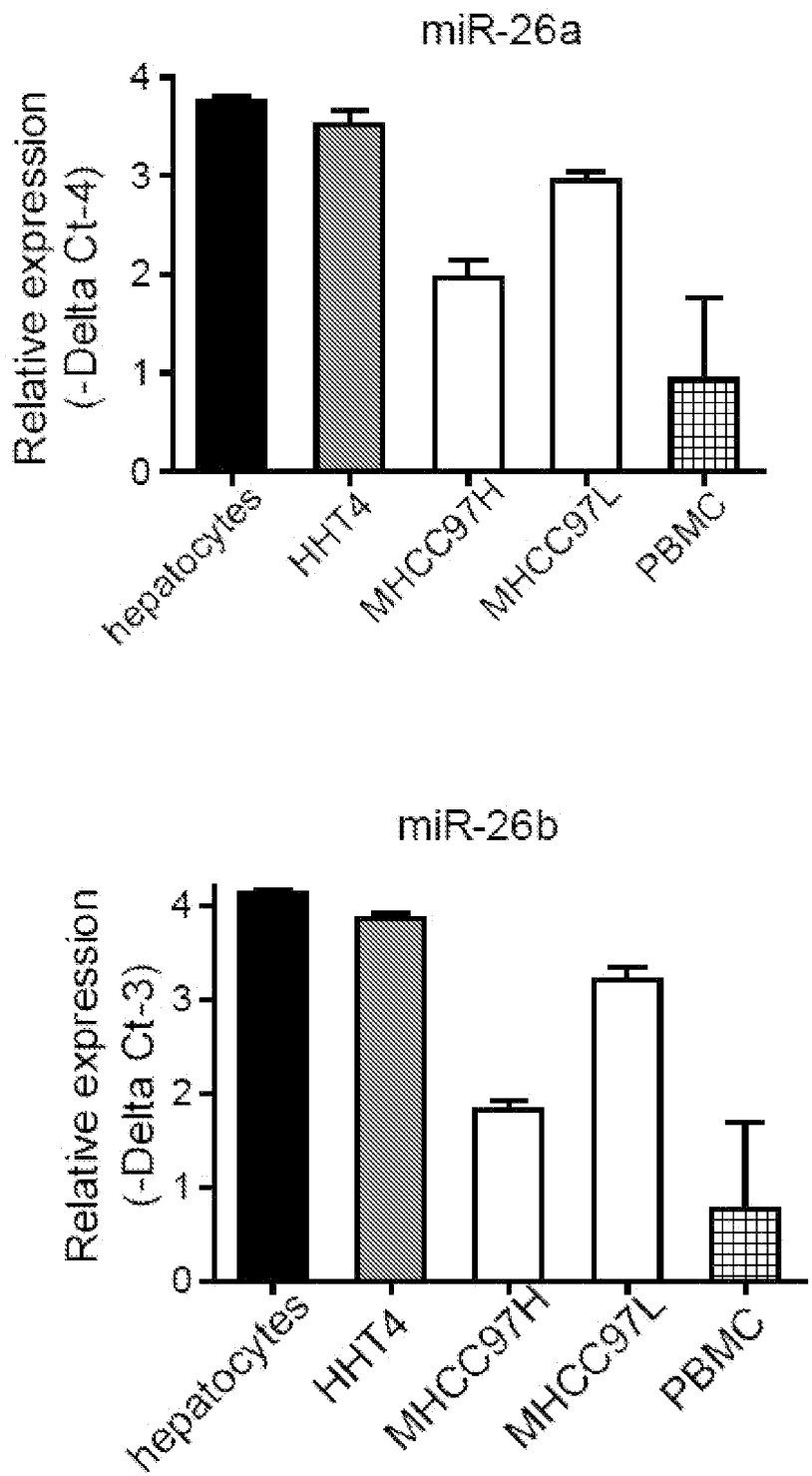
FIG. 13: Expression of miR-26 in various cell types including primary freshly isolated hepatocytes, hTERT-immortalized normal hepatocyte cell line HHT4, two HCC cell lines and PBMC from health donors determined by qRT-PCR.

These results show that miR-26 may be a tumor suppressor. miR-26 silencing in hepatocytes can contribute to male predominance in the development of an aggressive HCC. The following findings are consistent with the inventors' hypothesis above: (1) miR-26 is expressed at higher levels in female livers, where presumably more anti-carcinogenic activities exist; (2) miR-26 expression is silenced in a subset of HCCs with poor survival; (3) Genes activated in low miR-26 HCCs are selectively enriched in NFκB/IL-6 signaling pathways. (4) miR-26 is expressed more abundantly in hepatocytes and immortalized/non-transformed hepatocytes than in HCC cells and PBMC (FIG. 13).

Gender disparity of liver cancer was recently found to be due to gender differences in MyD8-dependent IL-6 induction by NF-κB in mice (13). Intriguingly, estrogens inhibit IL-6 promoter activity, which may contribute to a decreased susceptibility to HCC in females.

Figure 14:
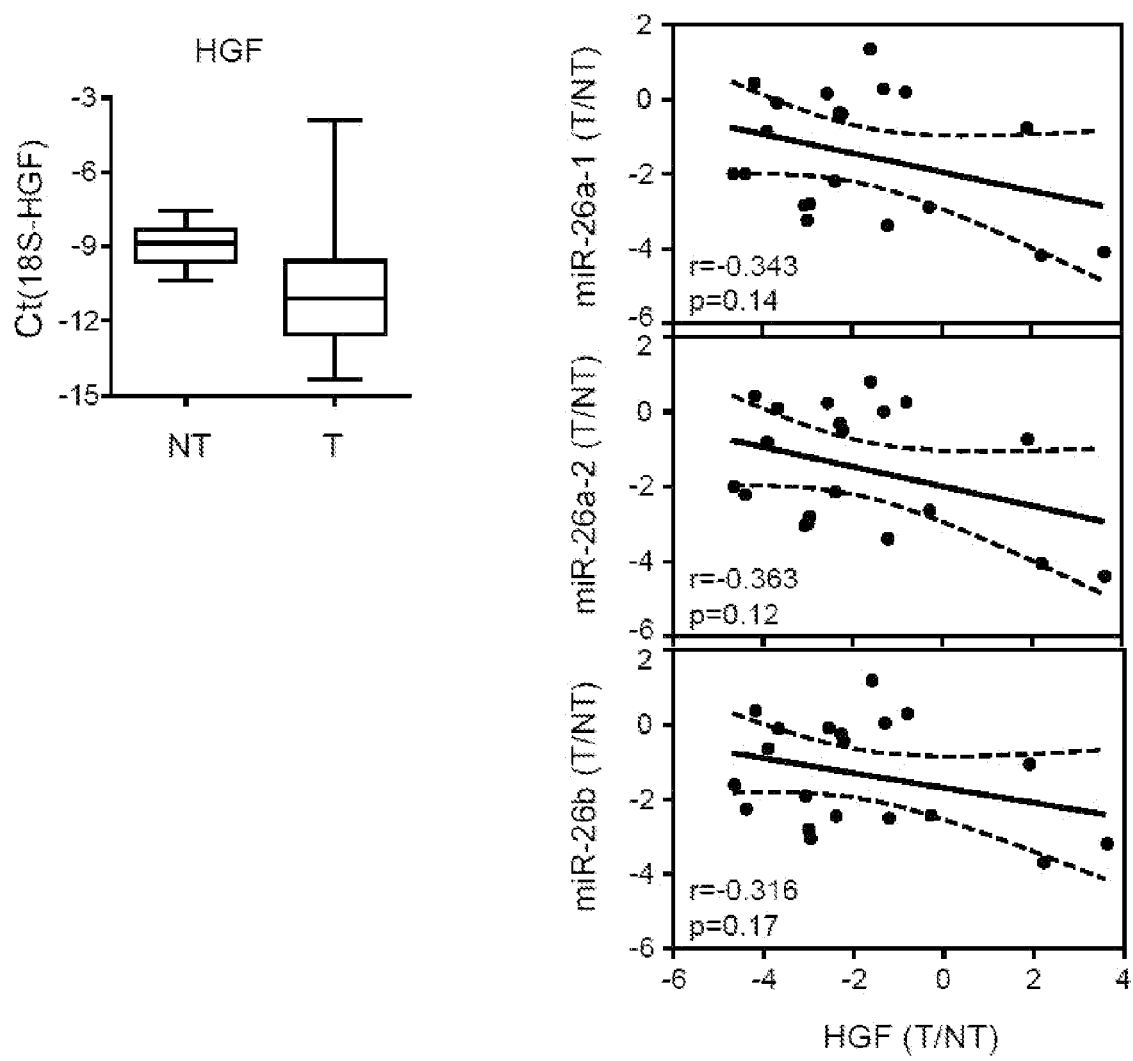
FIG. 14: Expression of HGF in HCC and association with miR-26. Expression levels of HGF in 10 HCCs with low-miR-26 level and 10 HCC cases with high miR-26 level determined by qRT-PCR (left panel). A linear regression and correlation between HGF level from qRT-PCR and miR-26 levels from microarray is shown with r (spearman) and p-value indicated (right panel). Expression status is shown as the tumor (T)/non-tumor (NT) ratio.
Figure 15:
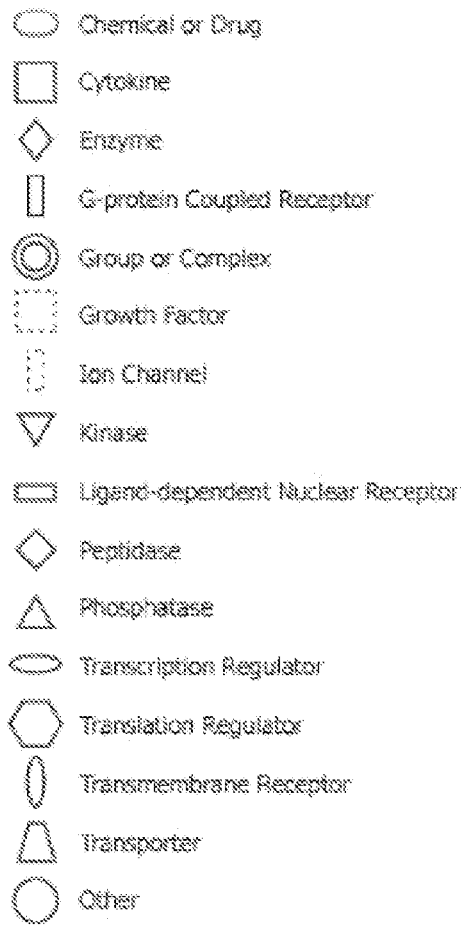
FIG. 15: A detailed description of the network relationships and network shapes used in the Pathway Analysis.

These are consistent with these findings as IL-6 expression was inversely correlated with miR-26. Moreover, many genes activated in low miR-26 HCCs can function in inducing progesterone, but inhibit estrogen signaling (networks 5 and 15, FIG. 6B—Supplemental Table 4). Interestingly, miR-26 expression was not associated with hepatic growth factor (HGF), another important factor in HCC (FIG. 14).

The inventors' herein analyses revealed that miR-26 was an independent predictor of survival. However, when therapy outcomes from IFN treatment were stratified, only patients with low miR-26 expression in tumors responded favorably to IFN therapy in two independent prospective RCTs.

These results indicate that miR-26 status in tumors is a useful clinical tool in HCC patient prognosis and in assisting selection of appropriate HCC patients who can benefit from IFN adjuvant therapy to prevent relapse.

Currently, recurrence-related mortality is a significant clinical problem for HCC patients who receive surgery and a single agent is not available as standard care at an adjuvant setting. Encouragingly, Clavien evaluated the adjuvant effects of IFN after liver resection or tumor ablation in 7 RCTs and concluded that all of these trials showed modest beneficial effects, but an improvement is clearly needed (5). In addition, among multiple experimental agents, only a modest survival benefit is observed with sorafenib (6). The poor efficacy of current systemic therapeutic agents may be caused by an inability to select a subpopulation of patients who may respond most favorably to a particular HCC therapy.

For the first time, these results provide a solution to this problem. The results described herein now have led to a rediscovery of a 'historical' agent, i.e., IFN, whose traditional modest therapeutic benefit may now be shifted to an agent with great potential.

Due to the robustness of the miR-26 predictor, IFN can be used as a first line therapy for HCC patients who receive resection and have tumors with reduced miR-26 expression, which will need to be evaluated in prospective studies. It should be noted that the studies presented here were mainly from HBV-positive (~90%) Chinese HCC patients, and will therefore need to be evaluated in non-Asian HCCs and HCCs arising from other underlying liver diseases such as hepatitis C and/or alcohol.

While the mechanism(s) behind the sensitivity of low miR-26 HCC cases to IFN treatment is currently unclear, the inventors herein believe that these HCCs represent a unique type of tumor with a specific activation of the IFN-responsive signaling pathway. Consistently, low miR-26 HCCs were distinct from high miR-26 HCCs and had poor survival prognosis. Many of the overexpressing genes in low miR-26 HCCs are related to cell immunity such as those encoding pro- and anti-inflammatory cytokines (i.e., IL-1, IL-2, IL-10 and IL-17).

Moreover, many signaling networks activated in low miR-26 HCCs are immune-associated such as NFκB/IL-6, IL-10, STAT3 and IFN-inducible factor signaling networks.

Again, while not wishing to be bound by theory, the inventors herein believe that tumors with low miR-26 expression may have a unique activation of IFN signaling, potentially through NFκB/IL-6 signaling pathway, and thus may be sensitive to IFN-mediated growth inhibition via IL-6/STAT3 signaling (29).

Now described herein is the identification of systematic differences in microRNA expression patterns between male and female liver tissues derived from HCC patients. Tumors with a reduced miR-26 expression were biologically distinct, had poor survival outcome, but responded favorably to adjuvant IFN therapy. These data indicate that miR-26 is a useful diagnostic and prognostic biomarker for HCC and can assist in selecting patients who can significantly benefit from adjuvant IFN therapy.

Example II

RNA Isolation and Real-Time qRT-PCR Analysis

Total RNAs were extracted from frozen tissues of cohort 1 using standard TRIZOL (Invitrogen, Carlsbad, Calif.) methods, and from paraffin-embedded tissues of cohort 2 and cohort 3 using a MasterPure RNA Purification Kit (Epicenter, Madison, Wis.). The expression of mature microRNAs was measured using Taqman MicroRNA Assays specific for miR-26a and miR-26b after reverse transcription (Applied biosystems, Foster City, Calif.). All comparisons between strata (gender. miR etc) were within each cohort. The Taqman MicroRNA Assay for U6 RNA was used to normalize the relative abundance of microRNAs. The expression of IL-6 was measured using the Taqman Gene Assay specific for this gene after reverse transcription by using the High Capacity cDNA Archive Kit (Applied Biosystems, Foster City, Calif.). The Taqman gene assay for 18 s was used to normalize the relative abundance of mRNA. The experiments were performed in triplicate.

Microarray Analyses and Statistics

For microRNA microarray profiling, tumors and paired non-tumor tissues were profiled separately using a single channel array platform previously described (22). The array quality control, data preprocessing and normalization were done essentially as previously described (22). The BRB-ArrayTools software 3.6.0 (http://linus.nci.nih.gov) was used for microarray analyses as previously described (25; 26). MicroRNA probes with values missing from more than 50% of the arrays and those with less than 20% of expression data values having at least a 1.5-fold change in either direction from the probe's median value were excluded from the analysis, which left 624 probes. Class comparison analysis using t-statistics was used to identify microRNAs that were differentially expressed in tumors or surrounding non-cancerous tissues between males and females.

For this analysis, the initial significance threshold of univariate tests was set at p<0.05 and the analyses were based on 1000 permutations for the multivariate test to generate permutation p-values for the global test to control false discovery rates. For mRNA expression microarray profiling, the inventors used their our previously available oligoarray dataset based on a dual-channel platform (i.e., T/NT ratio) (27) that contained 224 cases matched to those with available microRNA microarray data described above. The inventors used the median expression in tumors to dichotomize HCC cases, where low miR-26 expression was classified as the lower 50th percentile and high miR-26 expression was classified as the upper 50th percentile. Class comparison analysis based on dichotomized miR-26 expression levels was used to identify differentially expressed mRNAs between low miR-26 and high miR-26 HCCs. The same probe filtering criteria was followed as described above, leaving 11,580 expression probes for these comparisons.

Six class prediction algorithms, i.e., Support Vector Machines (SVM), Compound Covariate Predictor (CCP), Diagonal Linear Discriminant (DLD), 1-Nearest Neighbor (1NN), 3-Nearest Neighbor (3NN) or Nearest Centroid (NC), were also used to determine whether mRNA expression patterns could accurately discriminate low miR-26 HCCs from high miR-26 HCCs. In these analyses, 90% of the samples were randomly chosen to build a classifier which was then used to predict the remaining 10% of the cases. The accuracy of the prediction was calculated after 1000 repetitions of this random partitioning process to control the number and proportion of false discoveries. Hierarchical clustering analysis was performed using BRBarrayTools with median-centered correlation and complete linkage. Using an unsupervised approach, we also performed multidimensional scaling analysis using all cohort 1 samples based on the first three principal components of 11,580 genes that passed the filter. The expression levels of these genes were log-transformed, and Euclidean distance was used to determine their positions. Gene Network Analyses were used to identify signaling pathways that were enriched with genes differentially expressed in tumors between miR-26 low and miR-26 high HCCs using Ingenuity Pathways Analysis (Ingenuity®, www.ingenuity.com).

Kaplan-Meier survival analysis was used to compare patient survival based on dichotomized miR-26 expression, using GraphPad Prism software 5.0 (GraphPad Software, San Diego, Calif.) with statistical P values generated by the Cox-Mantel log-rank test. Cox proportional hazards regression analyses were used to analyze the effect of clinical variables on patient survival using STATA 9.2 (College Station, Tex.). A univariate test was used to examine the influence of each clinical variable on survival. A multivariate analysis was performed considering clinical variables from the univariate analysis that were significantly associated with survival with significance set at p<0.05. Multi-colinearity of the covariates was assessed and was not found to be present. In the final models, gender was included as a covariate due to its biological relevance in HCC outcome and its association with miR-26 expression. It was determined that the final models met the proportional hazards assumption. For RT-PCR data, the statistical P value, generated by the student t-test, and the Spearman correlation constant were calculated using GraphPad Prism Software 5.0. The statistical significance was defined as p<0.05. All p-values in this paper are two-sided.

Example III

Method of Treating HCC in Patients Exhibiting Low Expression of miR-26 in HCC Tumor Samples This example describes a method of selecting and treating HCC patients that are likely to have a favorable response to IFN-α treatment as an adjunctive therapy.

For some HCC patients, adjuvant therapies, such as IFN-α therapy can prolong survival (Sun et al., *J. Cancer Res. Clin. Oncol.* 132(7):458-465, 2006). However, it would be beneficial to identify patients that are most likely to benefit from IFN-α adjunctive therapy prior to initiating treatment.

It is now disclosed herein that the prognosis of HCC patients expressing low levels of miR-26 in HCC tumor samples relative to a control (such as non-cancerous liver tissue obtained from the same patient) significantly improves after treatment with IFN-α. In contrast, patients expressing high levels of miR-26 in tumor samples do not exhibit a significant increase in survival following IFN-α treatment and thus are not good candidates for such adjunctive treatment.

A patient diagnosed with HCC first undergoes liver resection with an intent to cure. HCC tumor and non-cancerous tissue samples are obtained from the portion of the liver tissue removed from the patient. RNA is then isolated from the tissue samples using any appropriate method for extraction of small RNAs that are well known in the art, such as by using TRIZOL™. Purified RNA is then subjected to RT-PCR using primers specific for miR-26 to determine the expression level of miR-26 in the tumor and non-cancerous tissues. If expression of miR-26 is at least 1.5-fold lower in the tumor tissue relative to the non-cancerous tissue, the patient is a candidate for IFN-α adjunctive therapy.

Accordingly, the patient is treated with a therapeutically effective amount of IFN-α according to methods known in the art (see, for example, Sun et al., *J. Cancer Res. Clin. Oncol.* 132(7):458-465, 2006; Qian et al., *Cancer* 107(7):1562-1569, 2006, both of which are herein incorporated by reference). The dose and dosing regimen of IFN-α will vary depending on a variety of factors, such as health status of the patient and the stage of the HCC. Typically, IFN-α is administered 1-3 times per week for up to about six months.

Example IV

Alternative Treatment Method for HCC Patients with Low Expression of miR-26

This example describes a method of treating a patient diagnosed with HCC and exhibiting low expression of miR-26 with interferon therapy in the absence of liver resection. To determine whether a patient diagnosed with HCC is a good candidate for IFN-α therapy, a HCC tumor sample is obtained from the patient that has not undergone liver resection, along with a non-cancerous liver tissue sample. The tissue samples can be obtained according to any method known in the art. For example, the tissue samples can be obtained by performing a biopsy procedure using a hypodermic needle to remove the desired tissues.

RNA is then isolated from the tissue samples using any appropriate method for extraction of small RNAs that are well known in the art, such as by using TRIZOL™. Purified RNA is then subjected to RT-PCR using primers specific for miR-26 to determine the expression level of miR-26 in the tumor and non-cancerous tissues. If expression of miR-26 is at least 1.5-fold lower in the tumor tissue relative to the non-cancerous tissue, the patient is a candidate for IFN-α therapy.

Accordingly, the patient is treated with a therapeutically effective amount of IFN-α according to methods known in the art (see, for example, Sun et al., *J. Cancer Res. Clin. Oncol.* 132(7):458-465, 2006; Qian et al., *Cancer* 107(7):1562-1569, 2006, both of which are herein incorporated by reference). The dose and dosing regimen of IFN-α will vary depending on a variety of factors, such as health status of the patient and the stage of the HCC. Typically, IFN-α is administered 1-3 times per week for up to about six months.

Example V

Method of Treating HCC in Patients Exhibiting High Expression of miR-26 in HCC Tumor Samples This example describes a method of treating a patient diagnosed with HCC if the patient exhibits a high level of expression of miR-26 in the HCC tumor.

A patient diagnosed with HCC first undergoes liver resection with an intent to cure. HCC tumor and non-cancerous tissue samples are obtained from the portion of the liver tissue removed from the patient. RNA is then isolated from the tissue samples using any appropriate method for extraction of small RNAs that are well known in the art, such as by using TRIZOL™. Purified RNA is then subjected to RT-PCR using primers specific for miR-26 to determine the expression level of miR-26 in the tumor and non-cancerous tissues. If expression of miR-26 is not at least 1.5-fold lower in the tumor tissue relative to the non-cancerous tissue, the patient is unlikely to respond favorably to IFN-α adjunctive therapy. Accordingly, the patient does not receive IFN-α therapy but is monitored for post-operative signs of disease recurrence.

Example VI

Methods of Diagnosing HCC Patients

In one particular aspect, there is provided herein a method of diagnosing whether a subject has, or is at risk for developing, hepatocellular carcinoma (HCC). The method generally includes measuring the level of at least one miR gene product in a test sample from the subject and determining whether an alteration in the level of the miR gene product in the test sample, relative to the level of a corresponding miR gene product in a control sample, is indicative of the subject either having, or being at risk for developing, HCC. In certain embodiments, the level of the at least one miR gene product is measured using Northern blot analysis. Also, in certain embodiments, the level of the at least one miR gene product in the test sample is less than the level of the corresponding miR gene product in the control sample, and/or the level of the at least one miR gene product in the test sample is greater than the level of the corresponding miR gene product in the control sample.

Example VII

Measuring miR Gene Products

The level of the at least one miR gene product can be measured by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal of at least one miRNA is indicative of the subject either having, or being at risk for developing, HCC.

Example VIII

Diagnostic and Therapeutic Applications

In another aspect, there is provided herein are methods of treating HCC in a subject, where the signal of at least one miRNA, relative to the signal generated from the control sample, is de-regulated (e.g., down-regulated and/or up-regulated).

Also provided herein are methods of diagnosing whether a subject has, or is at risk for developing, a HCC associated with one or more adverse prognostic markers in a subject, by reverse transcribing RNA from a test sample obtained from the subject to provide a set of target oligodeoxynucleotides; hybridizing the target oligodeoxynucleotides to a microarray comprising miRNA-specific probe oligonucleotides to provide a hybridization profile for the test sample; and, comparing the test sample hybridization profile to a hybridization profile generated from a control sample. An alteration in the signal is indicative of the subject either having, or being at risk for developing, the cancer.

Also provided herein are methods of treating HCC in a subject who has HCC in which at least one miR gene product is down-regulated or up-regulated in the cancer cells of the subject relative to control cells. When the one or more miR gene product is down-regulated in the cancer cells, the method comprises administering to the subject an effective amount of at least one isolated miR gene product, such that proliferation of cancer cells in the subject is inhibited. When one or more miR gene product is up-regulated in the cancer cells, the method comprises administering to the subject an effective amount of at least one compound for inhibiting expression of at least one miR gene product, such that proliferation of cancer cells in the subject is inhibited.

Also provided herein are methods of treating HCC in a subject, comprising: determining the amount of at least one miR gene product in HCC cells, relative to control cells; and, altering the amount of miR gene product expressed in the HCC cells by: administering to the subject an effective amount of at least one isolated miR gene product, if the amount of the miR gene product expressed in the cancer cells is less than the amount of the miR gene product expressed in control cells; or administering to the subject an effective amount of at least one compound for inhibiting expression of the at least one miR gene product, if the amount of the miR gene product expressed in the cancer cells is greater than the amount of the miR gene product expressed in control cells, such that proliferation of cancer cells in the subject is inhibited.

Example IX

Compositions

Also provided herein are pharmaceutical compositions for treating HCC, comprising at least one isolated miR gene product and a pharmaceutically-acceptable carrier. In a particular embodiment, the pharmaceutical compositions comprise at least one isolated miR gene product corresponds to a miR gene product that is down-regulated in HCC cells relative to suitable control cells. In certain embodiments, the miR gene product comprises one or more of the SEQ ID NOS: 1-5.

In another particular embodiment, the pharmaceutical composition comprises at least one miR expression regulator (for example, an inhibitor) compound and a pharmaceutically-acceptable carrier.

Also provided herein are pharmaceutical compositions that include at least one miR expression regulator compound that is specific for a miR gene product that is up- or down-regulated in HCC cells relative to suitable control cells.

Also provided herein are methods of identifying an anti-HCC agent, comprising providing a test agent to a cell and measuring the level of at least one miR gene product associated with decreased expression levels in HCC cells, wherein an increase in the level of the miR gene product in the cell, relative to a suitable control cell, is indicative of the test agent being an anti-HCC agent. In certain embodiments, the miR gene product comprises one or more of the SEQ ID NOS: 1-5.

Also provided herein are methods of identifying an anti-HCC agent, comprising providing a test agent to a cell and measuring the level of at least one miR gene product associated with increased expression levels in HCC cells, wherein a decrease in the level of the miR gene product in the cell, relative to a suitable control cell, is indicative of the test agent being an anti-HCC agent.

Example X

Kits

Any of the compositions described herein may be comprised in a kit. In a non-limiting example, reagents for isolating miRNA, labeling miRNA, and/or evaluating an miRNA population using an array are included in a kit. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. It may also include one or more buffers, such as reaction buffer, labeling buffer, washing buffer, or a hybridization buffer, compounds for preparing the miRNA probes, and components for isolating miRNA. Other kits may include components for making a nucleic acid array comprising oligonucleotides complementary to miRNAs, and thus, may include, for example, a solid support.

For any kit embodiment, including an array, there can be nucleic acid molecules that contain a sequence that is identical or complementary to all or part of any of SEQ ID NOS: 1-5.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being one preferred solution. Other solutions that may be included in a kit are those solutions involved in isolating and/or enriching miRNA from a mixed sample.

However, the components of the kit may be provided as dried powder(s). When reagents and/or components are provided as a dry powder, the powder can be reconstituted by the addition of a suitable solvent. It is envisioned that the solvent may also be provided in another container means. The kits may also include components that facilitate isolation of the labeled miRNA. It may also include components that preserve or maintain the miRNA or that protect against its degradation. The components may be RNAse-free or protect against RNAses.

Also, the kits can generally comprise, in suitable means, distinct containers for each individual reagent or solution. The kit can also include instructions for employing the kit components as well the use of any other reagent not included in the kit. Instructions may include variations that can be implemented. It is contemplated that such reagents are embodiments of kits of the invention. Also, the kits are not limited to the particular items identified above and may include any reagent used for the manipulation or characterization of miRNA.

It is also contemplated that any embodiment discussed in the context of an miRNA array may be employed more generally in screening or profiling methods or kits of the invention. In other words, any embodiments describing what may be included in a particular array can be practiced in the context of miRNA profiling more generally and need not involve an array per se.

It is also contemplated that any kit, array or other detection technique or tool, or any method can involve profiling for any of these miRNAs. Also, it is contemplated that any embodiment discussed in the context of an miRNA array can be implemented with or without the array format in methods of the invention; in other words, any miRNA in an miRNA array may be screened or evaluated in any method of the invention according to any techniques known to those of skill in the art. The array format is not required for the screening and diagnostic methods to be implemented.

The kits for using miRNA arrays for therapeutic, prognostic, or diagnostic applications and such uses are contemplated by the inventors herein. The kits can include an miRNA array, as well as information regarding a standard or normalized miRNA profile for the miRNAs on the array. Also, in certain embodiments, control RNA or DNA can be included in the kit. The control RNA can be miRNA that can be used as a positive control for labeling and/or array analysis.

The methods and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Example XI

Array Preparation and Screening

Also provided herein are the preparation and use of miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters.

Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample.

A variety of different array devices in which a plurality of distinct nucleic acid probes are stably associated with the surface of a solid support are known to those of skill in the art. Useful substrates for arrays include nylon, glass and silicon. The arrays may vary in a number of different ways, including average probe length, sequence or types of probes, nature of bond between the probe and the array surface, e.g. covalent or non-covalent, and the like. The labeling and screening methods described herein and the arrays are not limited in its utility with respect to any parameter except that the probes detect miRNA; consequently, methods and compositions may be used with a variety of different types of miRNA arrays.

In view of the many possible embodiments to which the principles of our invention may be applied, it should be recognized that the illustrated embodiments are only preferred examples of the invention and should not be taken as a limitation on the scope of the invention. Rather, the scope of the invention is defined by the following claims. We therefore claim as our invention all that comes within the scope and spirit of these claims.

REFERENCES

The references discussed above and the following references, to the extent that they provide exemplary procedural or other details supplementary to those set forth herein, are specifically incorporated herein by reference.

(1) Parkin D M, Bray F, Ferlay J, Pisani P. Global cancer statistics, 2002. CA Cancer J Clin 2005; 55(2):74-108.

(2) Llovet J M, Bruix J. Systematic review of randomized trials for unresectable hepatocellular carcinoma: Chemoembolization improves survival. Hepatology 2003; 37(2):429-442.

(3) Sun H C, Tang Z Y, Wang L et al. Postoperative interferon alpha treatment postponed recurrence and improved overall survival in patients after curative resection of HBV-related hepatocellular carcinoma: a randomized clinical trial. J Cancer Res Clin Oncol 2006; 132(7):458-465.

(4) Lo C M, Liu C L, Chan S C et al. A randomized, controlled trial of postoperative adjuvant interferon therapy after resection of hepatocellular carcinoma. Ann Surg 2007; 245(6):831-842.

(5) Clavien P A. Interferon: the magic bullet to prevent hepatocellular carcinoma recurrence after resection? Ann Surg 2007; 245(6):843-845.

(6) Llovet J M, Ricci S, Mazzaferro V et al. Sorafenib in advanced hepatocellular carcinoma. N Engl J Med 2008; 359(4):378-390.
(7) Thorgeirsson S S, Grisham J W. Molecular pathogenesis of human hepatocellular carcinoma. Nat Genet. 2002; 31(4):339-346.
(8) Budhu A, Wang X W. The role of cytokines in hepatocellular carcinoma. J Leukoc Biol 2006; 80(6):1197-1213.
(9) El Serag H B, Rudolph K L. Hepatocellular carcinoma: epidemiology and molecular carcinogenesis. Gastroenterology 2007; 132(7):2557-2576.
(10) Ghebranious N, Sell S. Hepatitis B injury, male gender, aflatoxin, and p53 expression each contribute to hepatocarcinogenesis in transgenic mice. Hepatology 1998; 27(2): 383-391.
(11) Nakatani T, Roy G, Fujimoto N, Asahara T, Ito A. Sex hormone dependency of diethylnitrosamine-induced liver tumors in mice and chemoprevention by leuprorelin. Jpn J Cancer Res 2001; 92(3):249-256.
(12) Rogers A B, Theve E J, Feng Y et al. Hepatocellular carcinoma associated with liver-gender disruption in male mice. Cancer Res 2007; 67(24):11536-11546.
(13) Naugler W E, Sakurai T, Kim S et al. Gender disparity in liver cancer due to sex differences in MyD88-dependent IL-6 production. Science 2007; 317(5834):121-124.
(14) Ng I O, Ng M M, Lai E C, Fan S T. Better survival in female patients with hepatocellular carcinoma. Possible causes from a pathologic approach. Cancer 1995; 75(1): 18-22.
(15) Dohmen K, Shigematsu H, Irie K, Ishibashi H. Longer survival in female than male with hepatocellular carcinoma. J Gastroenterol Hepatol 2003; 18(3):267-272.
(16) Tangkijvanich P, Mahachai V, Suwangool P, Poovorawan Y. Gender difference in clinicopathologic features and survival of patients with hepatocellular carcinoma. World J Gastroenterol 2004; 10(11):1547-1550.
(17) Ashizawa T, Okada R, Suzuki Y et al. Clinical significance of interleukin-6 (IL-6) in the spread of gastric cancer: role of IL-6 as a prognostic factor. Gastric Cancer 2005; 8(2):124-131.
(18) Porta C, De Amici M, Quaglini S et al. Circulating interleukin-6 as a tumor marker for hepatocellular carcinoma. Ann Oncol 2008; 19(2):353-358.
(19) Calin G A, Ferracin M, Cimmino A et al. A MicroRNA signature associated with prognosis and progression in chronic lymphocytic leukemia. N Engl J Med 2005; 353 (17):1793-1801.
(20) Lu J, Getz G, Miska E A et al. MicroRNA expression profiles classify human cancers. Nature 2005; 435(7043): 834-838.
(21) Yanaihara N, Caplen N, Bowman E et al. Unique microRNA molecular profiles in lung cancer diagnosis and prognosis. Cancer Cell 2006; 9(3):189-198.
(22) Budhu A, Jia H L, Forgues M et al. Identification of metastasis-related microRNAs in hepatocellular carcinoma. Hepatology 2008; 47(3):897-907.
(23) Schetter A J, Leung S Y, Sohn J J et al. MicroRNA expression profiles associated with prognosis and therapeutic outcome in colon adenocarcinoma. JAMA 2008; 299(4):425-436.
(24) Kim J W, Ye Q, Forgues M et al. Cancer-associated molecular signature in the tissue samples of patients with cirrhosis. Hepatology 2004; 39(2):518-527.
(25) Budhu A, Forgues M, Ye Q H et al. Prediction of venous metastases, recurrence and prognosis in hepatocellular carcinoma based on a unique immune response signature of the liver microenvironment. Cancer Cell 2006; 10(2):99-111.
(26) Ye Q H, Qin L X, Forgues M et al. Predicting hepatitis B virus-positive metastatic hepatocellular carcinomas using gene expression profiling and supervised machine learning. Nat Med 2003; 9(4):416-423.
(27) Yamashita T, Forgues M, Wang W et al. EpCAM and alpha-fetoprotein expression defines novel prognostic subtypes of hepatocellular carcinoma. Cancer Res 2008; 68(5):1451-1461.
(28) Karin M, Greten F R. NF-κB: linking inflammation and immunity to cancer development and progression. Nat Rev Immunol 2005; 5(10):749-759.
(29) Thyrell L, Arulampalam V, Hjortsberg L, Farnebo M, Grander D, Pokrovskaja T K. Interferon alpha induces cell death through interference with interleukin 6 signaling and inhibition of STAT3 activity. Exp Cell Res 2007; 313(19): 4015-4024.
(30) Wands J. Hepatocellular carcinoma and sex. N Engl J Med 2007; 357(19):1974-1976.

What is claimed is:

1. A method of predicting the clinical outcome of a patient diagnosed with hepatocellular carcinoma (HCC), comprising:
   receiving a tumor sample obtained from a patient with HCC;
   measuring a level of miR-26 expression in the tumor sample obtained from the patient, wherein the measuring comprises:
      amplifying by PCR a miR-26 sequence in cells from the tumor sample suspended in a PCR reaction mixture,
      cytocentrifuging the cells onto slides, and
      visualizing intracellular PCR products in the cells by in situ hybridization or immunohistochemistry;
   comparing the level to a non-cancerous control level of miR-26 expression;
   predicting unresponsiveness to interferon (IFN)-α therapy if the level of miR-26 expression in the tumor sample is detected to have a less than 1.5-fold decrease relative to the control, and
   not providing IFN-α therapy to the patient if unresponsiveness to IFN-α therapy is predicted.

2. The method of claim 1, wherein miR-26 is miR-26a-1, miR-26a-2, miR-26b, or a combination thereof.

3. The method of claim 1, wherein the control is a non-cancerous tissue sample obtained from the patient.

4. The method of claim 1, wherein the control is a liver sample from a healthy subject.

5. The method of claim 1, wherein the control is a standard value.

6. The method of claim 2, wherein the control is a non-cancerous tissue sample obtained from the patient.

7. The method of claim 2, wherein the control is a liver sample from a healthy subject.

8. The method of claim 2, wherein the control is a standard value.

9. The method of claim 1, wherein the PCR products include at least one labeled nucleotide selected from digoxigenin-11-dUTP, fluorescein-dUTP, 3H-CTP, or biotin-16-dUTP.

10. A method of excluding a patient diagnosed with HCC as a candidate for IFN-α therapy, comprising:
   receiving a tumor sample obtained from a patient with HCC;
   measuring a level of miR-26 expression in the tumor sample obtained from the patient, wherein the measuring comprises:
      cytocentrifuging cells from the tumor sample to produce a cytocentrifuge preparation on a slide,
      overlaying the slide with a PCR reaction mixture under a coverslip,
      sealing the coverslip,
      subjecting the slide to thermal cycling, and
      visualizing intracellular PCR products on the slide by in situ hybridization with PCR probes, or in situ PCR through direct detection of labeled nucleotides;
   comparing the level of miR-26 expression with a control;
   identifying a patient having a less than 1.5-fold decrease in the level of miR-26 expression in the tumor sample relative to the control as a subject unlikely to respond to IFN-α therapy; and
   excluding the identified patient as a candidate for IFN-α therapy.

11. The method of claim 10, wherein miR-26 is miR-26a-1, miR-26a-2, miR-26b, precursors thereof, or a combination thereof.

12. The method of claim 10, wherein the control is a non-cancerous tissue sample obtained from the patient.

13. The method of claim 10, wherein the control is a liver sample from a healthy subject.

14. The method of claim 10, wherein the control is a standard value.

15. The method of claim 11, wherein the control is a non-cancerous tissue sample obtained from the patient.

16. The method of claim 11, wherein the control is a liver sample from a healthy subject.

17. The method of claim 11, wherein the control is a standard value.

18. The method of claim 10, wherein the labeled nucleotides include at least one of digoxigenin-11-dUTP, fluorescein-dUTP, 3H-CTP, or biotin-16-dUTP.

* * * * *

SEQUENCE LISTING

```
<160> NUMBER OF SEQ ID NOS: 5

<210> SEQ ID NO 1
<211> LENGTH: 77
<212> TYPE: RNA
<213> ORGANISM: Homo sapiens

<400> SEQUENCE: 1
guggccucgu ucaaguaauc caggauaggc ugugcagguc ccaaugggcc uauucuuggu    60
uacuugcacg gggacgc                                                   77

<210> SEQ ID NO 2
<211> LENGTH: 84
<212> TYPE: RNA
<213> ORGANISM: Homo sapiens

<400> SEQUENCE: 2
ggcuguggcu ggauucaagu aauccaggau aggcuguuuc caucugugag gccuauucuu    60
```

```
gauuacuugu uucuggaggc agcu                                              84

<210> SEQ ID NO 3
<211> LENGTH: 77
<212> TYPE: RNA
<213> ORGANISM: Homo sapiens

<400> SEQUENCE: 3
ccgggaccca guucaaguaa uucaggauag guugugugcu guccagccug uucuccauua       60
cuuggcucgg ggaccgg                                                      77

<210> SEQ ID NO 4
<211> LENGTH: 22
<212> TYPE: RNA
<213> ORGANISM: Homo sapiens

<400> SEQUENCE: 4
uucaaguaau ccaggauagg cu                                                22

<210> SEQ ID NO 5
<211> LENGTH: 21
<212> TYPE: RNA
<213> ORGANISM: Homo sapiens

<400> SEQUENCE: 5
uucaaguaau ucaggauagg u                                                 21
```